(12) United States Patent
Benz et al.

(10) Patent No.: US 7,125,969 B1
(45) Date of Patent: Oct. 24, 2006

(54) ETS-RELATED GENE OVEREXPRESSED IN HUMAN BREAST AND EPITHELIAL CANCERS

(75) Inventors: Christopher C. Benz, Novato, CA (US); Gary K. Scott, Berkeley, CA (US); Chuan-Hsiung Chang, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 08/978,217

(22) Filed: Nov. 25, 1997

Related U.S. Application Data

(60) Provisional application No. 60/031,504, filed on Nov. 27, 1996.

(51) Int. Cl.
  *C07H 21/04* (2006.01)
(52) U.S. Cl. .................................. 536/23.1; 536/23.5
(58) Field of Classification Search ............... 536/23.1, 536/23.5, 24.1, 24.3, 24.31, 24.33; 435/69.1, 435/70.1, 320.1, 325
See application file for complete search history.

(56) References Cited

U.S. PATENT DOCUMENTS 5,789,200 A * 8/1998 Kola et al.

OTHER PUBLICATIONS

Dalton, S. et al., Characterization of SAP-1, a protein recruited by serum response factor t the c-fos serum response element. Cell, 68: 597-612, Feb. 1997.*
Giovane, A. et al., Net, a new ets transcription factor that is activated by Ras. Genes and Development, 8: 1502-1513, 1994.*
Filloux, A. et al. Protein secretion in gram-negative bacteria: transport across the outer membrane involves common mechanisms in different bacteria. The EMBO Journal, 9(13): 4322-4329, 1990.*
Accession No. R50578, Database Genbank, EST, Hillier, L. et al., May 1995.*
Accession No. H12657, Database Genbank, EST, Hillier, L. et al., Jun. 1995.*
Accession No. T27397, Database Genbank, EST, Bell, G.I. et al., Dec. 1994.*
Accession No. R73021, Database Genbank, EST, Hillier, L. et al., Jun. 1995.*
Promega Corporation, Promega Protocols and Applications Guide, Second Edition, pp. 145-153, Mar. 1991.*
Lazar, E. et al. Transforming growth factor alpha: mutation of aspartic acid 47 and leucine 48 results in different biological activities. Molecular and Cellular Biology, 8(1): 1247-1252, Mar. 1988.*
Burgess, W.H. et al. Possible dissociation of the heparin-binding and mitogenic activities of heparin-binding (acidic fibroblast) growth factor-1 from its receptor-binding activities by site-directed mutagenesis of a single lysine residue. J. Cell Biolo, Nov. 1990.*
Molecular Cell Biology, Ed. H. Lodish et al., Scientific American Books, New York, 1995; pp. 442, 445-453.*
Boehringer Mannheim Biochemicals, 1994 Catalog, p. 91.*
ICN Biomedicals, Inc., 1990-'91 Catalog, pp. RC-96 and RC-99.*
Degnan et al., "The ets multigene family is conserved throughout the Metazoa" (1993) *Nucl. Acids. Res.* 21:3479-3484.
Galang et al., "Oncogenic Neu/ErbB-2 Increases ets, AP-1, and NK-κB-dependent Gene Expression, and Inhibiting Ets Activation Blocks Neu-mediated Cellular Transformation" (1996) *J. Biol. Chem.* 271:7992-7998.
Hillier et al., GenBank locus R73021, "The WashU-Merck EST Project", Jun. 2, 1995.
Bell et al., GenBank locus T27397, "Human pancreatic islet cDNAs", Dec. 6, 1994.
Hillier et al., GenBank locus T78501, "The WashU-Merck EST Project", Mar. 15, 1995.
Giovane et al. "Locations of the ets Subfamily Members net, elkl, and sap 1 (ELK3, ELK1, and ELK4) on Three Homologous Regions of the Mouse and Human Genomes" (1995) *Genomics* 29:769-772.
Janknecht and Nordheim, "Gene regulation by Ets proteins" (1993) *Biochem. Biophys. Acta.* 1155:346-356.
Jonsen et al., "Characterization of the Cooperative Function of Inhibitory Sequences in Ets-1" (1996) *Mol. Cell. Biol.* 16:2065-2073.
Klambt, The *Drosophila* gene pointed encodes two ETS-like proteins which are involved in the development of the midline glial cells: (1993) *Development* 117:163-176.
Kodandapani et al. "A new pattern for helix-turn-helix recognition revealed by the PU.1 ETS-domain-DNA complex" (1996) *Nature* 380:456-460.
Laudet et al. "Evolution of the ets Gene Family" (1993) *Biochem. Biophys. Res. Commun.* 190:8-14.
Lautenberger et al. "Genomic dispersal of the ets gene family during metazoan evolution" (1992) *Oncogene* 7:1713-1719.
Lennon et al. The I.M.A.G.E. Consortium: An Integrated Molecular Analysis of Genomes and Their Expression (1996) *Genomics* 33:151-152.
Noonberg et al. "Inhibition of transcription factor binding to the HER2 promoter by triplex-forming oligodeoxyribonucleotides" (1994) *Gene* 149:123-126.
O'Hagan et al. "Activation of HER2/neu induces overexpression of the Ets-related transcription factor PEA3" (1996) *Amer. Assoc. Cancer Res.* 37:3575.

(Continued)

*Primary Examiner*—Sheela J. Huff
(74) *Attorney, Agent, or Firm*—Tom Hunter; Beyer Weaver & Thomas LLP

(57) ABSTRACT

This invention provides for a cDNA that is a coding region of a previously unknown member of the ETS transcription regulator family. The gene described herein (designated ESX) is located at chromosome 1q32 a region amplified in 50% of early breast cancers. The ESX gene of this invention is associated with the etiology of various cancers including breast cancers. Detection of the ESX gene or gene product is thus of diagnostic and/or prognostic value.

2 Claims, 21 Drawing Sheets

OTHER PUBLICATIONS

Schmitz and Baeuerle "The p65 subunit is responsible for the strong transcription activating potential of NF-χB" (1991) *EMBO J.* 10:3805-3817.

Scott et al. Binding of an ETS-related Protein within the DNase I Hypersensitive Site of the HER2/neu Promoter in Human Breast Cancer Cells: (1994) *J. Biol. Chem.* 269:19848-19858.

Seipel et al. "Different activation domains stimulate transcription from remote ('enhancer') and proximal ('promoter') positions" (1992) *EMBO J.* 11:4961-4968.

Shipley et al. "Mapping of the Human SAP1 (SRF Accessory Protein 1) Gene and SAP2, a Gene Encoding a Related Protein, to Chromosomal Bands 1q32 and 12q23, Respectively" (1994) *Genomics* 23:710-711.

van de Wetering et al. "Sox-4, an Sry-like HMG box protein, is a transcriptional activator in lymphocytes" (1993) *EMBO J.* 12:3847-3854.

Wasylyk et al. "The Ets family of transcription factors" (1993) *Eur. J. Biochem.* 211:7-18.

Werner et al. "The Solution Structure of the Human ETS1-DNA Complex Reveals a Novel Mode of Binding and True Side Chain Intercalation" (1995) *Cell* 83:761-771.

Tymms, et al. AF016294, "A novel epithelial-expressed ETS gene, ELF3: human and murine cDNA sequences, murine genomic organization, human mapping to 1q32.2 and expression in tissues and cancer", Jan. 16, 1988.

Oettgen et al. "Isolation and Characterization of a Novel Epithelium-Specific Transcription Factor, ESE-1, a Member of the ets Family" (1997) *Mol. Cell. Biol.* 17:4419-4433.

Chang et al. "ESX: a structurally unique Ets overexposed early during human breast tumorigenesis" (1997) *Oncogene* 14:1617-1622.

Asada et al. (2002) "External Control of Her2 Expression and Cancer Cell Growth by Targeting a Ras-Linked Coactivator", PNAS 99:20 12747-12752.

Oettgen et al. (1997) "The Novel Epithelial-Specific Ets Transcription Factor Gene ESX Maps to Human Chromosome 1Q32.1", Genomics 45: 456-457.

Neve et al. (1998) "The Epithelium-Specific Ets Transcription Factor ESX Is Associated with Mammary Gland Development and Involution", The FASEB Journal 12: 1541-1550.

* cited by examiner

ESX ORF DNA Sequence (1 to 1116) -> 1-phase Translation    371 Amino acids
DNA sequence     1116 b.p.     ATGGCTGCAACC ... agtcggaactga  linear    MW: 41428 Dalton

```
1/1                          31/11                                                     61/21
ATG GCT GCA ACC ACC TGT GAG ATT AGC AAC ATT TTT AGC AAC TAC TTC AGT GCG ATG TAC AGC TCG GAG GAC TCC ACC CTG GCC TCT GTT CCC
Met ala ala thr thr cys glu ile ser asn ile phe ser asn tyr phe ser ala met tyr ser ser glu asp ser thr leu ala ser val pro
91/31                        121/41                                                    151/51
CCT GCT GCC ACC TTT GGG GCC GAT GAC TTG GTA CTG ACC CTG AGC AAC CCC CAG ATG TCA TTG GAG GGT ACA GAG AAG GCC AGC TGG TTG
pro ala ala thr phe gly ala asp asp leu val leu thr leu ser asn pro gln met ser leu glu gly thr glu lys ala ser trp leu
181/61                       211/71                                                    241/81
GGG GAA CAG CCC CAG TTC TGG TCG AAG ACG CAG GTT CTG GAC GTT CTG AAG ACG CAG GTT CTG GAC TGG ATC AGC TAC CAA GTG GAG AAG AAC AAG TAC GAC GCA AGC ATT
gly glu gln pro gln phe trp ser lys thr gln val leu asp val leu lys thr gln val leu asp trp ile ser tyr gln val glu lys asn lys tyr asp ala ser ile
271/91                       301/101                                                   331/111
GAC TTC TCA CGA TGT GAC ATG GAT GGC GCC ACC CTC TGC AAT TGT GCC CTT GAG GAG CTG CGT CTG TTT GGG CCT CTG GGG GAC CAA
asp phe ser arg cys asp met asp gly ala thr leu cys asn cys ala leu glu glu leu arg leu phe gly pro leu gly asp gln
361/121                      391/131                                                   421/141
CTC CAT GCC CAG CTG CGA GAC CTC ACT CCC AGC TCT TCT GAT GAG CTC AGT TGG ATC ATT GAG CTG CTG GAG AAG GAT GGC AGC ATG GCC TTC
leu his ala gln leu arg asp leu thr pro ser ser ser asp glu leu ser trp ile ile glu leu leu glu lys asp gly met ala phe
451/151                      481/161                                                   511/171
CAG GAG GCC CTA GAC GCC CCA GGG CCC TTT GAC CAG GGC AGC CAG GAG CCC TTT GCC CAG GAG CTG GAC GAC GGT CAG CAA GCC AGC CCC TAC CAC
gln glu ala leu asp ala pro gly pro phe asp gln gly ser gln glu pro phe ala gln glu leu asp asp gly gln gln ala ser pro tyr his
541/181                      571/191                                                   601/201
CCC GGC AGC TGT GGC GCA GGA GCC CCC TCC CCT GGC AGC GTC TCC GAC GGG ACT GGT GCT TCT CGG AGC TCC CAC TCC TCA
pro gly ser cys gly ala gly ala pro ser pro gly ser asp val ser thr ala gly thr gly ala ser arg ser ser his ser ser
631/211                      661/221                                                   691/231
GAC TCC GGT GGA AGT GAC GTG GAC CTG GAT CCC ACT GAT GGC AAG CTC CCC TTC AGC GAT GGT TTT CGT GAC TGC AAG GGG GAT CCC
asp ser gly gly gly ser asp val asp leu asp pro thr asp gly lys leu pro phe ser asp gly phe arg asp cys lys gly asp pro
```

Fig. 1

```
811/271
AGA GGC ACC CAC CTG TGG GAG TTC ATC CGG GAC ATC CTC ATC CAC CCG GAG CTC AAC GAG CTC ATG AAG TGG GAG AAT CGG CAT GAA
arg gly thr his leu trp glu phe ile arg asp ile leu ile his pro glu leu asn glu leu met lys trp glu asn arg his glu
901/301                                                                                     961/321
GGC GTC TTC aag TTC CTG CGC TCC GAG GCT GTG GCC CAA CTA GGC CAA AAG AAA AAG AAC AGC AAC ATG AAG TGG GAG AAG CTG AGC
gly val phe lys phe leu arg ser glu ala val ala gln leu trp gly gln lys lys lys asn ser asn met thr glu lys leu ser
991/331                                                                                     1051/351
CGG GCC ATG AGG TAC TAC AAA CGG GAG ATC CTG GAA CGG GAT GGC CGG CGA CTC GTC TAC AAG TTT GGC AAA AAC TCA AGC GGC
arg ala met arg tyr tyr lys arg glu ile leu glu arg val asp gly arg arg leu val tyr lys phe gly lys asn ser ser gly
1081/361                                                             1111/371
TGG AAG GAG GAA GAG GTT CTC CAG AGT CGG AAC TGA
trp lys glu glu glu val leu gln ser arg asn OPA
```

Fig. 1 (cont.)

```
MAATCEISNIFSNYFSAMYSSEDSTLASVPPAATFGADDLVLTLSNPQMSLEG      53
TEKASWLGEQ PQFWSKTQVLDWISYQVEKNKYDASAIDFSRCDMDGATLC NCA    106
LEELRLVFGPLGDQLHAQLRDLTSSSSDELSWIIELLEKDGMAFQEALDPGF      159
DQGSPFAQELLDDGQQASPYHPGSCGAGA PSPGSSDVSTAGTGASRSHSSDS     212
GGSDVDLDPTDGKLFPSDGFRDCKKG DPKHGKRKRGRPRKLSKEYWDCLEGKK    265
SKHAPRGT HLWEFIRDILIHPELNEGLMKWENRHEGVFKFLRSEAVAQLWGQK    318
KKNSNMTYEKLSRAMRYYYKREILERVDGRRLVYKF GKNSSGWKEEEVLQSRN    371
```

Fig. 2A

```
Consensus+:    P      PW     VW       W    E        G     LC
ESX (64-103):  PQFWSKTQVLDWISYQVEKNKYDASAIDFSRCDMDGATLC
               P+ W++T V DW+ + v  N++    +DF  + M+GA LC
ETS-1(69-106): PRQWTETHVRDWVMWAV--NEFSLKGVDFQKFCMNGAALC
```

Fig. 2B

ESX(188-238):   APSPGSSDVSTAGTGASRSSHSSDSGGSDVDLDPTDGKLFPSDGFRDCKKG
                APS   S  S++ + S SS SS S  SD + +    L PS  F
SOX4(370-420):  APSSAPSHASSSASSHSSSSSGSSSSDDEFEDDLLDLNPSSNFESMSLG

```
                    α₁                    β₁           β₂        α₂
Consensus⁺:    LWQFLL LL D              I W           EK     VAR W
                * •* *                   •                     *
ESX (274-354): HLWEFIRDILIHPEINEGLMKWENRHEGVFKFLRSEAVAQLW
               +LWEF+ +L    +KW  R +G+FK  + S+AV++LW
ELF-1 (209-289): YLMEFLLALLQDKATCPKYIKWTQREKGIFKLVDSKAVSRLW "turn"          α₃                β₃ "wing"  β₄
                 G  K   P  MNY KLSR LRYY          I  K  G  R Y  F
                 *             • •                         •
               GQKKKNSNMTYEKLSRAMRYYYKREILERVDGRRLLVYKF
               G+ K   +M YE + RA+RYYY+R IL  +V+G+RLVY+F
               GKHKNKPDMNYETMGRALRYYYQRGILAKVEGQRLVYQF Fig. 2D
```

Human ESX Protein Sequence

```
MAATCEISNIFSNYFSAMYSSEDSTLASVPPAATFGADDLVLTLSNPQMSLEG    53
TEKASWLGEQPQFWSKTQVLDWISYQVEKNKYDASAIDFSRCDMDGATLCNCA   106
LEELRLVFGPLGDQLHAQLRDLTSSSSDELSWIIELLEKDGMAFQEALDPGPF   159
DQGSPFAQELLDDGQQASPYHPGSCGAGAPSPGSSDVSTAGTGASRSSHSSDS   212
GGSDVDLDPTDGKLFPSDGFRDCKKGDPKHGKRKRGRPRKLSKEYWDCLEGKK   265
SKHAPRGTHLWEFIRDILIHPELNEGLMKWENRHEGVEKFLRSEAVAQLWGQK   318
KKNSNMTYEKLSRAMRYYYKREILERVDGRRLVYKFGKNSSGWKEEVLQSRN    371
```

Fig. 2E

1/1
ATG GCT GCA ACC TGT GAG ATT AGC AAC ATT TTT AGC AAC TAC TTC AGT GCG ATG TAC AGC
Met ala ala thr cys glu ile ser asn ile phe ser asn tyr phe ser ala met tyr ser
61/21                                                          31/11
TCG GAG GAC TCC ACC CTG GCC TCT GTT CCC CCT GCT GCC ACC TTT GGG GCC GAT GAC TTG
ser glu asp ser thr leu ala ser val pro pro ala ala thr phe gly ala asp asp leu
121/41                                                          91/31
GTA CTG ACC CTG AGC AAC CCC CAG ATG TCA TTG GAG GGT ACA GAG AAG GCC AGC TGG TTG
val leu thr leu ser asn pro gln met ser leu glu gly thr glu lys ala ser trp leu
181/61                                                          151/51  E2▼E3
GGG GAA CAG CCC CAG TTC TGG TCG AAG ACG CAG GTT CTG GAC TGG ATC AGC TAC CAA GTG
gly glu gln pro gln phe trp ser lys thr gln val leu asp trp ile ser tyr gln val
241/81                                                          211/71
GAG AAG AAC AAG TAC GAC GCA AGC GCC ATT GAC TTC TCA CGA TGT GAC ATG GAT GGC GCC
glu lys asn lys tyr asp ala ser ala ile asp phe ser arg cys asp met asp gly ala
301/101                                                         271/91
ACC CTC TGC AAT TGT GCC CTT GAG GAG CTG CGT CTG GTC TTT GGG CCT CTG GGG GAC CAA
thr leu cys asn cys ala leu glu glu leu arg leu val phe gly pro leu gly asp gln
361/121                                                         331/111
CTC CAT GCC CAG CTG CGA GAC CTC ACT TCC AGC TCT TCT GAT GAG CTC AGT TGG ATC ATT
leu his ala gln leu arg asp leu thr ser ser ser ser asp glu leu ser trp ile ile
421/141                                                         391/131                E4▼E5
GAG CTG CTG GAG AAG GAT GGC ATG GCC TTC CAG GAG GCC CTA GAC CCA GGG CCC TTT GAC
glu leu leu glu lys asp gly met ala phe gln glu ala leu asp pro gly pro phe asp
                                                                451/151

Fig. 4

```
481/161
CAG GGC AGC CCC TTT GCC CAG GAG CTG CTG GAC GAC GGT CAG CAA GCC AGC CCC TAC CAC
gln gly ser pro phe ala gln glu leu leu asp asp gly gln gln ala ser pro tyr his
541/181                                                                  E5▼E6
CCC GGC AGC TGT GGC GCA GGA GCC CCC TCC CCT GGC AGC GTC TCC ACC GCA GGG
pro gly ser cys gly ala gly ala pro ser pro gly ser asp val ser thr ala gly
601/201
ACT GGT GCT TCT CGG AGC TCC CAC TCC TCA GAC TCC GGT GGA AGT GAC GTG GAC CTG GAT
thr gly ala ser arg ser ser his ser ser asp ser gly gly ser asp val asp leu asp
661/221                           E6▼E7 691/231
CCC ACT GAT AAG CTC TTC CCC AGC GAT GGT TTT CGT GAC TGC AAG AAG GGG GAT CCC
pro thr asp lys leu phe pro ser asp gly phe arg asp cys lys lys gly asp pro
721/241                                                       751/251
AAG CAC GGG AAG CGG AAA CGA GGC CGG CCC CGA AAG CTG AGC AAA GAG TAC TGG GAC TGT
lys his gly lys arg lys arg gly arg pro arg lys leu ser lys glu tyr trp asp cys
781/261                    E7▼E8 811/271
CTC GAG GGC AAG AAG AGC AAG GCG CCC AGA GGC ACC CAC CTG TGG GAG TTC ATC CGG
leu glu gly lys lys ser lys ala pro arg gly thr his leu trp glu phe ile arg
841/281                                                       871/291
GAC ATC CTC ATC CAC CCG GAG CTC AAC GAG GGC CTC ATG AAG TGG GAG AAT CGG CAT GAA
asp ile leu ile his pro glu leu asn glu gly leu met lys trp glu asn arg his glu
901/301                                                       931/311
GGC GTC TTC aag TTC CTG CGC TCC GAG GCT GTG GCC CAA CTA TGG GGC CAA AAG AAA AAG
gly val phe lys phe leu arg ser glu ala val ala gln leu trp gly gln lys lys lys
```

Fig. 4 (cont.)

```
961/321
AAC AGC AAC ATG ACC TAC GAG AAG CTG AGC CGG GCC ATG AGG TAC TAC AAA CGG GAG
asn ser asn met thr tyr glu lys leu ser arg ala met arg tyr tyr lys arg glu
1021/341                                                            1051/351
ATC CTG GAA CGG GTG GAT GGC CGG CGA CTC GTC AAG TTT GGC AAA AAC TCA AGC GGC
ile leu glu arg val asp gly arg arg leu val lys phe gly lys asn ser ser gly
1081/361                                        1111/371
TGG AAG GAG GAA GAG GTT CTC CAG AGT CGG AAC TGA
trp lys glu glu glu val leu gln ser arg asn OPA
```

```
mESX   1 MAATCEISNVFSNYFNAMYSSEDPTLAPAPP.TTFGTEDLVLTLNNQQMT  49
         ||||||||||:||||.||||||| ||| || ||| :||||||.| ||.
hESX   1 MAATCEISNIFSNYFSAMYSSEDSTLASVPPAATFGADDLVLTLSNPQMS  50

E₂/E₃
                ↓
mESX  50 LEGPEKASWTSERPQFWSKTQVLEWISYQVEKNKYDASSIDFSRCNMDGA  99
         ||| ||||||  |.||||||||||||||||||||||||||:|||||:||||
hESX  51 LEGTEKASWLGEQPQFWSKTQVLDWISYQVEKNKYDASAIDFSRCDMDGA 100

E₃/E₄
                                  ↓
mESX 100 TLCSCALEELRLVFGPLGDQLHAQLRDLTSNSSDELSWIIELLEKDGMSF 149
         |||:|||||||||||||||||||||||||.|||||||||||||||||.|
hESX 101 TLCNCALEELRLVFGPLGDQLHAQLRDLTSSSSDELSWIIELLEKDGMAF 150

E₄/E₅                                   E₅/E₆
               ↓.                                      ↓
mESX 150 QESLGDLGPSDQGSPFAQELLDDGRQASPYYCSTYGPGAPSPGSSDVSTA 199
         ||.| || |||||||||||||||.|||||:  .||| APSPGSSDVSTA
hESX 151 QEAL.DPGPFDQGSPFAQELLDDGQQASPYHPGSCGAGAPSPGSSDVSTA 199

E₆/E₇
                                   ↓
mESX 200 GTATPQSSHASDSGGSDVDLDLTESKVFPRDDFTDYKKGEPKHGKRKRGR 249
         GT A    S HS SDSGGSDVDLD  =·= |||  ||| KKG PKHGKRKRGR
hESX 200 GTGASRSSHSSDSGGSDVDLDPTDGKLFPSDGFRDCKKGDPKHGKRKRGR 249

E₇/E₈
               ↓.
mESX 250 PRKLSKEYWDCLEGKKSKHAPRGTHLWEFIRDILIHPELNEGLMKWENRH 299
         PRKLSKEYWDCLEGKK|||||||HLWEFIRDILIHPELNEGLMKWENRH
hESX 250 PRKLSKEYWDCLEGKKSKHAPRGTHLWEFIRDILIHPELNEGLMKWENRH 299
```

Fig. 5

```
                                              E₈/E₉
                                               ↓
mESX 300  EGVFKFLRSEAVAQLWGQKKKNSNMTYEKLSRAMRYYYKREILERVDGRR  349
hESX 300  EGVFKFLRSEAVAQLWGQKKKNSNMTYEKLSRAMRYYYKREILERVDGRR  349 mESX 350  LVYKFGKNSSGWKEEEVGESRN  371
hESX 350  LVYKFGKNSSGWKEEEVLQSRN  371
```

- POINTED/A-Region
- Serine-Rich Box
- Nuclear Targeting Sequence
- ETS-DNA Binding Domain

Fig. 5 (cont.)

```
WT  5' GGAGGAGGGCTGCTTGAGGAAGTATAAGAAT 3'
m1  5' --------TA--------------------- 3'
m2  5' ---------------C--------------- 3'
m3  5' ------------------AG------------ 3'
m4  5' ------------------CC------------ 3'
m5  5' -------------------------C------ 3'
```

ETS-RELATED GENE OVEREXPRESSED IN HUMAN BREAST AND EPITHELIAL CANCERS

CROSS-REFERENCE TO RELATED APPLICATIONS

This is a continuation-in-part of provisional patent application U.S. Ser. No. 60/031,504, filed on Nov. 27, 1996, which is herein incorporated by reference for all purposes.

STATEMENT AS TO RIGHTS TO INVENTIONS MADE UNDER FEDERALLY SPONSORED RESEARCH AND DEVELOPMENT

This invention was made with Government support under Grant No. CA44768 and CA36773, awarded by the National Institutes of Health. The Government of the United States of America may have certain rights in this invention.

FIELD OF THE INVENTION

This invention pertains to the field of oncology. In particular, this invention pertains to the discovery of a transcription factor gene implicated in the etiology of human epithelial cancers, including breast cancer, and other malignancies including gastric, ovarian, and lung adenocarcinomas.

BACKGROUND OF THE INVENTION

Many cancers are believed to result from a series of genetic alterations leading to progressive disordering of normal cellular growth mechanisms (Nowell (1976) *Science* 194:23, Foulds (1958) *J. Chronic Dis.* 8:2). The deletion or multiplication of copies of whole chromosomes or chromosomal segments, or specific regions of the genome are common (see, e.g., Smith et al. (1999) *Breast Cancer Res. Treat.*, 18: Suppl. 1: 5–14; van de Vijer & Nusse (1991) *Biochim. Biophys. Acta.* 1072: 33–50; Sato et al. (1990) *Cancer. Res.*, 50: 7184–7189). In particular, the amplification and deletion of DNA sequences containing proto-oncogenes and tumor-suppressor genes, respectively, are frequently characteristic of tumorigenesis. Dutrillaux, et al.(1990) *Cancer Genet. Cytogenet.*, 49: 203–217. As an example, overexpression of the HER2/neu (c-erbB-2) proto-oncogene product is found in approximately 20–30% of primary breast cancers and in a similar fraction of human gastric, ovarian, and lung carcinomas. For many of these malignancies, this overexpressed membrane growth factor receptor (p185$^{HER2}$) is associated with HER2 gene amplification, more aggressive tumor growth, and reduced patient survival. Maguire & Greene (1989) *Semin. Oncol.* 16: 148–155; Singleton & Strickler (1992) *Pathol. Annu* 1: 165–190; Tripathy & Benz (1993) in *Oncogenes and Tumor Suppressor Genes in Human Malignancies* (Benz and Liu, eds.) pp. 15–60, Kluwer, Boston. In approximately 10–20% of HER2-overexpressing breast tumors, some gastric, and virtually all HER2-positive lung cancers, HER2-m RNA and protein overexpression occur in the absence of increased gene copy number, suggesting that HER2 transcriptional dysregulation may be a fundamental defect of clinical significance in these malignancies. Berger et al. (1988) *Cancer Res.* 48: 1238–1243; Kameda et al. (1990) *Cancer Res.* 50: 8002–8009; Kern et al. (1990) *Cancer Res.* 50: 5184–5191; King et al. (1989) *Cancer Res.* 49: 4185–4191; Slamon et al. (1989) *Science* 244: 707–712; Tandon et al. (1989) *J. Clin. Oncol.* 7: 1120–1128. It has been speculated that a primary defect leading to dysregulated HER2 transcription might also predispose to the in vivo development of gene amplification and stable acquisition of a more malignant tumor cell phenotype. Kameda et al., supra.; King et al., supra.; Hynes et al. (1989) *J. Biol. Chem.* 39: 167–173; Kraus et al. (1987) *EMBO J.* 6: 605–610; Pasleau et al. (1993) *Oncogene* 8: 849–854.

Recently, a previously unrecognized response element similar to those recognized by the ets transcriptional regulator family was identified within both the human HER2 and murine neu promoters. Scott et al. (1994) *J. Biol. Chem.* 269: 19848–19858. The ets multigene family of transcriptional regulators includes more than thirty known members that are involved in early embryonic development and late tissue maturation, directing stage-specific and tissue-restricted programs of gene expression. The ETS transcription factors, which are recognizable primarily by their 85 amino acid ETS DNA-binding domain, are dispersed across all metazoan lineages into distinct subfamilies. Ets genes can produce malignancies in humans and other vertebrates when overexpressed or rearranged into chimeras retaining the ETS domain. However, the particular ets gene family member responsible for HER2/neu-mediated cancers and other related cancers was not known prior to this invention.

Because most, if not all, cancers involve dysregulation of gene expression, a need exists for information as to transcription factors and other regulatory moieties that are involved in mediating the dysregulation. Such knowledge is helpful in developing methods and compositions for use in diagnosing and treating cancers. The present invention fulfills this and other needs.

SUMMARY OF THE INVENTION

This invention provides both human and mouse forms of a previously unknown gene that appears to be a member of the ETS family of genes. The particular gene identified herein (designated ESX for epithelial-restricted with serine box) is a transcription factor associated with the etiology of cancers, including epithelial cancers. This transcription factor is located at chromosome 1q32 a region amplified in 50% of early breast cancers.

The human ESX gene of this invention is identified as a member of the ETS gene family by significant sequence identity with ETS genes in the DNA binding domain. In particular, the C-terminal ETS DNA binding domain of ESX (aa 274–354) contains 27 of the 38 most highly conserved (consensus) residues found in the DNA-binding domain of all Ets family members (see, e.g., FIG. 2d).

However, the ESX gene of this invention differs from other Ets family having the five non-conservative changes in its DNA-binding domain consensus residues, including three within the first helix ($a_1$) that enhance basicity in a region likely to make critical contact with the minor groove phosphate backbone of bound DNA (Werner et al (1995) *Cell* 83: 761–771; Kodandapani et al. (1996) *Nature* 380: 456–460). ESX may be assigned to the E74/Elf-1 subfamily on the basis of its sequence homology within the ETS domain (Lautenberger et al. (1992) *Oncogene* 7: 1713–1719; Laudet et al. (1993) *Biochem. Biophys. Res. Commun.* 190: 8–14; Degnan et al. (1993) *Nucl. Acids Res.* 21: 3479–3484; Wasylyk et al. (1993) *Eur. J. Biochem.* 211: 7–18; Janknecht and Nordheim (1993) *Biochem. Biophys. Acta.* 1155: 346–356).

In a preferred embodiment, this invention provides an isolated human nucleic acid comprising a nucleotide sequence encoding at least about five contiguous amino acids of a human ESX transcription factor variable region polypeptide, wherein said variable region has an amino acid sequence as set forth in SEQ ID NO: 7 or conservative substitutions of this amino acid sequence. The isolated nucleic acid of can encode an ESX transcription factor having an amino acid sequence as set forth in SEQ ID NO: 2 and may have the nucleotide sequence as set forth in SEQ ID NO: 1. The nucleic acid may be one that is amplified from a genomic library using the primer pairs designated by SEQ-ID No. 13 and SEQ ID NO. 14. The nucleic acid may hybridize to a clone of a human ESX gene under stringent conditions and may further comprise a vector. In one embodiment the variable region encoded by the nucleic acid has a sequence as set forth in SEQ ID NO.: 7. Particularly preferred nucleic acids have a smallest sum probability of less than about 0.5, more preferably less than about 0.2 most preferably less than about 0.1 when compared to a nucleotide sequence as set forth in SEQ ID NO: 6 using a BLASTN algorithm using default parameters as described known to those of skill in the art and as disclosed herein.

In another embodiment, this invention provides an isolated nucleic acid comprising a label and a nucleotide sequence encoding a carboxy terminal domain of a human ESX transcription factor, where the carboxy terminal domain has an amino acid sequence as set forth in SEQ ID NO: 12 or conservative substitutions of this amino acid sequence. This nucleic acid is preferably free of dideoxynucleotides. This nucleic acid is also preferably single stranded and more preferably is a sense strand. Particularly preferred labels are selected from the group consisting of a radionucleide, a fluorescent label, and an enzymatic label.

In another embodiment, this invention provides an isolated nucleic acid encoding a human ESX transcription factor polypeptide comprising at least 8 contiguous amino acids from a polypeptide sequence encoded by a nucleic acid as set forth in SEQ ID NO: 1, wherein: the polypeptide, when presented as an antigen, elicits the production of an antibody that specifically binds to a polypeptide sequence encoded by a nucleic acid as set forth in SEQ ID NO: 1; and the polypeptide does not bind to antisera raised against a polypeptide encoded by a nucleic acid sequence as set forth in SEQ ID NO: 1, that has been fully immunosorbed with a polypeptide encoded by a nucleic acid sequence as set forth in SEQ ID NO: 1.

In another embodiment, this invention provides an isolated murine (e.g., mouse) nucleic acid comprising a nucleotide sequence encoding at least about five, more preferably at least about 10, and most preferably at least about 20, 30, or even 50 contiguous amino acids of a murine ESX transcription polypeptide (e.g., as illustrated in FIG. 5), or conservative substitutions of this amino acid sequence. The isolated nucleic acid can encode a murine ESX transcription factor having an amino acid sequence as set forth in FIG. 5 or FIG. 11. In a preferred embodiment, the cDNA is amplified (e.g., from total mRNA) using primers corresponding e.g., to the terminal 17–30, more preferably to the 5' and 3' terminal 17, 20, 21, 25, or 30 nucleotides of the mouse cDNA (see, e.g. FIG. 5). One of skill will readily appreciate that numerous other suitable primers can be identified using the sequence information provided herein. The nucleic acid may hybridize to a clone of a murine ESX gene (e.g. SEQ ID No: 15) or cDNA under stringent conditions and may further comprise a vector.

In another embodiment, this invention provides an isolated nucleic acid comprising a label and a nucleotide sequence encoding a murine ESX transcription factor (FIG. 5) or conservative substitutions of the amino acid sequence comprising the murine ESX transcription factor. This nucleic acid is preferably free of dideoxynucleotides. This nucleic acid is also preferably single stranded and more preferably is a sense strand. Particularly preferred labels are selected from the group consisting of a radionucleide, a fluorescent label, and an enzymatic label.

In still yet another embodiment, this invention provides an isolated nucleic acid encoding a murine ESX transcription factor polypeptide comprising at least 8 contiguous amino acids from a polypeptide sequence encoded by a nucleic acid as set forth in SEQ ID NO: 15 or from a murine polypeptide sequence as illustrated in FIG. 5, wherein: the polypeptide, when presented as an antigen, elicits the production of an antibody that specifically binds to a polypeptide sequence encoded by a nucleic acid as set forth in SEQ ID NO: 15, or the murine polypeptide of FIG. 5, and the polypeptide does not bind to antisera raised against a polypeptide encoded by a nucleic acid sequence as set forth in SEQ ID NO: 15, or the murine polypeptide of FIG. 5, that has been fully immunosorbed with a polypeptide encoded by a nucleic acid sequence as set forth in SEQ ID NO: 15 or with the murine polypeptide of FIG. 5.

This invention also provides for human ESX polypeptides. In one embodiment the human ESX polypeptide is an isolated ESX polypeptide comprising a subsequence of at least 5, more preferably at least 10, and more preferably at least 20, 30, 40, or even 50 contiguous amino acids of a polypeptide encoded by a nucleic acid selected from the group consisting of SEQ ID NO:4, SEQ ID NO:6, SEQ ID NO:9, and SEQ ID NO:11, or conservative substitutions of any of these polypeptide sequences or subsequences. More preferred polypeptide sequences are encoded by subsequences or full length polypeptides of SEQ ID NO:4, SEQ ID NO:6, SEQ ID NO:9, and SEQ ID NO:11.

In another embodiment, the polypeptide is an isolated human ESX polypeptide, comprising at least 8 contiguous amino acids from a polypeptide sequence encoded by a nucleic acid as set forth in SEQ ID NO: 1, where the polypeptide, when presented as an antigen, elicits the production of an antibody which specifically binds to a polypeptide encoded by a nucleic acid as set forth in SEQ ID NO: 1; and the polypeptide does not bind to antisera raised against a polypeptide encoded by a nucleic acid sequence as set forth in SEQ ID NO: 1 which has been fully immunosorbed with a polypeptide encoded by a nucleic acid sequence as set forth in SEQ ID NO: 1. Particularly preferred polypeptides are encoded by a nucleic acid as set forth in SEQ ID NO: 1.

This invention similarly provides for murine ESX polypeptides. In one embodiment the murine ESX polypeptide is an isolated ESX polypeptide comprising a subsequence of at least 5, more preferably at least 10, and more preferably at least 20, 30, 40, or even 50 contiguous amino acids of a polypeptide encoded by a nucleic acid of SEQ ID No: 15 or a murine polypeptide of FIG. 5, or conservative substitutions of any of these polypeptide sequences or subsequences. More preferred murine polypeptide sequences are encoded by subsequences or full length polypeptides of the murine amino acid sequence of FIG. 5.

In another embodiment, this invention provides for antibodies that specifically bind to human or murine ESX polypeptides or polypeptide subsequences. Preferred antibodies specifically bind to a polypeptide comprising at least 5, more preferably at least 8, most preferably at least 10 contiguous amino acids from a polypeptide encoded by a nucleic acid as set forth in SEQ ID NO: 1, where the polypeptide, when presented as an antigen, elicits the production of an antibody which specifically binds to a polypeptide encoded by a nucleic acid as set forth in SEQ ID NO: 1; and the polypeptide does not bind to antisera raised against a polypeptide encoded by a nucleic acid sequence as set forth in SEQ ID NO: 1 which has been fully immunosorbed with a polypeptide encoded by a nucleic acid sequence as set forth in SEQ ID NO: 1. Particularly preferred antibodies are elicited by polypeptides comprising 16 contiguous amino acids encoded by a nucleotide sequence as set forth in SEQ ID NO:11.

Other preferred antibodies bind to murine ESX polypeptides specifically bind to a polypeptide comprising at least 5, more preferably at least 8, most preferably at least 10 contiguous amino acids from a polypeptide encoded by a nucleic acid as set forth in SEQ ID NO: 15, or the murine polypeptide of FIG. 5, where the polypeptide, when presented as an antigen, elicits the production of an antibody which specifically binds to a polypeptide encoded by a nucleic acid as set forth in SEQ ID NO: 15 or the polypeptide of FIG. 5; and the polypeptide does not bind to antisera raised against a polypeptide encoded by a nucleic acid sequence as set forth in SEQ ID NO: 15 or the polypeptide of FIG. 5 which has been fully immunosorbed with a polypeptide encoded by a nucleic acid sequence as set forth in SEQ ID NO: 1 or the murine polypeptide of FIG. 5.

Any of the ESX antibodies can be polyclonal or monoclonal antibodies. This invention also provides for cells expressing any of the ESX (anti-ESX polypeptide) antibodies of this invention. Particularly preferred cells include, but are not limited to, hybridomas.

In still another embodiment, this invention provides for methods of detecting dysregulation of an ESX gene in an organism. The methods involve providing a biological sample of the organism; and determining whether an ESX gene in the sample is expressed at a higher level or is present at a greater copy number compared to an ESX gene in a corresponding tissue known to be healthy. Corresponding tissues are tissues that are obtained from the same or similar physiological milieu in a healthy organism (e.g., from the same tissue in an organism of the same sex, age, and point in menstrual cycle (if female)). Preferred methods detect dysregulation resulting from ESX gene amplification in cells of the sample. In one embodiment, the gene amplification is detected by comparative genomic hybridization or FISH. In another embodiment, the disregulation results from ESX gene rearrangement in cells of the sample. In particularly preferred methods, the ESX gene is at a level at least 50% greater in the biological sample than in said healthy tissue is indicative of an epithelial cancer. Particularly preferred cancers include cancers of the bladder, ovary, head, neck, and breast. In one preferred embodiment, the healthy tissue comprises normal human mammary epithelial cells. In other preferred methods, the abnormal expression of said ESX gene is indicative of an unfavorable prognosis. Still other methods further comprise selecting an appropriate treatment regime. In some of the above-described methods, the detecting can comprise detecting an ESX nucleic acid (e.g., via a hybridization assay). In others of the above-described methods, the detecting can comprise detecting an ESX polypeptide (e.g., via an immunoassay). In particularly preferred methods, the ESX polypeptide is detected using an antibody which specifically binds a polypeptide comprising at least 10 contiguous amino acids from a polypeptide encoded by a nucleic acid as set forth in SEQ ID NO: 1. In other preferred methods, the nucleic acid detected is selected from the group consisting of SEQ ID NO:4, SEQ ID NO:6, SEQ ID NO:9, and SEQ ID NO:11 or a subsequence thereof.

In another embodiment, this invention provides a method of diagnosing an epithelial cancer in a patient. This method involves contacting a nucleic acid sample from the patient with a probe which hybridizes selectively to a target polynucleotide sequence comprising a sequence, or a subsequence, selected from the group consisting of SEQ ID NO:4, SEQ ID NO:6, SEQ ID NO:9, and SEQ ID NO:11 wherein the probe is contacted with the sample under conditions in which the probe hybridizes selectively with the target polynucleotide sequence to form-a stable hybridization complex; and detecting the formation of a hybridization complex. In a preferred embodiment, the nucleic acid sample is from a patient with breast cancer. In particularly preferred methods, the nucleic acid sample is a metaphase spread or an interphase nucleus.

In another embodiment, this invention provides a method of inhibiting growth or proliferation of neoplastic cells. These methods involve administering to the cells either an toxic concentration of ESX, or an effective amount of an agent that inhibits biological activity of an ESX transcription factor. Preferred neoplastic cells comprise a cancer in an organism, while preferred agents inhibit expression of the ESX transcription factor. The method can comprise transfecting cells of the mammal with a vector expressing an antisense ESX nucleic acid. The method can involve administering to the organism a therapeutically effective dose of a composition comprising an antisense ESX nucleic acid and a pharmacological excipient. The agent can also be an antibody that specifically binds the ESX transcription factor or an inactive ESX transcription factor mutein.

In another embodiment this invention provides a transfected cell comprising a heterologous gene encoding an ESX transcription factor. The cell may comprise a transgenic non-human animal. The cell, in vivo or in vitro, can comprise a mutated ESX transcription factor gene and the animal or cell can otherwise be deficient in ESX transcription factor activity. The deficiency may be a result of a reduced level of ESX mRNA compared to an unmutated ESX gene in a similar physiological milieu. The deficiency can be a result of a mutated gene encoding an ESX polypeptide having a reduced level of biological activity compared to a wild-type ESX polypeptide. The mutated gene can comprise one or more mutations selected from the group consisting of a missense mutation, a nonsense mutation, an insertion, or a deletion.

This invention also provides methods of determining whether a gene is regulated by an ESX polypeptide. These methods involve contacting a nucleic acid comprising a 5' flanking region of said gene with an ESX polypeptide to form a nucleic acid-protein complex; treating the complex with a DNase under conditions sufficient to digest said nucleic acid at hypersensitive regions; separating the DNase-treated complex to obtain a footprint pattern; and determining whether the footprint pattern comprises a hypersensitive band flanked by two protected regions, wherein said hypersensitive band corresponding to a first guanine residue in a GGA sequence is indicative of said gene being regulated by an ESX polypeptide.

This invention also provides for pharmacological compositions and kits. The pharmacological compositions can comprise a pharmaceutically acceptable carrier and a molecule selected from the group consisting of consisting of a vector encoding an ESX nucleic acid or subsequence thereof, an ESX polypeptide or subsequence thereof, and an anti-ESX antibody. The kits can comprise a container containing a molecule selected from the group consisting of an ESX nucleic acid or subsequence thereof, an ESX polypeptide or subsequence thereof, and an anti-ESX antibody.

In another embodiment, this invention provides in methods of screening for a therapeutic lead compound. The methods involve providing a nucleic acid encoding a polypeptide of ESX exon 4 or a polypeptide sequence of ESX exon 4; (ii) contacting the compound to the nucleic acid or polypeptide sequence; and (iii) detecting binding of the compound to the nucleic acid or polypeptide sequence. Compounds that specifically bind to the exon 4 nucleic acid and/or polypeptide are expected to provide lead compounds for therapeutic evaluation and/or development. Suitable binding assays are described below and are also well known to those of skill in the art.

Similarly, in another related embodiment, this invention provides a method of identifying potential therapeutic targets for drug screening. The method involves: i) identifying a subsequence of the ESX gene or protein necessary for ESX transactivational activity; ii) performing a nucleic acid or protein database search to identify other nucleic acids having significant sequence identity with said subsequence whereby said subsequence is identified as a potential therapeutic target for drug screening. In a particularly preferred embodiment, such subsequences will be searched for among known or unknown topoisomerases, gyrases, helicases, and related DNA repair enzymes. Significant sequence identity will generally refer to statistically significant sequence identity, typically greater than about 40%, more preferably greater than about 50%, most preferably greater than about 70%, 80%, 90% or even 95%, across a window of at least about 14 amino acids, more preferably across a window of at least about 16 amino acids, and most preferably across a window of at least about 20, 25, or even 30 amino acids (or corresponding nucleotide window sizes).

Definitions

The term "antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, *Fundamental Immunology*, Third Edition, W. E. Paul, ed., Raven Press, N.Y. 1993). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

An "anti-ESX antibody" is an antibody or antibody fragment that specifically binds a polypeptide encoded by the ESX gene, cDNA, or a subsequence thereof.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay that utilizes an antibody to specifically bind an analyte. The immunoassay is characterized by the use of specific binding properties of a particular antibody to isolate, target, and/or quantify the analyte.

The terms "isolated" "purified" or "biologically pure" refer to material which is substantially or essentially free from components which normally accompany it as found in its native state.

The term "nucleic acid" refers to a deoxyribonucleotide or ribonucleotide polymer in either single- or double-stranded form, and unless otherwise limited, encompasses known analogs of natural nucleotides that can function in a similar manner as naturally occurring nucleotides.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

A "label" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, dioxigenin, or haptens and proteins for which antisera or monoclonal antibodies are available (e.g., the peptide of SEQ ID NO: 2 can be made detectable, e.g., by incorporating a radio-label into the peptide, and used to detect antibodies specifically reactive with the peptide).

As used herein a "nucleic acid probe" is defined as a nucleic acid capable of binding to a target nucleic acid of complementary sequence through one or more types of chemical bonds, usually through complementary base pairing, usually through hydrogen bond formation. As used herein, a probe may include natural (i.e. A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe" is a nucleic acid probe that is bound, either covalently, through a linker, or through ionic, van der Waals or hydrogen bonds to a label such that the presence of the probe may be detected by detecting the presence of the label bound to the probe.

The term "target nucleic acid" refers to a nucleic acid (often derived from a biological sample), to which a nucleic acid probe is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding probe directed to the target. The term target nucleic acid may refer to the specific subsequence of a larger nucleic acid to which the probe is directed or to the overall sequence (e.g., gene or mRNA) whose expression level it is desired to detect. The difference in usage will be apparent from context.

"Subsequence" refers to a sequence of nucleic acids or amino acids that comprise a part of a longer sequence of nucleic acids or amino acids (e.g., polypeptide) respectively.

The term "recombinant" when used with reference to a cell, or nucleic acid, or vector, indicates that the cell, or nucleic acid, or vector, has been modified by the introduction of a heterologous nucleic acid or the alteration of a native nucleic acid, or that the cell is derived from a cell so modified. Thus, for example, recombinant cells express genes that are not found within the native (non-recombinant) form of the cell or express native genes that are otherwise abnormally expressed, under expressed or not expressed at all.

The term "identical" in the context of two nucleic acids or polypeptide sequences refers to the residues in the two sequences which are the same when aligned for maximum correspondence. Optimal alignment of sequences for comparison can be conducted, e.g., by the local homology algorithm of Smith and Waterman (1981) *Adv. Appl. Math.* 2: 482, by the homology alignment algorithm of Needleman and Wunsch (1970) *J. Mol Biol* 48:443, by the search for similarity method of Pearson and Lipman (1988) *Proc. Nat'l. Acad. Sci. USA* 85: 2444, by computerized implementations of these algorithms (GAP, BESTFIT, FASTA, and TFASTA in the Wisconsin Genetics Software Package, Genetics Computer Group, 575 Science Dr., Madison, Wis.), or by inspection.

An additional algorithm that is suitable for determining sequence similarity is the BLAST algorithm, which is described in Altschul et al. (1990) *J. Mol. Biol.* 215: 403–410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold (Altschul et al, supra.). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA*, 89: 10915–10919) alignments (B) of 50, expectation (E) of 10, M=5, N=−4, and a comparison of both strands.

The BLAST algorithm performs a statistical analysis of the similarity between two sequences; see, e.g., Karlin and Altschul (1993) Proc. Nat'l Acad. Sci. USA 90: 5873–5787. One measure of similarity provided by the BLAST algorithm is the smallest sum probability (P(N)), which provides an indication of the probability by which a match between two nucleotide or amino acid sequences would occur by chance. For example, a nucleic acid is considered similar to an ESX nucleic acid if the smallest sum probability in a comparison of the test nucleic acid to an ESX nucleic acid is less than about 0.1, more preferably less than about 0.01, and most preferably less than about 0.001. Where the test nucleic acid encodes an ESX polypeptide, it is considered similar to a specified ESX nucleic acid if the comparison results in a smallest sum probability of less than about 0.5, and more preferably less than about 0.2.

The term "substantial identity" or "substantial similarity" in the context of a polypeptide indicates that a polypeptides comprises a sequence with at least 70% sequence identity to a reference sequence, or preferably 80%, or more preferably 85% sequence identity to the reference sequence, or most preferably 90% identity over a comparison window of about 10–20 amino acid residues. An indication that two polypeptide sequences are substantially identical is that one peptide is immunologically reactive with antibodies raised against the second peptide. Thus, a polypeptide is substantially identical to a second polypeptide, for example, where the two peptides differ only by a conservative substitution.

An indication that two nucleic acid sequences are substantially identical is that the polypeptide which the first nucleic acid encodes is immunologically cross reactive with the polypeptide encoded by the second nucleic acid.

Another indication that two nucleic acid sequences are substantially identical is that the two molecules hybridize to each other under stringent conditions.

"Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

The phrase "hybridizing specifically to", refers to the binding, duplexing, or hybridizing of a molecule only to a particular nucleotide sequence under stringent conditions when that sequence is present in a complex mixture (e.g., total cellular) DNA or RNA. The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH, and nucleic acid concentration) at which 50% of the probes complementary to the target sequence hybridize to the target sequence at equilibrium. (As the target sequences are generally present in excess, at $T_m$, 50% of the probes are occupied at equilibrium). Typically, stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60EC for long probes (e.g., greater than 50 nucleotides). Stringent conditions may also be achieved with the addition of destabilizing agents such as formamide.

The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular-protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity. For determination of specific binding of an anti-ESX antibody, an immunoprecipitation assay is preferred. Under appropriate conditions, an antibody that specifically binds to an ESX polypeptide will immunoprecipitate ESX, but not other ETS transcription factors.

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) *Proteins* W. H. Freeman and Company. One of skill in the art will appreciate that the above-identified substitutions are not the only possible conservative substitutions. For example, one may regard all charged amino acids as conservative substitutions for each other whether they are positive or negative (see, e.g., FIGS. 2b, 2c, and 2d). In addition, individual substitutions, deletions or additions which alter, add or delete a single amino acid or a small percentage of amino acids in an encoded sequence are also "conservatively modified variations".

The terms human "esx" or human "ESX gene or cDNA" are used interchangeably to refer to the human esx gene, which is a transcription factor gene that is also involved in the etiology of cancers, for example, epithelial cancers. The esx gene is determined to be a member of the ETS gene family by significant homology between the ESX DNA binding domain and the DNA binding domain of other members of the ETS family. ESX, however, is distinct from previously known ETS genes because of 5 non-conservative substitutions in the ETS consensus sequence. Nevertheless, ESX is still recognized to belong to the ETS family because ESX contains 27 identical amino acid residues among the 38 recognized consensus residues making up the ETS DNA binding domain (i.e., greater than 50% sequence identity, more preferably greater than 60% sequence identity and most preferably greater than 70% sequence identity in the ETS consensus sequence). Similarly the terms mouse or murine ESX genes or cDNAs refer to the mouse or murine ESX genes or cDNAs respectively.

A "gene product", as used herein, refers to a nucleic acid whose presence, absence, quantity, or nucleic acid sequence is indicative of a presence, absence, quantity, or nucleic acid composition of the gene. Gene products thus include, but are not limited to, an mRNA transcript, a cDNA reverse transcribed from an mRNA, an RNA transcribed from that cDNA, a DNA amplified from the cDNA, an RNA transcribed from the amplified DNA or subsequences of any of these nucleic acids. Polypeptides expressed by the gene or subsequences thereof are also gene products. The particular type of gene product will be evident from the context of the usage of the term.

An "abnormal esx gene or cDNA" refers to an esx gene or cDNA that encodes an increased or decreased amount of ESX polypeptide, a non-functional ESX polypeptide, or an ESX polypeptide of substantially reduced functionality. Animal cells having non-functional, or reduced functionality, ESX polypeptides are characterized by a decrease in ESX-mediated transcriptional regulation. In a cancer cell, this relaxation of ESX-mediated regulation can result in a decrease in neoplastic cell proliferation. Similarly, "abnormal ESX gene product" refers to a nucleic acid encoding a non-functional or reduced functionality ESX polypeptide or the non-functional or reduced functionality ESX polypeptide itself. Abnormal esx genes or gene products include, for example, esx genes or subsequences altered by mutations (e.g. insertions, deletions, point mutations, etc.), splicing errors, premature termination codons, missing initiators, etc. Abnormal ESX polypeptides include polypeptides expressed by abnormal esx genes or nucleic acid gene products or subsequences thereof. Abnormal expression of esx genes includes underexpression (as compared to the "normal" healthy population) of ESX, e.g., through partial or complete inactivation, haploinsufficiency, etc.

The terms "rodent" and "rodents" refer to all members of the phylogenetic order Rodentia including any and all progeny of all future generations derived therefrom.

The term "murine" refers to any and all members of the family Muridae, including rats and mice.

A "therapeutic lead compound" refers to a compound that has a particular characteristic activity, e.g., an activity that is therapeutically useful. While the compound itself may not be suitable a therapeutic the compound provides a basis or starting point for the creation and/or screening of analogues for similar desired activity (e.g., for ESX modulatory activity).

BRIEF DESCRIPTION OF THE DRAWINGS

FIG. 1 shows the nucleotide (SEQ ID NO:1) and deduced amino acid (SEQ ID NO:2) sequences of a human ESX cDNA.

FIGS. 2a through 2e show the amino acid sequence of the human ESX polypeptide and the domain homologies of the ESX polypeptide as compared to other members of the ETS transcription factor family. FIG. 2a shows the amino acid sequence corresponding to the longest open reading frame in the human ESX cDNA (SEQ ID NO:2). Highlighted regions (boxed, bold font) are homologous to domains of other ETS transcription factors; these include the A-region/Pointed domain (amino acids 64–103), the serine-rich box (amino acids 188–238), and the ETS DNA binding domain (amino acids 274–354). Four regions that are not homologous to other Ets transcription factor domains are unboxed. FIG. 2b presents a comparison of the A-region/Pointed domain of ESX (SEQ ID NO: 17) to that encoded by the human PC ETS-1 gene (SEQ ID NO: 18). Consensus residues most highly conserved among Ets family members are shown (Lautenberger et al. (1992) Oncogene 7: 1713–1719. Conservative substitutions are indicated by (+). FIG. 2c shows the similarity between the ESX serine box (SEQ ID NO:19) and that of SOX4 (SEQ ID NO:20). A portion of the ESX serine box (SEQ ID NO:21) is shown in a helical wheel model to demonstrate clustering of serine residues opposite a hydrophobic helical face (boxed residues). FIG. 2d shows the amino acid identity and similarity within the ETS DNA binding domain of the two related subfamily members, ESX (SEQ ID NO:22) and Elf-1 (SEQ ID NO: 23). Consensus residues in this domain are the most highly conserved among all Ets family members (Janknecht and Nordheim (1993) Biochem. Biophys. Acta. 1155: 346–356). Conservative (•) and non-conservative (*) substitutions found in ESX relative to the consensus residues (SEQ ID NO:24–29) and their locations within known structural components of the ETS domain are shown (Wemer et al. (1995) Cell 83: 761–771; Kodandapani et al. (1996) Nature 380: 457–460). FIG. 2e illustrates the human ESX protein sequence (SEQ ID NO:2) showing the residues encoded by exon 4 (bold), the residues conserved in all Topo-I proteins (•) the Topo-I homologous fragment (↓) and the Lysine$^{145}$ critical for transactivation (circled and bolded K).

FIG. 4 shows the human ESX (hESX) (cDNA=SEQ ID NO:1; amino acid=SEQ ID NO:2) exon/intron junctions. The bold sequences contain the "tranactivating domain" as mapped by GAL4 fusion studies FIG. 5 shows the mouse ESX (mESX) (SEQ ID NO:16) and human ESX (hESX) (SEQ ID NO:2) primary structure and domain homologies.

FIG. 8a shows specific DNA-binding of full-length (42 kDa) recombinantly expressed ESX to an oligonucleotide sequence (TA5) containing the Ets responsive element (GGAA) from the HER2/neu promoter. Five different competing unlabeled (cold) oligonucleotides containing specific mutations in the wild-type (WT) TA5 (SEQ ID NO:32) sequence, m1–m5 (SEQ ID NOs:33–37) were added at 50-fold molar excess; gel lanes containing the excess cold competitors are labeled. FIG. 8b shows a DNase-I hypersensitivity site and footprint produced by ESX on the antisense strand of an Ets response element in the HER2/neu promoter. The antisense strand sequence as shown (~40 bp to ~26 bp upstream of major transcriptional start site in HER2/neu promoter) is marked with asterisk at the hypersensitivity site within Ets response element (GGAA on sense strand). FIGS. 8c and 8d show the induction of CAT activity from two different ETS-responsive reporter constructs (p3TA5-BLCAT5, pHER2-CAT) in COS cells cotransfected with an ESX expression plasmid (pcDNAI-ESX). Mutant reporter plasmids (p3TA5P-BLCAT5, pHER2m-CAT) are identical to their normal counterparts except for alterations in the Ets response element within the TA5 sequence (GGAA to GAGA and GGAA to TTAA, respectively). FIG. 8e shows metaphase mapping of ESX by fluorescence in situ hybridization (FISH) to human chromosome locus 1q32 in normal human lymphocytes, and aneuploid ESX copy number in human breast cancer cells. Inset shows the localization of ESX (green) to 1q32 based on DAPI banding of metaphase chromosome 1; interphase FISH reveals a mean of 5–6 copies of ESX (green) per SK-BR-3 cell (lower right panel) and a mean of 4 copies of ESX per BT-474 cell (upper right panel) relative to a reference probe for 1q1 (pUC177, red), which indicates comparable levels of chromosome 1q aneusomy in these breast cancer cell lines.

FIG. 9a shows commercially obtained membranes (Clontech) containing poly A-RNA from normal human tissues and peripheral blood leukocytes (PBL) probed to reveal the major 2.2 kb ESX transcript bands and the minor 4.1 kb ESX bands (kb RNA size markers indicated on left). FIG. 9b shows the amount of ESX transcript in total cellular RNA extracted from normal human mammary epithelial cells (HMEC), immortalized/non-transformed mammary cell lines (HBL100, MCF10A) and HER2/neu-positive (BT-474, SK-BR-3, ZR-75-1) and HER2/neu-negative (MCF-7, MDA-231) human breast cancer cell lines. FIG. 9c shows the immediate early induction of ESX mRNA upon treatment of SK-BR-3 cells with the purified growth factor, heregulin-b1$_{1-244}$ (HRG) (Holmes et al. (1992) Science 256: 1205–1210). Lane 1, no HRG treatment; lanes 2 to 6, treatment with 1 nM HRG for 15, 30, 60, 120, and 180 min. RNA lane loading was controlled for by probing the same blot for glyceraldehyde 3-phosphate dehydrogenase (GAPDH) expression.

FIG. 11 illustrates mapping of the hESX activation domain. The varying hESX deletion constructs and their transactivation activity is shown.

DETAILED DESCRIPTION

Figure 2C:
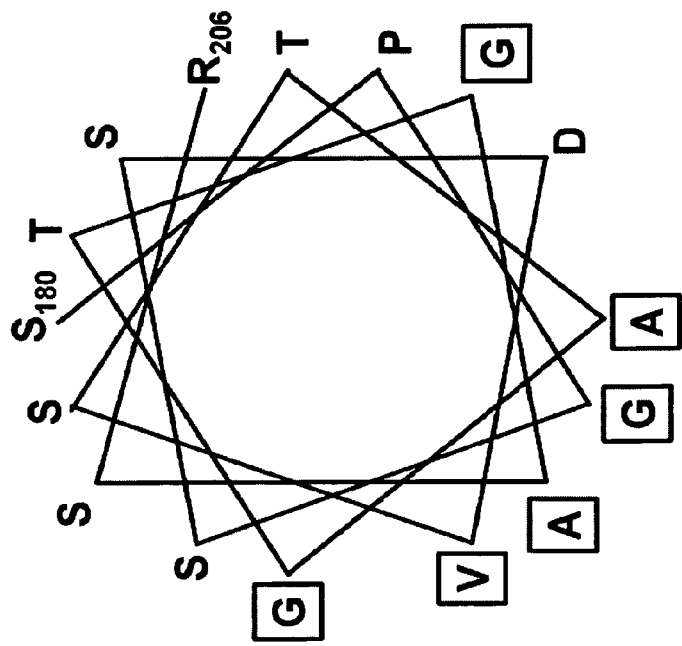

This invention pertains to the discovery of a transcription factor associated with the etiology of cancers, including epithelial cancers. This transcription factor, referred to as ESX (for epithelial-restricted with serine box), is located at chromosome 1 q32 in a region known to be amplified in 50% of early breast cancers. ESX is heregulin-inducible and overexpressed in HER2/neu activated breast cancer cells. Tissue hybridization suggests that ESX becomes overexpressed at an early stage of human breast cancer development known as ductal carcinoma in situ (DCIS).

ESX is a member of the ETS transcription factor family. ETS transcription factors regulate stage- and tissue-specific gene programs in fetal development and are known to be overexpressed or rearranged in a variety of vertebrate and human malignancies. ETS target genes include growth factor receptors (e.g., erbB2) and extracellular matrix proteases (e.g., MMPs, uPA) important in both development and tumorigenesis.

The human ESX identified herein is an epithelium-restricted ETS factor upregulated in erbB2-overexpressing early breast tumors (DCIS) and breast cancer cell lines, and in response to growth factors like heregulin.

In addition, this invention provides murine ESX genes and cDNA. Comparison of mouse and human ESX sequences reveals ~350 bp proximal promoter region with greater than 80% homology and conserved ETS, AP-2, SP1, USF, Oct, and NF-κB response elements which are believed to regulate ESX induction.

Induction of ESX mRNA occurs progressively during fetal mouse development from day 7, when differentiation of fetal epithelial tissue is known to begin. IN adult mouse mammary glands, ESX expression increases during first pregnancy in association with ductal budding, branching, and the emergence of lobuloalveolar structures. Cultured HC11 mammary epithelial cells hormonally stimulated to produce milk proteins show no induction of ESX expression; in vivo, lactating mammary glands show less ESX expression that late pregnancy glands. In contrast, weaning induces a dramatic increase in ESX in association with glandular involution, indicating that ESX has a primary role in directing mammary gland remodeling and the early differentiation of ductal epithelium.

I. Uses of the ESX cDNA.

As indicated above, the ESX gene of this invention is a transcription factor gene. Defects in the expression of this gene are associated the onset of various cancers (e.g., cancers of the ovary, bladder, head and neck, and colon, etc.), particularly with epithelial cancers, including breast cancer among others.

Without being bound by a particular theory, it is believed that the correlation of ESX expression with erbB2 upregulation in cancers results from erbB2 kinase upregulation of the ESX promoter leading to increased ESX transcription which appears important for regulating gene programs necessary for enhanced tumor cell invasion and metastasis.

Clearly detection of dysregulated (e.g., through over- or under-expression, amplification or deletion or mutation) ESX gene expression is of clinical value. The presence of an ESX gene, cDNA, protein, or subsequence of the gene, cDNA, or protein in a biological sample is useful, e.g., as a marker to asses in vivo and/or in situ RNA transcription and/or translation, in cancer diagnostics (as in the detection or verification of carcinoma), in prophylaxis for cancer, in particular epithelial cancers, as an indication of a heritable predilection for such cancers, or in DNA forensic analysis such as DNA fingerprinting.

In addition, the ESX gene expression is also implicated in the development of many types of epithelial cells. Diseases of these tissues other than malignancies (e.g., skin disorders, gut and lung disorders, etc.) are believed to be amenable by the same strategies used for a malignancy associated with disordered ESX expression.

Full-length ESX cDNA, individual exons, or subsequences thereof are also useful as probes (particularly when labeled) for the detection of the presence or absence and/or quantitation of normal or abnormal (e.g., truncated or mutated) ESX DNA or RNA in a biological sample. The labeled probes can also be useful as in fluorescent karyotyping analysis as markers of the ESX gene. Because the ESX cDNA or subsequences thereof is shown herein to map to human chromosome 1q32, one of skill can use the gene, cDNA, or subsequences, as a probe to assess whether there are any gross chromosomal abnormalities in this region of chromosome 1. This is useful, for instance, in in utero screening of a fetus to monitor for the presence of chromosomal abnormalities in particular for a predilection of epithelial or other carcinomas.

Similarly, the proteins encoded by the ESX cDNA can be used as diagnostic markers for epithelial cancers, including breast cancer. The proteins or subsequences thereof can also be used as antigens for raising anti-ESX protein antibodies. The antibodies are useful for immunoassays for the detection of normal or abnormal expression of ESX proteins, and for the isolation of ESX polypeptides (as with affinity chromatography).

In addition, the ESX promoters, genes, cDNAs, and polypeptides provided herein can be used to screen for agents that modulate (e.g., up-regulate or down-regulate) ESX gene expression, or ESX polypeptide activity.

Vectors encoding the ESX proteins are useful for expressing those proteins to provide immunogens for antibody production. Vectors encoding the ESX proteins are also useful for transforming cells in vitro or in vivo to express ESX proteins. In vivo transformation of cells to express heterologous ESX genes can be used to offset deficient expression of the ESX protein; alternatively, expression of antisense or mutated ESX genes can interfere with undesirable ESX biological activity.

Cells and/or tissues expressing the ESX gene may be used to monitor expression levels of ESX polypeptides in a wide variety of contexts. For example, where the effects of a drug on ESX expression is to be determined the drug will be administered to the transformed (to express ESX) organism, tissue, or cell. Expression levels, or expression products will be assayed as described below and the results compared results from to organisms, tissues, or cells similarly treated, but without the drug being tested.

II. The ESX Gene and cDNA.

A) The Human ESX Gene.

FIG. 1 provides both nucleic acid (SEQ ID NO:1) and polypeptide (SEQ ID NO:2) sequences for the human ESX cDNA of this invention. The sequence of human ESX consists of an open reading frame of 1113 nucleotides; an additional 161 and 703 nucleotides of 5'- and 3'-flanking sequence are presented in SEQ ID NO: 3. The open reading frame of human ESX cDNA encodes for a putative protein of 371 amino acids and a predicted molecular weight of 41428 Daltons.

B) The Murine ESX gene.

Figure 3:
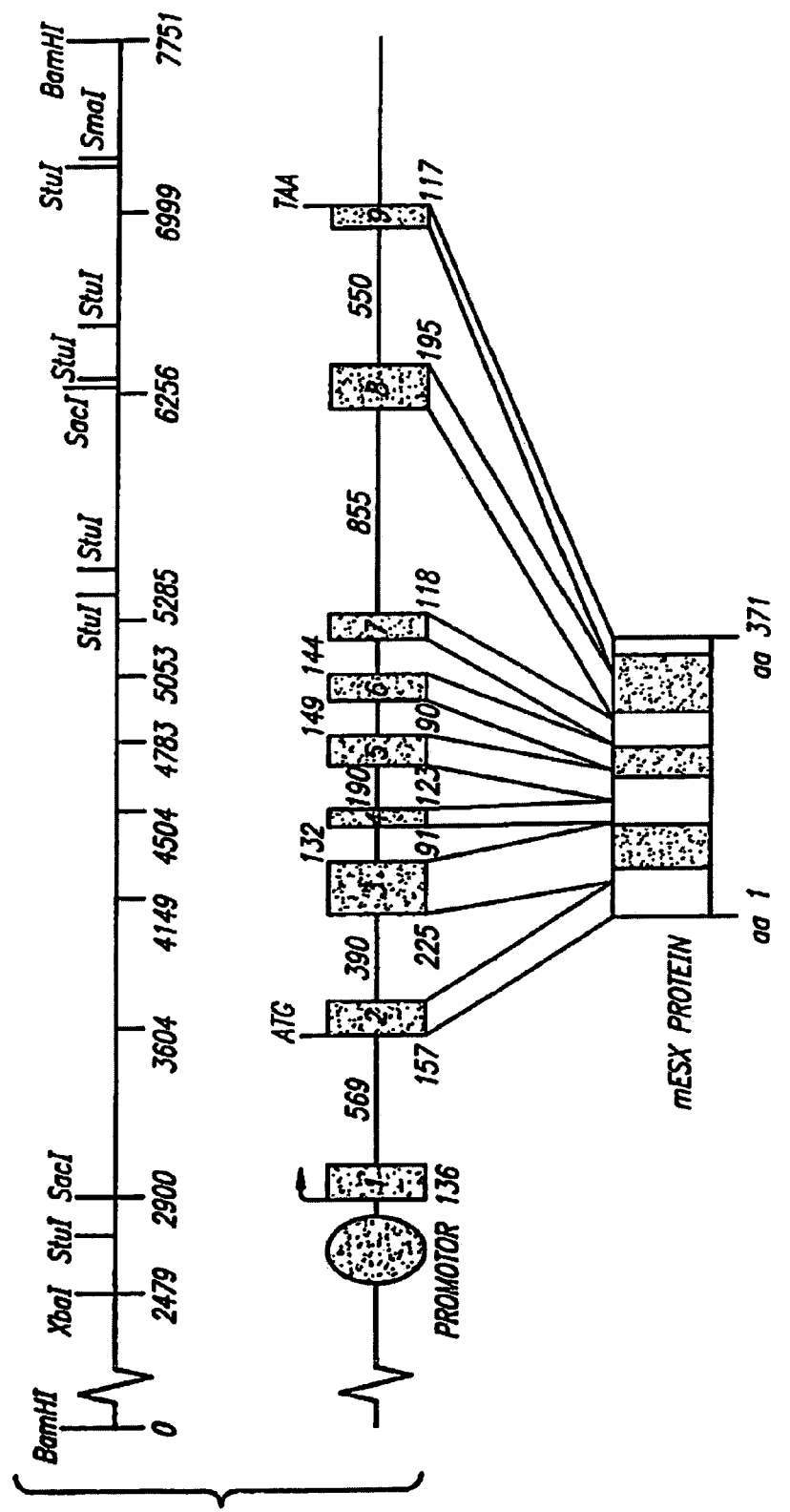
FIG. 3 Illustrates the murine ESX (mESX) genomic organization and gene product.

A 7.8 kb mESX genomic clone was isolated that contains ~2.9 kb of promoter upstream of ~4.9 kb of DNA incorporating at least 9 exons (see FIG. 3 and SEQ ID NO: 15). These exons specify a full-length transcript of about 2 kb, with exons 2–9 encoding the 371 amino acid mESX protein. Comparison of the mouse and human ESX sequences revealed the following structural and/or functional domains within a 42 kDa ESX protein conserved between mouse and human: an exon 3 encoded POINTED/A-region, found in a small subset of all ETS genes; an amphiphathic helix and serine-rich box encoded by exons 5 and 6; a nucleoplamin-type nuclear targeting sequence encoded by exon 7, and a helix-turn-helix ETS DNA binding domain encoded by exons 8 and 9.

The proximal promoter region of mESX (350 bp upstream of the transcriptional start site, see FIG. 6) is 83% homologous to the hESX promoter. Conserved putative response elements within this region include ETS, AP-2, SP1, USF, Oct, and NF-κB binding sites which are believed to regulate ESX induction. A conserved CCAAT box lies about 80 bp upstream of the pyrimidine rich Inr element which specifies ESX transcript initiation. Unlike hESX, mESX lacks a TATA box.

B) Isolation of cDNA and/or Probes.

The nucleic acids (e.g., ESX cDNA, or subsequences (probes)) of the present invention are cloned, or amplified by in vitro methods, such as the polymerase chain reaction (PCR), the ligase chain reaction (LCR), the transcription-based amplification system (TAS), the self-sustained sequence replication system (SSR). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3: 81–94; Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science,* 241: 1077–1080; Van Brunt (1990) *Biotechnology,* 8: 291–294; Wu and Wallace, (1989) *Gene,* 4: 560; and Barringer et al. (1990) *Gene,* 89: 117.

In one preferred embodiment, the human ESX cDNA can be isolated by routine cloning methods. The cDNA sequence provided in SEQ ID NO: 1 can be used to provide probes that specifically hybridize to the ESX gene, in a genomic DNA sample, or to the ESX mRNA, in a total RNA sample (e.g., in a Southern blot). Once the target ESX nucleic acid is identified (e.g., in a Southern blot), it can be isolated according to standard methods known to those of skill in the art (see, e.g., Sambrook et al. (1989) *Molecular Cloning: A Laboratory Manual*, 2nd Ed., Vols. 1–3, Cold Spring Harbor Laboratory; Berger and Kimmel (1987) *Methods in Enzymology, Vol.* 152: *Guide to Molecular Cloning Techniques*, San Diego: Academic Press, Inc.; or Ausubel et al. (1987) *Current Protocols in Molecular Biology*, Greene Publishing and Wiley-Interscience, New York). Methods of screening human cDNA libraries for the ESX gene are provided in Example 1.

In another preferred embodiment, the human ESX cDNA can be isolated by amplification methods such as polymerase chain reaction (PCR). In a preferred embodiment, the ESX sequence is amplified from a cDNA sample (e.g., double stranded placental cDNA (Clontech)) using the primers 5'ESX-DBD, 5'-CCGGGACATCCTCA TCCACCC-3' (SEQ ID No: 13)) and 3' ESX-DBD (5'-GTACCTCATG-GCCCGGCTCAG-3' (SEQ ID NO:14)). Preferred amplification conditions include 10× PCR buffer (500 mM KCl, 100 mM Tris, pH 8.3 at room temperature, 15 mM $MgCl_2$, 0.1% gelatin) with the amplification run for about 34 cycles at 94° C. for 30 sec, 58° C. for 30 sec and 72° C. for 60 sec.

Similarly, using the nucleic acid sequence provided herein (e.g. SEQ ID NO: 15), one of ordinary skill can routinely isolate the mouse ESX gene, mRNA or cDNA. However, in a preferred embodiment, the mouse ESX sequence is amplified from a nucleic acid sample (e.g., gDNA or cDNA) using that primers readily derived from the sequence listings provided herein. Suitable primers include, but are not limited to primers (e.g., 20 mers) corresponding to the 5' and 3' termini of the murine ESX cDNA as described above.

C) Labeling of Nucleic Acid Probes.

Where the ESX cDNA or its subsequences are to be used as nucleic acid probes, it is often desirable to label the nucleic acids with detectable labels. The labels may be incorporated by any of a number of means well known to those of skill in the art. However, in a preferred embodiment, the label is simultaneously incorporated during the amplification step in the preparation of the sample nucleic acids. Thus, for example, polymerase chain reaction (PCR) with labeled primers or labeled nucleotides will provide a labeled amplification product. In another preferred embodiment, transcription amplification using a labeled nucleotide (e.g. fluorescein-labeled UTP and/or CTP) incorporates a label into the transcribed nucleic acids.

Alternatively, a label may be added directly to an original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3H$, $125I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

III. Antibodies to ESX Polypeptide(s).

Antibodies are raised to the ESX polypeptides of the present invention, including individual, allelic, strain, or species variants, and fragments thereof, both in their naturally occurring (full-length) forms and in recombinant forms. Additionally, antibodies are raised to these polypeptides in either their native configurations or in non-native configurations. Anti-idiotypic antibodies can also be generated. Many methods of making antibodies are known to persons of skill. The following discussion is presented as a general overview of the techniques available; however, one of skill will recognize that many variations upon the following methods are known.

A) Antibody Production.

A number of immunogens are used to produce antibodies specifically reactive with ESX polypeptides. Recombinant or synthetic polypeptides of 10 amino acids in length, or greater, selected from amino acid sub-sequences of SEQ ID NO:1 are the preferred polypeptide immunogen (antigen) for the production of monoclonal or polyclonal antibodies. In one class of preferred embodiments, an immunogenic peptide conjugate is also included as an immunogen. Naturally occurring polypeptides are also used either in pure or impure form.

Recombinant polypeptides are expressed in eukaryotic or prokaryotic cells (as described below) and purified using standard techniques. The polypeptide, or a synthetic version thereof, is then injected into an animal capable of producing antibodies. Either monoclonal or polyclonal antibodies can be generated for subsequent use in immunoassays to measure the presence and quantity of the polypeptide.

Methods of producing polyclonal antibodies are known to those of skill in the art. In brief, an immunogen (antigen), preferably a purified polypeptide, a polypeptide coupled to an appropriate carrier (e.g., GST, keyhole limpet hemocyanin, etc.), or a polypeptide incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the polypeptide is performed where desired (see, e.g., Coligan (1991) *Current Protocols in Immunology* Wiley/Greene, NY; and Harlow and Lane (1989) *Antibodies: A Laboratory Manual*, Cold Spring Harbor Press, NY).

Antibodies, including binding fragments and single chain recombinant versions thereof, against predetermined fragments of ESX polypeptides are raised by immunizing animals, e.g., with conjugates of the fragments with carrier proteins as described above. Typically, the immunogen of interest is a peptide of at least about 5 amino acids, more typically the peptide is 10 amino acids in length, preferably, the fragment is 15 amino acids in length and more preferably the fragment is 20 amino acids in length or greater. The peptides are typically coupled to a carrier protein (e.g., as a fusion protein), or are recombinantly expressed in an immunization vector. Antigenic determinants on peptides to which antibodies bind are typically 3 to 10 amino acids in length.

One particularly preferred immunogen is illustrated in the Example 1. In this example, a peptide fragment consisting of the sixteen carboxy-terminal amino acids of ESX was used as an ESX antigen in rabbits. An amino-terminal cysteine was introduced to allow coupling of the peptide to a carrier protein (KLH). Anti-ESX antibodies were obtained by affinity purification of total IgG from immunized rabbits using an affinity column to which the ESX carboxyl terminal peptide fragment was bound.

Monoclonal antibodies are prepared from cells secreting the desired antibody. These antibodies are screened for binding to normal or modified polypeptides, or screened for agonistic or antagonistic activity, e.g., activity mediated through an ESX protein. Specific monoclonal and polyclonal antibodies will usually bind with a $K_d$ of at least about 0.1 mM, more usually at least about 50 mM, and most preferably at least about 1 mM or better.

In some instances, it is desirable to prepare monoclonal antibodies from various mammalian hosts, such as mice, rodents, primates, humans, etc. Description of techniques for preparing such monoclonal antibodies are found in, e.g., Stites et al. (eds.) *Basic and Clinical Immunology* (4th ed.) Lange Medical Publications, Los Altos, Calif., and references cited therein; Harlow and Lane, supra; Goding (1986) *Monoclonal Antibodies: Principles and Practice* (2d ed.) Academic Press, New York, N.Y.; and Kohler and Milstein (1975) *Nature* 256: 495–497. Summarized briefly, this method proceeds by injecting an animal with an immunogen. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate (preferably mammalian) host. The polypeptides and antibodies of the present invention are used with or without modification, and include chimeric antibodies such as humanized murine antibodies.

Other suitable techniques involve selection of libraries of recombinant antibodies in phage or similar vectors (see, e.g., Huse et al. (1989) *Science* 246: 1275–1281; and Ward, et al. (1989) *Nature* 341: 544–546; and Vaughan et al. (1996) *Nature Biotechnology*, 14: 309–314).

Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced (see, e.g.; Cabilly, U.S.

Pat. No. 4,816,567; and Queen et al. (1989) *Proc. Nat'l Acad. Sci. USA* 86: 10029–10033.

The antibodies of this invention are also used for affinity chromatography in isolating ESX polypeptides. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified ESX polypeptides are released.

The antibodies can be used to screen expression libraries for particular expression products such as normal or abnormal human ESX protein. Usually the antibodies in such a procedure are labeled with a moiety allowing easy detection of presence of antigen by antibody binding.

Antibodies raised against ESX polypeptides can also be used to raise anti-idiotypic antibodies. These are useful for detecting or diagnosing various pathological conditions related to the presence of the respective antigens.

B) Human or Humanized (Chimeric) Antibody Production.

The anti-ESX antibodies of this invention can also be administered to an organism (e.g., a human patient) for therapeutic purposes (e.g., to block the action an ESX polypeptide or as targeting molecules when conjugated or fused to effector molecules such as labels, cytotoxins, enzymes, growth factors, drugs, etc.). Antibodies administered to an organism other than the species in which they are raised are often immunogenic. Thus, for example, murine antibodies administered to a human often induce an immunologic response against the antibody (e.g., the human anti-mouse antibody (HAMA) response) on multiple administrations. The immunogenic properties of the antibody are reduced by altering portions, or all, of the antibody into characteristically human sequences thereby producing chimeric or human antibodies, respectively.

i) Humanized (Chimeric) Antibodies.

Humanized (chimeric) antibodies are immunoglobulin molecules comprising a human and non-human portion. More specifically, the antigen combining region (or variable region) of a humanized chimeric antibody is derived from a non-human source (e.g., murine) and the constant region of the chimeric antibody (which confers biological effector function to the immunoglobulin) is derived from a human source. The humanized chimeric antibody should have the antigen binding (e.g., anti-ESX polypeptide) specificity of the non-human antibody molecule and the effector function conferred by the human antibody molecule. A large number of methods of generating chimeric antibodies are well known to those of skill in the art (see, e.g., U.S. Pat. Nos. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369).

In general, the procedures used to produce these chimeric antibodies consist of the following steps (the order of some steps may be interchanged): (a) identifying and cloning the correct gene segment encoding the antigen binding portion of the antibody molecule; this gene segment (known as the VDJ, variable, diversity and joining regions for heavy chains or VJ, variable, joining regions for light chains (or simply as the V or Variable region) may be in either the cDNA or genomic form; (b) cloning the gene segments encoding the constant region or desired part thereof, (c) ligating the variable region with the constant region so that the complete chimeric antibody is encoded in a transcribable and translatable form; (d) ligating this construct into a vector containing a selectable marker and gene control regions such as promoters, enhancers and poly(A) addition signals; (e) amplifying this construct in a host cell (e.g., bacteria); (f) introducing the DNA into eukaryotic cells (transfection) most often mammalian lymphocytes;

Antibodies of several distinct antigen binding specificities have been manipulated by these protocols to produce chimeric proteins (e.g., anti-TNP: Boulianne et al. (1984) *Nature,* 312: 643; and anti-tumor antigens: Sahagan et al. (1986) *J. Immunol.,* 137: 1066). Likewise several different effector functions have been achieved by linking new sequences to those encoding the antigen binding region. Some of these include enzymes (Neuberger et al. (1984) *Nature* 312: 604), immunoglobulin constant regions from another species and constant regions of another immunoglobulin chain (Sharon et al. (1984) *Nature* 309: 364; Tan et al., (1985) *J. Immunol.* 135: 3565–3567).

In one preferred embodiment, recombinant DNA vector is used to transfect a cell line that produces an anti-ESX antibody. The novel recombinant DNA vector contains a "replacement gene" to replace all or a portion of the gene encoding the immunoglobulin constant region in the cell line (e.g., a replacement gene may encode all or a portion of a constant region of a human immunoglobulin, a specific immunoglobulin class, or an enzyme, a toxin, a biologically active peptide, a growth factor, inhibitor, or a linker peptide to facilitate conjugation to a drug, toxin, or other molecule, etc.), and a "target sequence" which allows for targeted homologous recombination with immunoglobulin sequences within the antibody producing cell.

In another embodiment, a recombinant DNA vector is used to transfect a cell line that produces an antibody having a desired effector function, (e.g., a constant region of a human immunoglobulin) in which case, the replacement gene contained in the recombinant vector may encode all or a portion of a region of an anti-ESX antibody and the target sequence contained in the recombinant vector allows for homologous recombination and targeted gene modification within the antibody producing cell. In either embodiment, when only a portion of the variable or constant region is replaced, the resulting chimeric antibody may define the same antigen and/or have the same effector function yet be altered or improved so that the chimeric antibody may demonstrate a greater antigen specificity, greater affinity binding constant, increased effector function, or increased secretion and production by the transfected antibody producing cell line, etc.

Regardless of the embodiment practiced, the processes of selection for integrated DNA (via a selectable marker), screening for chimeric antibody production, and cell cloning, can be used to obtain a clone of cells producing the chimeric antibody. Thus, a piece of DNA which encodes a modification for a monoclonal antibody can be targeted directly to the site of the expressed immunoglobulin gene within a B-cell or hybridoma cell line. DNA constructs for any particular modification may be used to alter the protein product of any monoclonal cell line or hybridoma. Such a procedure circumvents the costly and time consuming task of cloning both heavy and light chain variable region genes from each B-cell clone expressing a useful antigen specificity. In addition to circumventing the process of cloning variable region genes, the level of expression of chimeric antibody should be higher when the gene is at its natural chromosomal location rather than at a random position. Detailed methods for preparation of chimeric (humanized) antibodies can be found in U.S. Pat. No. 5,482,856.

ii) Human Antibodies.

In another embodiment, this invention provides for fully human anti-ESX antibodies. Human antibodies consist entirely of characteristically human polypeptide sequences. The human anti-ESX antibodies of this invention can be produced in using a wide variety of methods (see, e.g., Larrick et al., U.S. Pat. No. 5,001,065, for review).

In one preferred embodiment, the human anti-ESX antibodies of the present invention are usually produced initially in trioma cells. Genes encoding the antibodies are then cloned and expressed in other cells, particularly, nonhuman mammalian cells.

The general approach for producing human antibodies by trioma technology has been described by Ostberg et al. (1983), *Hybridoma* 2: 361–367, Ostberg, U.S. Pat. No. 4,634,664, and Engelman et al., U.S. Pat. No. 4,634,666. The antibody-producing cell lines obtained by this method are called triomas because they are descended from three cells; two human and one mouse. Triomas have been found to produce antibody more stably than ordinary hybridomas made from human cells.

Preparation of trioma cells requires an initial fusion of a mouse myeloma cell line with unimmunized human peripheral B lymphocytes. This fusion generates a xenogenic hybrid cell containing both human and mouse chromosomes (see, Engelman, supra.). Xenogenic cells that have lost the capacity to secrete antibodies are selected. Preferably, a xenogenic cell is selected that is resistant to 8-azaguanine. Cells possessing resistance to 8-azaguanine are unable to propagate on hypoxanthine-aminopterin-thymidine (HAT) or azaserine-hypoxanthine (AH) media.

The capacity to secrete antibodies is conferred by a further fusion between the xenogenic cell and B-lymphocytes immunized against an ESX polypeptide or an epitope thereof. The B-lymphocytes are obtained from the spleen, blood or lymph nodes of human donor. If antibodies against a specific antigen or epitope are desired, it is preferable to use that antigen or epitope thereof as the immunogen rather than ESX polypeptide. Alternatively, B-lymphocytes are obtained from an unimmunized individual and stimulated with an ESX polypeptide, or a epitope thereof, in vitro. In a further variation, B-lymphocytes are obtained from an infected, or otherwise immunized individual, and then hyperimmunized by exposure to an ESX polypeptide for about seven to fourteen days, in vitro.

The immunized B-lymphocytes prepared by one of the above procedures are fused with a xenogenic hybrid cell by well known methods. For example, the cells are treated with 40–50% polyethylene glycol of MW 1000–4000, at about 37° C. for about 5–10 min. Cells are separated from the fusion mixture and propagated in media selective for the desired hybrids. When the xenogenic hybrid cell is resistant to 8-azaguanine, immortalized trioma cells are conveniently selected by successive passage of cells on HAT or AH medium. Other selective procedures are, of course, possible depending on the nature of the cells used in fusion. Clones secreting antibodies having the required binding specificity are identified by assaying the trioma culture medium for the ability to bind to an ESX polypeptide or an epitope thereof. Triomas producing human antibodies having the desired specificity are subcloned by the limiting dilution technique and grown in vitro in culture medium, or are injected into selected host animals and grown in vivo.

The trioma cell lines obtained are then tested for the ability to bind an ESX polypeptide or an epitope thereof. Antibodies are separated from the resulting culture medium or body fluids by conventional antibody-fractionation procedures, such as ammonium sulfate precipitation, DEAE cellulose chromatography and affinity chromatography.

Although triomas are genetically stable they do not produce antibodies at very high levels. Expression levels can be increased by cloning antibody genes from the trioma into one or more expression vectors, and transforming the vector into a cell line such as the cell lines typically used for expression of recombinant or humanized immunoglobulins. As well as increasing yield of antibody, this strategy offers the additional advantage that immunoglobulins are obtained from a cell line that does not have a human component, and does not therefore need to be subjected to the especially extensive viral screening required for human cell lines.

The genes encoding the heavy and light chains of immunoglobulins secreted by trioma cell lines are cloned according to methods, including the polymerase chain reaction, known in the art (see, e.g., Sambrook et al., *Molecular Cloning: A Laboratory Manual*, 2nd ed., Cold Spring Harbor, N.Y., 1989; Berger & Kimmel, *Methods in Enzymology, VoL* 152: *Guide to Molecular Cloning Techniques*, Academic Press, Inc., San Diego, Calif., 1987; Co et al. (1992) *J. Immunol.*, 148: 1149). For example, genes encoding heavy and light chains are cloned from a trioma's genomic DNA or cDNA produced by reverse transcription of the trioma's RNA. Cloning is accomplished by conventional techniques including the use of PCR primers that hybridize to the sequences flanking or overlapping the genes, or segments of genes, to be cloned.

Typically, recombinant constructs comprise DNA segments encoding a complete human immunoglobulin heavy chain and/or a complete human immunoglobulin light chain of an immunoglobulin expressed by a trioma cell line. Alternatively, DNA segments encoding only a portion of the primary antibody genes are produced, which portions possess binding and/or effector activities. Other recombinant constructs contain segments of trioma cell line immunoglobulin genes fused to segments of other immunoglobulin genes, particularly segments of other human constant region sequences (heavy and/or light chain). Human constant region sequences can be selected from various reference sources, including but not limited to those listed in Kabat et al. (1987), *Sequences of proteins of Immunological Interest*, U.S. Department of Health and Human Services.

In addition to the DNA segments encoding anti-ESX immunoglobulins or fragments thereof, other substantially homologous modified immunoglobulins can be readily designed and manufactured utilizing various recombinant DNA techniques known to those skilled in the art such as site-directed mutagenesis (see, e.g., Gillman & Smith (1979) *Gene*, 8: 81–97; Roberts et al. (1987) *Nature*, 328: 731–734). Such modified segments will usually retain antigen binding capacity and/or effector function. Moreover, the modified segments arc usually not so far changed from the original trioma genomic sequences to prevent hybridization to these sequences under stringent conditions. Because, like many genes, immunoglobulin genes contain separate functional regions, each having one or more distinct biological activities, the genes may be fused to functional regions from other genes to produce fusion proteins (e.g., immunotoxins) having novel properties or novel combinations of properties.

The recombinant polynucleotide constructs will typically include an expression control sequence operably linked to the coding sequences, including naturally-associated or heterologous promoter regions. Preferably, the expression control sequences will be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the human anti-ESX immunoglobulins.

These expression vectors are typically replicable in the host organisms either as episomes or as an integral part of the host chromosomal DNA. Commonly, expression vectors will contain selection markers, e.g., ampicillin-resistance or hygromycin-resistance, to permit detection of those cells transformed with the desired DNA sequences.

In general, prokaryotes can be used for cloning the DNA sequences encoding a human anti-ESX immunoglobulin chain. *E. coli* is one prokaryotic host particularly useful for cloning the DNA sequences of the present invention. Microbes, such as yeast are also useful for expression. *Saccharomyces* is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase 2, isocytochrome C, and enzymes responsible for maltose and galactose utilization.

Mammalian cells are a particularly preferred host for expressing nucleotide segments encoding immunoglobulins or fragments thereof (see, e.g., Winnacker (1987) *From Genes to Clones*, VCH Publishers, N.Y.). A number of suitable host cell lines capable of secreting intact heterologous proteins have been developed in the art, and include CHO cell lines, various COS cell lines, HeLa cells, L cells and myeloma cell lines. Preferably, the cells are nonhuman. Expression vectors for these cells can include expression control sequences, such as an origin of replication, a promoter, an enhancer (Queen et al. (1986) *Immunol. Rev.* 89: 49), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like (see, e.g., Co et al. (1992) *J. Immunol.,* 148: 1149).

The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection may be used for other cellular hosts. Other methods used to transform mammalian cells include the use of polybrene, protoplast fusion, liposomes, electroporation, and microinjection (see, generally, Sambrook et al., supra).

Once expressed, human anti-ESX immunoglobulins of the invention can be purified according to standard procedures of the art, including HPLC purification, fraction column chromatography, gel electrophoresis and the like (see, generally, Scopes (1982) *Protein Purification*, Springer-Verlag, N.Y.). Detailed protocols for the production of human antibodies can be found in U.S. Pat. No. 5,506,132.

Other approaches in vitro immunization of human blood. In this approach, human blood lymphocytes capable of producing human antibodies are produced. Human peripheral blood is collected from the patient and is treated to recover mononuclear cells. The suppressor T-cells then are removed and remaining cells are suspended in a tissue culture medium to which is added the antigen and autologous serum and, preferably, a nonspecific lymphocyte activator. The cells then are incubated for a period of time so that they produce the specific antibody desired. The cells then can be fused to human myeloma cells to immortalize the cell line, thereby to permit continuous production of antibody (see U.S. Pat. No. 4,716,111).

In another approach, mouse-human hybridomas which produces human anti-ESX are prepared (see, e.g., U.S. Pat. No. 5,506,132). Other approaches include immunization of mice transformed to express human immunoglobulin genes, and phage display screening (Vaughan et al. supra.).

IV. Production of ESX Polypeptides.

A) De Novo Chemical Synthesis.

The ESX proteins or subsequences thereof may be synthesized using standard chemical peptide synthesis techniques. Where the desired subsequences are relatively short (e.g., when a particular antigenic determinant is desired) the molecule may be synthesized as a single contiguous polypeptide. Where larger molecules are desired, subsequences can be synthesized separately (in one or more units) and then fused by condensation of the amino terminus of one molecule with the carboxyl terminus of the other molecule thereby forming a peptide bond.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis*; pp. 3–284 in *The Peptides: Analysis, Synthesis, Biology. VoL* 2: *Special Methods in Peptide Synthesis, Part A*., Merrifield, et al. (1963) *J. Am. Chem. Soc.,* 85: 2149–2156, and Stewart et al. (1984) *Solid Phase Peptide Synthesis, 2nd ed.* Pierce Chem. Co., Rockford, Ill.

B) Recombinant Expression.

In a preferred embodiment, the ESX proteins or subsequences thereof, are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the ESX proteins or subsequences of this invention can be prepared by any suitable method as described above, including, for example, cloning and restriction of appropriate sequences or direct chemical synthesis by methods such as the phosphotriester method of Narang et al. (1979) *Meth. Enzymol.* 68: 90–99; the phosphodiester method of Brown et al.(1979) *Meth. Enzymol.* 68: 109–151; the diethylphosphoramidite method of Beaucage et al. (1981) *Tetra. Lett.,* 22: 1859–1862; and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence.

In one embodiment, ESX proteins of this invention can be cloned using DNA amplification methods such as polymerase chain reaction (PCR). Thus, for example, the nucleic acid sequence or subsequence is PCR amplified, using a sense primer containing one restriction site (e.g., NdeI) and an antisense primer containing another restriction site (e.g., HindIII). This will produce a nucleic acid encoding the desired ESX sequence or subsequence and having terminal restriction sites. This nucleic acid can then be easily ligated into a vector containing a nucleic acid encoding the second molecule and having the appropriate corresponding restriction sites. Suitable PCR primers can be determined by one of skill in the art using the sequence information provided in SEQ ID NOs: 1 and 3. Appropriate restriction sites can also be added to the nucleic acid encoding the ESX protein or protein subsequence by site-directed mutagenesis. The plasmid containing the ESX sequence or subsequence is cleaved with the appropriate restriction endonuclease and then ligated into the vector encoding the second molecule according to standard methods.

The nucleic acid sequences encoding ESX proteins or protein subsequences may be expressed in a variety of host cells, including *E. coli*, other bacterial hosts, yeast, and various higher eukaryotic cells such as the COS, CHO and HeLa cells lines and myeloma cell lines. As the ESX proteins are typically found in eukaryotes, a eukaryote host is preferred. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant ESX proteins can be purified according to standard procedures of the art, including ammonium sulfate precipitation, affinity columns, column chromatography, gel electrophoresis and the like (see, generally, R. Scopes, (1982) *Protein Purification*, Springer-Verlag, N.Y.; Deutscher (1990) *Methods in Enzymology Vol. 182: Guide to Protein Purfication*., Academic Press, Inc. N.Y.). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production).

One of skill in the art would recognize that after chemical synthesis, biological expression, or purification, the ESX protein(s) may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (See, Debinski et al. (1993) *J. Biol. Chem.*, 268: 14065–14070; Kreitman and Pastan (1993) *Bioconjug. Chem.*, 4: 581–585; and Buchner, et al., (1992) *Anal. Biochem.*, 205: 263–270). Debinski et al., for example, describes the denaturation and reduction of inclusion body proteins in guanidine-DTE. The protein is then refolded in a redox buffer containing oxidized glutathione and L-arginine.

One of skill would recognize that modifications can be made to the ESX proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

V. Detection of ESX.

As indicated above, abnormal (e.g., altered or deficient) expression of the human ESX gene is believed to be a causal factor in the development of various cancers (e.g., head, neck, breast, ovary, bladder, colon, etc.). In particular, the data provided herein establish the importance of the ESX gene in the etiology of carcinomas, including epithelial cancers such as breast cancer. ESX becomes overexpressed at an early stage of breast cancer known as ductal carcinoma in situ, making abnormal expression of ESX a marker for early detection of cancers. Of course, early detection can be critical to treatment efficacy. It is believed that abnormal expression of the ESX gene influences transcription of genes that are regulated by the ESX transcription factor.

Thus, it is desirable to determine the presence or absence, or quantify, the expression of ESX polypeptides and of the nucleic acids encoding the ESX polypeptides. This may be accomplished by assaying the gene product, ESX polypeptides themselves, or alternatively, by assaying the nucleic acids (DNA or mRNA) that encode the ESX polypeptides. In particular, it is desirable to determine whether ESX expression is present, absent, or abnormal (e.g. because of an abnormal gene product, because of chromosomal amplification or deletion, or because of abnormal expression levels as, for example, with a hemizygous gene). Particularly, where it is desired to determine a heritable propensity for abnormal ESX gene expression, it is preferred to assay the host DNA for abnormal ESX genes or gene transcripts (mRNAs).

A) Sample Collection and Processing

The ESX gene or gene product (i.e., mRNA or polypeptide) is preferably detected and/or quantified in a biological sample. As used herein, a biological sample is a sample of biological tissue or fluid that, in a healthy and/or pathological state, contains an ESX nucleic acid or polypeptide. Such samples include, but are not limited to, sputum, amniotic fluid, blood, blood cells (e.g., white cells), tissue or fine needle biopsy samples, urine, peritoneal fluid, and pleural fluid, or cells therefrom. Biological samples may also include sections of tissues such as frozen sections taken for histological purposes. Often, a sample will be obtained from a cancerous or precancerous tissue. Although the sample is typically taken from a human patient, the assays can be used to detect ESX genes or gene products in samples from any mammal, such as dogs, cats, sheep, cattle, and pigs.

The sample may be pretreated as necessary by dilution in an appropriate buffer solution or concentrated, if desired. Any of a number of standard aqueous buffer solutions, employing one of a variety of buffers, such as phosphate, Tris, or the like, at physiological pH can be used.

B) Control for Physiological State.

As explained herein, expression levels of the ESX gene vary with the developmental and reproductive state of the organism. Thus, for example, in mice, ESX expression is induced early in fetal development (e.g., greater than about 7 days), is substantially diminished or lost during lactation, and dramatically increases post-weaning.

In light of this variation, it will be appreciated that abnormal levels of ESX expression will be determined relative to a control reflecting the developmental state of the animal or human and preferably the reproductive state as well. Thus controls will be matched for gestational stage according to standard methods known to those of skill in the art.

C) Nucleic Acid Assays.

In one embodiment, this invention provides for methods of detecting and/or quantifying human ESX expression by assaying the underlying ESX gene (or a fragment thereof) or by assaying the ESX gene transcript (mRNA). The assay can be for the presence or absence of the normal gene or gene product, for the presence or absence of an abnormal gene or gene product, or quantification of the transcription levels of normal or abnormal ESX gene product.

i) Nucleic Acid Sample.

In a preferred embodiment, nucleic acid assays are performed with a sample of nucleic acid isolated from the organism to be tested. In the simplest embodiment, such a nucleic acid sample is the total mRNA isolated from a biological sample. The nucleic acid (e.g., either genomic DNA or mRNA) may be isolated from the sample according to any of a number of methods well known to those of skill in the art. One of skill will appreciate that where alterations in the copy number of the ESX gene are to be detected genomic DNA is preferably isolated. Conversely, where expression levels of a gene or genes are to be detected, preferably RNA (mRNA) is isolated.

Methods of isolating total DNA or mRNA are well known to those of skill in the art. For example, methods of isolation and purification of nucleic acids are described in detail in Tijssen, (1993) Chapter 3 of *Laboratory Techniques in Biochemistry and Molecular Biology: Hybridization With Nucleic Acid Probes, Part I. Theory and Nucleic Acid Preparation*, Elsevier, N.Y.).

In a preferred embodiment, the total nucleic acid is isolated from a given sample using, for example, an acid guanidinium-phenol-chloroform extraction method and polyA+ mRNA is isolated by oligo dT column chromatography or by using (dT)n magnetic beads (see, e.g., Sambrook et al. (1989) *Molecular Cloning: A Laboratory Manual* (2nd ed.), Vols. 1–3, Cold Spring Harbor Laboratory, or Ausubel et al. (1987) *Current Protocols in Molecular Biology*, Greene Publishing and Wiley-Interscience, New York).

Frequently, it is desirable to amplify the nucleic acid sample prior to hybridization. One of skill in the art will appreciate that whatever amplification method is used, if a quantitative result is desired, care must be taken to use a method that maintains or controls for the relative frequencies of the amplified nucleic acids.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid.

One preferred internal standard is a synthetic AW106 cRNA. The AW106 cRNA is combined with RNA isolated from the sample according to standard techniques known to those of skill in the art. The RNA is then reverse transcribed using a reverse transcriptase to provide copy DNA. The cDNA sequences are then amplified (e.g., by PCR) using labeled primers. The amplification products are separated, typically by electrophoresis, and the amount of radioactivity (proportional to the amount of amplified product) is determined. The amount of mRNA in the sample is then calculated by comparison with the signal produced by the known AW106 RNA standard. Detailed protocols for quantitative PCR are provided in Innis et al. (1990) *PCR Protocols, A Guide to Methods and Applications*, Academic Press, Inc. N.Y.

Other suitable amplification methods include, but are not limited to polymerase chain reaction (PCR) (Innis et al. supra.), ligase chain reaction (LCR) (see Wu and Wallace (1989) *Genomics*, 4: 560; Landegren et al. (1988) *Science*, 241: 1077, and Barringer et al. (1990) *Gene*, 89: 117, transcription amplification (Kwoh et al. (1989) *Proc. Natl. Acad. Sci. USA*, 86: 1173), and self-sustained sequence replication (Guatelli et al. (1990) *Proc. Nat. Acad. Sci. USA*, 87: 1874).

ii) Hybridization Assays.

A variety of methods for specific DNA and RNA measurement using nucleic acid hybridization techniques are known to those of skill in the art (see Sambrook, et al. supra). For example, one method for evaluating the presence, absence, or quantity of DNA encoding ESX proteins in a sample involves a Southern transfer. Briefly, the digested genomic DNA is run on agarose slab gels in buffer and transferred to membranes.

Hybridization is carried out using the nucleic acid probes specific for the target ESX sequence or subsequence. Nucleic acid probes are designed based on the nucleic acid sequences encoding ESX proteins (see SEQ ID NOs: 1 and 3). The probes can be full length or less than the full length of the nucleic acid sequence encoding the ESX protein. Shorter probes are empirically tested for specificity. Preferably nucleic acid probes are 20 bases or longer in length (see Sambrook, et al. supra. for methods of selecting nucleic acid probe sequences for use in nucleic acid hybridization.) Visualization of the hybridized portions allows the qualitative determination of the presence or absence of DNA encoding ESX proteins.

Similarly, a Northern transfer can be used for the detection of mRNA encoding ESX proteins. In brief, the mRNA is isolated from a given cell sample using, for example, an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify the presence or absence of ESX proteins.

A variety of nucleic acid hybridization formats are known to those skilled in the art. For example, common formats include sandwich assays and competition or displacement assays. Hybridization techniques are generally described in Hames and Higgins (1985) *Nucleic Acid Hybridization, A Practical Approach*," IRL Press; Gall and Pardue (1969) *Proc. Natl. Acad. Sci., USA*, 63: 378–383; and John et al. (1969) *Nature*, 223: 582–587.

For example, sandwich assays are commercially useful hybridization assays for detecting or isolating nucleic acid sequences. Such assays utilize a "capture" nucleic acid covalently immobilized to a solid support and a labeled "signal" nucleic acid in solution. The clinical sample will provide the target nucleic acid. The "capture" nucleic acid and "signal" nucleic acid probe hybridize with the target nucleic acid to form a "sandwich" hybridization complex. To be effective, the signal nucleic acid should not hybridize with the capture nucleic acid.

Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labelled probes or the like. Other labels include ligands which bind to labeled antibodies, fluorophores, chemi-luminescent agents, enzymes, and antibodies which can serve as specific binding pair members for a labeled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The label may also allow indirect detection of the hybridization complex. For example, where the label is a hapten or antigen, the sample can be detected by using antibodies. In these systems, a signal is generated by attaching fluorescent or enzyme molecules to the antibodies or, in some cases, by attachment to a radioactive label. (Tijssen (1985) *Practice and Theory of Enzyme Immunoassays*, pp 9–20 in *Laboratory Techniques in Biochemistry and Molecular Biology*, Burdon, R. H., van Knippenberg, P. H., Eds., Elsevier).

The sensitivity of the hybridization assays may be enhanced through use of a nucleic acid amplification system which multiplies the target nucleic acid being detected. Examples of such systems include the polymerase chain reaction (PCR) system and the ligase chain reaction (LCR) system. Other methods recently described in the art are the nucleic acid sequence based amplification (NASBAJ, Cangene, Mississauga, Ontario) and Q Beta Replicase systems.

An alternative means for determining the level of expression of a gene encoding an ESX protein is in situ hybridization. In situ hybridization assays are well known and are generally described in Angerer, et al. (1987) *Methods Enzymol.*, 152: 649–660. In an in situ hybridization assay, cells or tissue specimens are fixed to a solid support, typically a glass slide. If DNA is to be probed, the cells are denatured with heat or alkali. The cells are then contacted with a hybridization solution at a moderate temperature to permit annealing of labeled probes specific to ESX nucleic acids. The probes are preferably labelled with radioisotopes or fluorescent reporters. Detection of ESX nucleic acids by in situ hybridization is detailed in Example 1.

iii) Amplification Based Assays.

In another embodiment, the ESX gene or gene product can be detected (assayed) using an amplification based assay. In an amplification based assay, all or part of the ESX gene or transcript (e.g., mRNA or cDNA) is amplified and the amplification product is then detected. Where there is no underlying gene or gene product to act as a template amplification is non-specific or non-existent and there is no single amplification product. Where the underlying gene or gene product is present, the target sequence is amplified providing an indication of the presence, absence, or quantity of he underlying gene or mRNA.

Amplification-based assays are well known to those of skill in the art (see, e.g., Innis, supra.). The cDNA sequence provided for the ESX gene is sufficient to enable one of skill to routinely select primers to amplify any portion of the gene. In addition, Table 1 provides primer pairs for the PCR amplification of the ESX gene.

Amplification primers can be selected to provide amplification products that span specific deletions, truncations, and insertions, as discussed below (see, Section iv, below) thereby facilitating the detection of specific abnormalities.

iv) Specific Detection of Abnormalities (e.g. Mutations, Amplifications, Rearrangements).

Abnormal ESX genes or gene products are sometimes characterized by premature stop codons, deletions, or insertions. Premature stop codons and deletions can be detected by decreased size of the gene or gene product (mRNA transcript or cDNA). Similarly, insertions can be detected by increased size of the gene or gene product. Alternatively, mutations can be determined by sequencing of the gene or gene product according to standard methods. In addition, amplification assays and hybridization probes can be selected to specifically target particular abnormalities. For example, where the abnormality is a deletion, nucleic acid probes or amplification primers can be selected that specifically hybridize to or amplify, respectively the deletion. Where the ESX gene harbors such a deletion, the probe will fail to hybridize or the amplification reaction will fail to provide specifically amplification. Alternatively, the probe or amplification reaction can be designed to span the entire deletion or either end of the deletion (deletion junction). Similarly, probes and amplification primers can be selected that specifically target point mutations or insertions.

As explained herein, the detection of 1q aneusomy or amplification/increased copy number for genes located in the 1q32 region is indicative of the presence and/or prognosis of a large number of cancers. These include, but are not limited to, breast, ovary, bladder, head and neck, and colon. The detection of amplified or deleted chromosomal regions has traditionally been done by cytogenetics. Because of the complex packing of DNA into the chromosomes, resolution of cytogenetic techniques has been limited to regions larger than about 10 Mb; approximately the width of a band in Giemsa-stained chromosomes. In complex karyotypes with multiple translocations and other genetic changes, traditional cytogenetic analysis is of little utility because karyotype information is lacking or cannot be interpreted. Teyssier (1989) *Cancer Genet. Cytogenet.*, 37: 103. Furthermore conventional cytogenetic banding analysis is time consuming, labor intensive, and frequently difficult or impossible.

In a more preferred embodiment, a 1q32 amplification is detected through the hybridization of a probe of this invention to a target nucleic acid (e.g. a chromosomal sample) in which it is desired to screen for the amplification. Suitable hybridization formats are well known to those of skill in the art and include, but are not limited to, variations of Southern Blots, in situ hybridization and quantitative amplification methods such as quantitative PCR (see, e.g., Sambrook, supra., Kallioniemi et al. (1992) *Proc. Natl. Acad Sci USA*, 89: 5321–5325, and Innis et al., supra.).

Southern blotting is effective even if the genome is heavily rearranged so as to eliminate useful karyotype information. However, Southern blotting only gives a rough estimate of the copy number of a DNA sequence, and does not give any information about the localization of that sequence within the chromosome. Comparative genomic hybridization (CGH) is a more recent approach to identify the presence and localization of amplified/deleted sequences (see Kallioniemi, et al. (1992) *Science*, 258: 818). CGH, like Southern blotting, reveals amplifications and deletions irrespective of genome rearrangement. Additionally, CGH provides a more quantitative estimate of copy number than Southern blotting, and moreover also provides information about the localization of the amplified or deleted sequence in the normal chromosome.

In a preferred embodiment, the 1q32 amplicon is identified using in situ hybridization. Generally, in situ hybridization comprises the following major steps: (1) fixation of tissue or biological structure to analyzed; (2) prehybridization treatment of the biological structure to increase accessibility of target DNA, and to reduce nonspecific binding; (3) hybridization of the mixture of nucleic acids to the nucleic acid in the biological structure or tissue; (4) posthybridization washes to remove nucleic acid fragments not bound in the hybridization and (5) detection of the hybridized nucleic acid fragments. The reagent used in each of these steps and their conditions for use vary depending on the particular application.

In some applications it is necessary to block the hybridization capacity of repetitive sequences. In this case, human genomic DNA is used as an agent to block such hybridization. The preferred size range is from about 200 bp to about 1000 bases, more preferably between about 400 to about 800 bp for double stranded, nick translated nucleic acids.

Hybridization protocols for the particular applications disclosed here are described in Pinkel et al. (1988) *Proc. Natl. Acad. Sci. USA,* 85: 9138–9142 and in EPO Pub. No. 430,402. Suitable hybridization protocols can also be found in Choo (1994) *Methods in Molecular Biology Vol.* 33: In Situ Hybridization Protocols, Humana Press, Totowa, N.J. In a particularly preferred embodiment, the hybridization protocol of Kallioniemi et al. (1992) *Proc. Natl Acad Sci USA,* 89: 5321–5325 is used.

Typically, it is desirable to use dual color fluorescence in situ hybridization (FISH), in which two probes are utilized, each labeled by a different fluorescent dye. A test probe that hybridizes to the region of interest is labeled with one dye, and a control probe that hybridizes to a different region is labeled with a second dye. A nucleic acid that hybridizes to a stable portion of the chromosome of interest, such as the centromere region, is often most useful as the control probe. In this way, differences between efficiency of hybridization from sample to sample can be accounted for.

The FISH methods for detecting chromosomal abnormalities can be performed on nanogram quantities of the subject nucleic acids. Paraffin embedded tumor sections can be used, as can fresh or frozen material. Because FISH can be applied to the limited material, touch preparations prepared from uncultured primary tumors can also be used (see, e.g., Kallioniemi, et al. (1992) *Cytogenet Cell Genet.* 60: 190–193). For instance, small biopsy tissue samples from tumors can be used for touch preparations (see, e.g., Kallioniemi, et al. (1992) supra.). Small numbers of cells obtained from aspiration biopsy or cells in bodily fluids (e.g., blood, urine, sputum and the like) can also be analyzed. For prenatal diagnosis, appropriate samples will include amniotic fluid and the like.

iv) Detection of Expression Levels.

Where it is desired to quantify the transcription level (and thereby expression) of a normal or mutated ESX genes in a sample, the nucleic acid sample is one in which the concentration of the mRNA transcript(s) of the ESX gene, or the concentration of the nucleic acids derived from the mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of the target mRNA results in a 3 to 6 fold difference in hybridization intensity is sufficient for most purposes. Where more precise quantification is required appropriate controls can be run to correct for variations introduced in sample preparation and hybridization as described herein. In addition, serial dilutions of "standard" target mRNAs can be used to prepare calibration curves according to methods well known to those of skill in the art. Of course, where simple detection of the presence or absence of a transcript is desired, no elaborate control or calibration is required.

D) ESX Polypeptide Assays.

The expression of the human ESX gene can also be detected and or quantified by detecting or quantifying the expressed ESX polypeptide. The ESX polypeptides can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

In a particularly preferred embodiment, the ESX polypeptides are detected in an electrophoretic protein separation, more preferably in a two-dimensional electrophoresis, while in a most preferred embodiment, the ESX polypeptides are detected using an immunoassay.

As used herein, an immunoassay is an assay that utilizes an antibody to specifically bind to the analyte (ESX polypeptide). The immunoassay is thus characterized by detection of specific binding of a ESX polypeptide to an anti-ESX antibody as opposed to the use of other physical or chemical properties to isolate, target, and quantify the analyte.

i) Electrophoretic Assays.

As indicated above, the presence or absence of ESX polypeptides in a biological sample can be determined using electrophoretic methods. Means of detecting proteins using electrophoretic techniques are well known to those of skill in the art (see generally, Scopes (1982) *Protein Purification,* Springer-Verlag, N.Y.; Deutscher, (1990) *Methods in Enzymology VoL* 182: *Guide to Protein Purification,* Academic Press, Inc., N.Y.).

ii) Immunological Binding Assays.

In a preferred embodiment, the ESX polypeptides are detected and/or quantified using any of a number of well recognized immunological binding assays (see, e.g., U.S. Pat. Nos. 4,366,241; 4,376,110; 4,517,288; and 4,837,168). For a review of the general immunoassays, see also Asai (1993) *Methods in Cell Biology Volume* 37: *Antibodies in Cell Biology,* Academic Press, Inc. New York; Stites and Terr (1991) *Basic and Clinical Immunology* 7th Edition. Immunological binding assays (or immunoassays) typically utilize a "capture agent" to specifically bind to and often immobilize the analyte (in this case ESX polypeptide or subsequence). The capture agent is a moiety that specifically binds to the analyte. In a preferred embodiment, the capture agent is an antibody that specifically binds ESX polypeptide(s). The antibody (anti-ESX) may be produced by any of a number of means well known to those of skill in the art as described above in Section III(A).

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled ESX polypeptide or a labeled anti-ESX antibody. Alternatively, the labeling agent may be a third moiety, such as another antibody, that specifically binds to the antibody/ESX complex.

In a preferred embodiment, the labeling agent is a second human ESX antibody bearing a label. Alternatively, the second ESX antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.,* 111: 1401–1406, and Akerstrom, et al. (1985) *J. Immunol.,* 135: 2589–2542).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40°.

a) Non-Competitive Assay Formats.

Immunoassays for detecting ESX polypeptide may be either competitive or noncompetitive. Noncompetitive immunoassays are assays in which the amount of captured analyte (in this case ESX) is directly measured. In one preferred "sandwich" assay, for example, the capture agent (anti-ESX antibodies) can be bound directly to a solid substrate where they are immobilized. These immobilized antibodies then capture ESX present in the test sample. The ESX thus immobilized is then bound by a labeling agent, such as a second human ESX antibody bearing a label. Alternatively, the second ESX antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

b) Competitive Assay Formats.

In competitive assays, the amount of analyte (ESX) present in the sample is measured indirectly by measuring the amount of an added (exogenous) analyte (ESX) displaced (or competed away) from a capture agent (anti ESX antibody) by the analyte present in the sample. In one competitive assay, a known amount of, in this case, ESX is added to the sample and the sample is then contacted with a capture agent, in this case an antibody that specifically binds ESX. The amount of ESX bound to the antibody is inversely proportional to the concentration of ESX present in the sample.

In a particularly preferred embodiment, the antibody is immobilized on a solid substrate. The amount of ESX bound to the antibody may be determined either by measuring the amount of ESX present in an ESX/antibody complex, or alternatively by measuring the amount of remaining uncomplexed ESX. The amount of ESX may be detected by providing a labeled ESX molecule.

A hapten inhibition assay is another preferred competitive assay. In this assay a known analyte, in this case ESX is immobilized on a solid substrate. A known amount of anti-ESX antibody is added to the sample, and the sample is then contacted with the immobilized ESX. In this case, the amount of anti-ESX antibody bound to the immobilized ESX is inversely proportional to the amount of ESX present in the sample. Again the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

c) Other Assay Formats.

In a particularly preferred embodiment, Western blot (immunoblot) analysis is used to detect and quantify the presence of ESX in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind ESX. The anti-ESX antibodies specifically bind to ESX on the solid support. These antibodies may be directly labeled or alternatively may be subsequently detected using labeled antibodies (e.g., labeled sheep anti-mouse antibodies) that specifically bind to the anti-ESX.

Other assay formats include liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5:34–41).

d) Scoring of the Assay.

The assays of this invention as scored (as positive or negative for ESX polypeptide) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. In a preferred embodiment, a positive test will show a signal intensity (e.g., ESX polypeptide quantity) at least twice that of the background and/or control and more preferably at least 3 times or even at least 5 times greater than the background and/or negative control.

e) Reduction of Non-Specific Binding.

One of skill in the art will appreciate that it is often desirable to reduce non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this involves coating the substrate with a proteinaceous composition. In particular, protein compositions such as bovine serum albumin (BSA), nonfat powdered milk, and gelatin are widely used with powdered milk being most preferred.

E) Labels.

The particular label or detectable group used in the assay is not a critical aspect of the invention, so long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g. polystyrene, polypropylene, latex, etc.) beads.

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

F) Substrates.

As mentioned above, depending upon the assay, various components, including the antigen, target antibody, or anti-human antibody, may be bound to a solid surface. Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass or plastic bead. The desired component may be covalently bound or noncovalently attached through non-specific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glasses, ceramics, metals, metalloids, semiconductive materials, cements or the like. In addition, are included substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12–24 carbon atoms) alkyl ammonium salts and the like are also suitable. Where the solid surface is porous, various pore sizes may be employed depending upon the nature of the system.

In preparing the surface, a plurality of different materials may be employed, particularly as laminates, to obtain various properties. For example, protein coatings, such as gelatin can be used to avoid non-specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature (see, e.g., Chibata (1978) *Immobilized Enzymes*, Halsted Press, New York, and Cuatrecasas (1970) *J. Biol. Chem.* 245: 3059).

In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as Concanavalin A will bind a carbohydrate containing compound but not a labeled protein that lacks glycosylation. Various solid surfaces for use in noncovalent attachment of assay components are reviewed in U.S. Pat. Nos. 4,447,576 and 4,254,082.

G) Evaluation of ESX Expression Levels and/or Abnormal Expression.

One of skill will appreciate that abnormal expression levels or abnormal expression products (e.g., mutated transcripts, truncated or non-sense polypeptides) are identified by comparison to normal expression levels and normal expression products. Normal levels of expression or normal expression products can be determined for any particular population, subpopulation, or group of organisms according to standard methods well known to those of skill in the art. Typically this involves identifying healthy organisms and/or tissues (i.e. organisms and/or tissues without ESX expression dysregulation or neoplastic growth) and measuring expression levels of the ESX gene (as described herein) or sequencing the gene, mRNA, or reverse transcribed cDNA, to obtain typical (normal) sequence variations. Application of standard statistical methods used in molecular genetics permits determination of baseline levels of expression, and normal gene products as well as significant deviations from such baseline levels.

Preferably, normal levels of expression are determined using a control organism or tissue that is in a physiological milieu that is similar to that of the test sample. For example, ESX expression can be influenced by age of the organism, pregnancy, menopause, and day of menstrual cycle, among other factors. Therefore, it is preferred to choose as a control tissue one that is at a similar stage as the tissue being tested for abnormal ESX expression. For example, a tissue known to be healthy can be obtained from the same organism from which the test tissue is obtained.

VI. Detection Kits.

The present invention also provides for kits for the diagnosis of organisms (e.g., patients) with a predisposition (at risk) for carcinomas, including epithelial cancers. The kits preferably include one or more reagents for determining the presence or absence of the ESX gene, for quantifying expression of the ESX gene, or for detecting an abnormal ESX gene (amplified or rearranged), or expression products of an abnormal ESX gene. Preferred reagents include nucleic acid probes that specifically bind to the normal ESX gene, cDNA, or subsequence thereof, probes that specifically bind to abnormal ESX gene (e.g. ESX genes containing premature truncations, insertions, or deletions), antibodies that specifically bind to normal ESX polypeptides or subsequences thereof, or antibodies that specifically bind to abnormal ESX polypeptides or subsequences thereof. The antibody or hybridization probe may be free or immobilized on a solid support such as a test tube, a microtiter plate, a dipstick and the like. The kit may also contain instructional materials teaching the use of the antibody or hybridization probe in an assay for the detection of a predisposition for ESX.

The kits may include alternatively, or in combination with any of the other components described herein, an anti-ESX antibody. The antibody can be monoclonal or polyclonal. The antibody can be conjugated to another moiety such as a label and/or it can be immobilized on a solid support (substrate).

The kit(s) may also contain a second antibody for detection of ESX polypeptide/antibody complexes or for detection of hybridized nucleic acid probes. The kit may contain appropriate reagents for detection of labels, positive and negative controls, washing solutions, dilution buffers and the like.

VII. Transgenic Animals.

In another embodiment, this invention provides for transgenic ESX animals. In preferred embodiments, three types of transgenic animals are contemplated: 1) Animals in expressing a heterologous ESX gene; 2) Animals whose expression of an endogenous ESX is altered by modification or replacement of the endogenous promoter; and 3) animals whose expression of endogenous ESX is altered (e.g., inhibited) by modification of the ESX introns and/or exons.

A) Expression of Heterologous ESX.

Using the sequence information provided herein, transformation of animals to express heterologous ESX constructs (e.g., cDNA) can be accomplished routinely. Methods to transforming organisms are described below in section VIII(D). It will be appreciated that many ESX costructs are suitable for in vivo transformation. The particular construct typically being selected for expression level, tissue specificity, and the like. In one preferred embodiment, an ESX cDNA is placed in a vector comprising the MMTV LTR and containing the polyA signaling and splicing sequence from SV40 (see, e.g., Example 4).

B) Modification of the Endogenous Promoter.

In another embodiment, transgenic animals (e.g., mice) can be produced in which the expression of the ESX gene can be altered by altering the endogenous promoter. Methods of modifying or replacing native promoters to alter expression of endogenous genes are well known to those of skill in the art (see, e.g., Section VIII(B)(iii) below, and U.S. Pat. No. 5,272,071, WO 91/09955, WO 93/09222, WO 96/29411, WO 95/31560, and WO 91/12650).

B) ESX Knockouts.

In still another embodiment, this invention provides ESX knockout animals (e.g., knockout mice) in which the expression of the ESX gene is reduced and/or eliminated in one or more tissues or in the entire organism. Preparation of a knockout mammal is preferably accomplished by first introducing a nucleic acid construct (a knockout construct) that will be used to suppress expression of a particular gene into an undifferentiated cell type termed an embryonic stem cell. This cell is then injected into a mammalian embryo, where it hopefully will be integrated into the developing embryo. The embryo is then implanted into a foster mother for the duration of gestation.

The term "knockout construct" refers to a nucleic acid sequence that is designed to decrease or suppress expression of a protein encoded by endogenous DNA sequences in a cell. The nucleic acid sequence used as the knockout construct is typically comprised of (1) DNA from some portion of the gene (e.g., ESX exon sequence, intron sequence, and/or promoter sequence) to be suppressed and (2) a marker sequence used to detect the presence of the knockout construct in the cell. The knockout construct is inserted into a cell, and integrates with the genomic DNA of the cell in such a position so as to prevent or interrupt transcription of the native (ESX) DNA sequence. Such insertion usually occurs by homologous recombination (i.e., regions of the knockout construct that are homologous to endogenous DNA sequences hybridize to each other when the knockout construct is inserted into the cell and recombine so that the knockout construct is incorporated into the corresponding position of the endogenous DNA). The knockout construct nucleic acid sequence may comprise 1) a full or partial sequence of one or more exons and/or introns of the gene to be suppressed, 2) a full or partial promoter sequence of the gene to be suppressed, or 3) combinations thereof.

Typically, the knockout construct is inserted into an embryonic stem cell (ES cell) and is integrated into the ES cell genomic DNA, usually by the process of homologous recombination. This ES cell is then injected into, and integrates with, the developing embryo.

By way of example, a nucleic acid construct can be prepared containing a DNA sequence encoding an antibiotic resistance gene which is inserted into the DNA sequence that is complementary to the ESX DNA sequence (promoter and/or coding region) to be disrupted. When this nucleic acid construct is then transfected into a cell, the construct will integrate into the genomic DNA. Thus, many progeny of the cell will no longer express the gene at least in some cells, or will express it at a decreased level, as the DNA is disrupted by the antibiotic resistance gene. Methods of producing knockout transgenic animals are well known to those of skill in the art (see, e.g., U.S. Pat. No. 5,616,491 and references therein).

VIII. ESX Modulation/Therapeutics.

The ESX polypeptide appears to be an extremely strong gene transactivator, as revealed by GAL4 fusion studies showing that the ESX amino acid sequences encoded by ESX exon 4 are as powerful as the transactivating sequences of VP16, one of the strongest transactivators known and most often used as a positive control in GAL4 fusion studies. These studies indicate that ESX is most likely "turning on" rather than "turning off" all the genes under its control (e.g., growth factor receptors such as erbB2, and extracellular matrix proteases such as MMPs, and UPA). Up-regulation of ESX will therefore turn on (e.g., transactivate) genes under ESX control, while down-regulation of ESX will turn off genes under ESX control.

A) Screening for ESX Modulation.

As indicated earlier, ESX controls a number of functions including, but not limited to in remodeling ductal epithelium and in regulating gene programs involved with this process (e.g. extracellular matrix degradation, apoptosis, etc.). In particular extracellular matrix degradation control or apoptosis appear to be essential for enhanced tumor cell invasion and metastasis. Modulation of such functions is useful in both a research and a therapeutic context. Thus, in one embodiment, this invention provides methods of screening for agents that modulate (e.g., up-regulate (turn on or increase) or down-regulate (turn off or decrease) ESX expression or ESX polypeptide activity.

Generally such methods involve contacting a cell containing an endogenous or heterologous ESX gene or cDNA with the agent that is to be screened for ESX modulatory activity and detecting a change in expression level of the ESX gene or a change in activity of the ESX polypeptide. It will be appreciated that level of transcription of EXS mRNA or amount of translated ESX polypeptide is a good measure of expression level of the ESX gene. Methods of detecting ESX nucleic acids and ESX polypeptides are described in detail above. In a preferred embodiment, an agent that induces a statistically significant change in ESX transcription level (e.g., as compared to a control assay lacking the agent) will be regarded as showing ESX modulatory activity. In a more preferred embodiment, the change will be at least two-fold, and in a most preferred embodiment at least 5-fold or even at least 10-fold.

It will also be appreciated that in vitro or in vivo ESX DNA binding assays are also useful for assessing activity of the ESX polypeptide. Thus, for example where an agent inhibits, blocks, or competes with ESX for binding of the substrate nucleic acid the agent will be regarded as an ESX inhibitor. Conversely, ESX agonists will increase ESX binding of its nucleic acid substrate. Methods of assaying for protein/DNA binding interactions are well known to those of skill in the art. Such methods include, for example, DNA bending assays (see, e.g., Wechsler and Dang (1992) *Proc. Natl. Acad. Sci. USA*, 89: 7635–7639 with modifications to prevent anomalous results described by McCormick et al. (1996) *Proc. Natl. Acad. Sci. USA*, 93: 14434–14439), and more traditional binding assays such as transcription factor binding assays (see, e.g., U.S. Pat. Nos. 5,350,835 and 5,563,036). It was a discovery of this invention that the minimal ESX domain necessary for ESX-mediated transactivation is encoded by exon 4 (aa 129–159), an acidic domain containing a central lysine residue (K-145). Subsequent mutations of this domain have established that the central K-145 is essential and provides nearly 1000-fold transactivation potency (relative to a neutral residue placed there). A database search revealed that the exon 4-encoded domain is homologous to the essential core domain of all known Topoisomerase I molecules (cf. Stewart et al, (1996) *J. Biol. Chem.* 271: 7602–7608; Pommier (1996) *Sem. Oncology* 23: 3–10). Since human Topo-I is a critical intracellular target for the newest and most exciting family of camptothecin-like anticancer agents (like Topotecan, CPT-11, 9AC, etc.; see reviews).

This information not only provides important data regarding the molecular transactivation mechanism of ESX, but it suggests that this particular ESX domain may be used to search for or screen (from libraries, e.g., combinatorial libraries of synthetic chemicals and/or natural products) for even newer and more effective and selective anticancer agents. Existing Topo-I agents target a very different, C-terminal conserved domain in the Topo-I enzyme. Prior to this invention there was no specific function attributed to the highly conserved Topo-I Core domain which is homologous to the ESX transactivation domain.

These data also shed light on the functioning of Topo-I (and new ways to inhibit it) as they do on the functioning of ESX. In this regard, this invention provides, in one embodiment, methods of screening for a therapeutic lead compound. The methods involve providing a nucleic acid encoding a polypeptide of ESX exon 4 or a polypeptide sequence of ESX exon 4; (ii) contacting the compound to the nucleic acid or polypeptide sequence; and (iii) detecting binding of the compound to the nucleic acid or polypeptide sequence. Compounds that specifically bind to the exon 4 nucleic acid and/or polypeptide are expected to provide lead compounds for therapeutic evaluation and/or development. Suitable binding assays are described below and are also well known to those of skill in the art.

Similarly, in another related embodiment, this invention provides a method of identifying potential therapeutic targets for drug screening. The method involves: i) identifying a subsequence of the ESX gene or protein necessary for ESX transactivating activity (preferably helicase-like activity); ii) performing a nucleic acid or protein database search to identify other nucleic acids having significant sequence identity with said subsequence whereby said subsequence is identified as a potential therapeutic target for drug screening. In a particularly preferred embodiment, such subsequences will be searched for among known or unknown topoisomerases, gyrases, helicases, and related DNA repair enzymes. Significant sequence identity will generally refer to statistically significant sequence identity, typically greater than about 40%, more preferably greater than about 50%, most preferably greater than about 70%, 80%, 90% or even 95%, across a window of at least about 14 amino acids, more preferably across a window of at least about 16 amino acids, and most preferably across a window of at least about 20, 25, or even 30 amino acids (or corresponding nucleotide window sizes).

B) ESX Modulators for Screening.

Virtually any compound can be screened for ESX modulatory activity. However, it will be appreciated that some compounds are expected to show ESX modulatory activity and these compounds may be preferentially screened. Such compounds include, but are not limited to compounds that specifically target and bind to ESX nucleic acids or polypeptides (e.g., ESX muteins, or ESX antisense molecules).

i) ESX Muteins

It was a discovery of this invention that full-length ESX bends DNA by as much as 80 degrees upon DNA-binding. In contrast, when only the DNA-binding portion of ESX (see, FIG. 5), or any other ETS protein is assessed, only 6–20 degrees of DNA bending is observed (as reported by NMR and X-ray crystallography studies on other truncated ETS proteins). This indicates that a mutated version of a full DNA bending ESX construct can act as a "dominant-negative" transcription factor or fused to a known repression module to produce an agent that will silence ESX regulated genes and turn off potential gene programs necessary for tumor cell invasion and metastasis. Using the sequence information provided herein (e.g., FIG. 5) ESX polypeptide variants can be routinely produced.

For example, it is demonstrated herein that the central $K^{145}$ of exon 4 (aa 129–159) of is essential for ESX transactivation activity and provides nearly 1000-fold transactivation potency (relative to a neutral residue placed there. The mutation of $K^{145}$ to a neutral residue will provide an inactivating (competitive) mutein.

Methods of making other such polypeptide variants (muteins) are well known to those of skill (see, e.g., U.S. Pat. Nos. 5,486,463, 5,422,260, 5,116,943, 4,752,585, 4,518,504). Screening of such polypeptides (e.g., in DNA binding assays or for competitive inhibition of full-length normal ESX polypeptides) can be accomplished with only routine experimentation. Using high-throughput methods, as described herein, literally thousands of agents can be screened in only a day or two.

ii) Antisense Molecules.

ESX gene regulation can be downregulated or entirely inhibited by the use of antisense molecules. An "antisense sequence or antisense nucleic acid" is a nucleic acid is complementary to the coding ESX mRNA nucleic acid sequence or a subsequence thereof. Binding of the antisense molecule to the ESX mRNA interferes with normal translation of the ESX polypeptide.

Thus, in accordance with preferred embodiments of this invention, preferred antisense molecules include oligonucleotides and oligonucleotide analogs that are hybridizable with ESX messenger RNA. This relationship is commonly denominated as "antisense." The oligonucleotides and oligonucleotide analogs are able to inhibit the function of the RNA, either its translation into protein, its translocation into the cytoplasm, or any other activity necessary to its overall biological function. The failure of the messenger RNA to perform all or part of its function results in a reduction or complete inhibition of expression of ESX polypeptides.

In the context of this invention, the term "oligonucleotide" refers to a polynucleotide formed from naturally-occurring bases and/or cyclofuranosyl groups joined by native phosphodiester bonds. This term effectively refers to naturally-occurring species or synthetic species formed from naturally-occurring subunits or their close homologs. The term "oligonucleotide" may also refer to moieties which function similarly to oligonucleotides, but which have non naturally-occurring portions. Thus, oligonucleotides may have altered sugar moieties or inter-sugar linkages. Exemplary among these are the phosphorothioate and other sulfur containing species which are known for use in the art. In accordance with some preferred embodiments, at least one of the phosphodiester bonds of the oligonucleotide has been substituted with a structure which functions to enhance the ability of the compositions to penetrate into the region of cells where the RNA whose activity is to be modulated is located. It is preferred that such substitutions comprise phosphorothioate bonds, methyl phosphonate bonds, or short chain alkyl or cycloalkyl structures. In accordance with other preferred embodiments, the phosphodiester bonds are substituted with structures which are, at once, substantially non-ionic and non-chiral, or with structures which are chiral and enantiomerically specific. Persons of ordinary skill in the art will be able to select other linkages for use in the practice of the invention.

Oligonucleotides may also include species which include at least some modified base forms. Thus, purines and pyrimidines other than those normally found in nature may be so employed. Similarly, modifications on the furanosyl portions of the nucleotide subunits may also be effected, as long as the essential tenets of this invention are adhered to. Examples of such modifications are 2'-O-alkyl- and 2'-halogen-substituted nucleotides. Some specific examples of modifications at the 2' position of sugar moieties which are useful in the present invention are OH, SH, $SCH_3$, F, $OCH_3$, OCN, $O(CH_2)[n]NH_2$ or $O(CH_2)[n]CH_3$, where n is from 1 to about 10, and other substituents having similar properties.

Such oligonucleotides are best described as being functionally interchangeable with natural oligonucleotides or synthesized oligonucleotides along natural lines, but which have one or more differences from natural structure. All such analogs are comprehended by this invention so long as they function effectively to hybridize with messenger RNA of ESX to inhibit the function of that RNA.

The oligonucleotides in accordance with this invention preferably comprise from about 3 to about 50 subunits. It is more preferred that such oligonucleotides and analogs comprise from about 8 to about 25 subunits and still more preferred to have from about 12 to about 20 subunits. As will be appreciated, a subunit is a base and sugar combination suitably bound to adjacent subunits through phosphodiester or other bonds. The oligonucleotides used in accordance with this invention may be conveniently and routinely made through the well-known technique of solid phase synthesis. Equipment for such synthesis is sold by several vendors, including Applied Biosystems. Any other means for such synthesis may also be employed, however, the actual synthesis of the oligonucleotides is well within the talents of the routineer. It is also will known to prepare other oligonucleotide such as phosphorothioates and alkylated derivatives.

iii) Modification of Promoters to Regulate Endogenous ESX Expression.

In still another embodiment, the expression of ESX genes can be altered by altering the endogenous promoter. Methods of altering expression of endogenous genes are well known to those of skill in the art. Typically such methods involve altering or replacing all or a portion of the regulatory sequences controlling expression of the particular gene that is to be regulated. In a preferred embodiment, the regulatory sequences (e.g., the native promoter) upstream of the ESX gene is altered.

This is typically accomplished by the use of homologous recombination to introduce a heterologous nucleic acid into the native regulatory sequences. To down-regulate expression of the ESX gene product, simple mutations that either alter the reading frame or disrupt the promoter are suitable. To upregulate expression of the ESX gene product, the native promoter(s) can be substituted with heterologous promoter(s) that induce higher than normal levels of transcription.

In a particularly preferred embodiment, nucleic acid sequences comprising the structural gene in question or upstream sequences are utilized for targeting heterologous recombination constructs. Suitable upstream and downstream sequences can be readily determined using the information provided herein. Moreover, this invention providers the sequence of both the murine and the human ESX proximal promoter (see, e.g., FIG. 6) readily facilitating modification or replacement of the promoter.

The use of homologous recombination to alter expression of endogenous genes is described in detail in U.S. Pat. No. 5,272,071, WO 91/09955, WO 93/09222, WO 96/29411, WO 95/31560, and WO 91/12650.

iv) Combinatorial Libraries (e.g., Small Organic Molecules)

Conventionally, new chemical entities with useful propel-Lies are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays, as described below to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis by combining a number of chemical "building blocks" such as reagents. For example, a linear combinatorial chemical library such as a polypeptide (e.g., mutein) library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) 37(9): 1233–1250).

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) Int. J. Pept. Prot. Res., 37: 487–493, Houghton et al. (1991) Nature, 354: 84–88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, 26 Dec. 1991), encoded peptides (PCT Publication WO 93/20242, 14 Oct. 1993), random bio-oligomers (PCT Publication WO 92/00091, 9 Jan. 1992), benzodiazepines (U.S. Pat. No. 5,288,514), diversomers such as hydantoins, benzodiazepines and dipeptides (Hobbs et al., (1993) Proc. Nat. Acad. Sci. USA 90: 6909–6913), vinylogous polypeptides (Hagihara et al. (1992) J. Amer. Chem. Soc. 114: 6568), nonpeptidal peptidomimetics with a Beta-D-Glucose scaffolding (Hirschmann et al., (1992) J. Amer. Chem. Soc. 114: 9217–9218), analogous organic syntheses of small compound libraries (Chen et al. (1994) J. Amer. Chem. Soc. 116: 2661), oligocarbamates (Cho, et al., (1993) Science 261: 1303), and/or peptidyl phosphonates (Campbell et al., (1994) J. Org. Chem. 59: 658). See, generally, Gordon et al., (1994) J. Med. Chem. 37:1385, nucleic acid libraries (see, e.g., Strategene, Corp.), peptide nucleic acid libraries (see, e.g., U.S. Pat. No. 5,539,083) antibody libraries (see, e.g., Vaughn et al. (1996) Nature Biotechnology, 14(3): 309–314), and PCT/US96/10287), carbohydrate libraries (see, e.g., Liang et al. (1996) Science, 274: 1520–1522, and U.S. Pat. No. 5,593,853), and small organic molecule libraries (see, e.g., benzodiazepines, Baum (1993) C&EN, January 18, page 33, isoprenoids U.S. Pat. No. 5,569,588, thiazolidinones and metathiazanones U.S. Pat. No. 5,549, 974, pyrrolidines U.S. Pat. Nos. 5,525,735 and 5,519,134, morpholino compounds U.S. Pat. No. 5,506,337, benzodiazepines U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

C) High Throughout Screening

Any of the assays for compounds modulating ESX gene expression and/or ESX protein activity (e.g., binding activity) described herein are amenable to high throughput screening. Preferred assays thus detect enhancement or inhibition of ESX gene transcription, inhibition or enhancement of ESX polypeptide expression, inhibition or enhancement of DNA binding by ESX polypeptide, or inhibition or enhancement of expression of native genes (or reporter genes) under control of the ESX polypeptide.

High throughput assays for the presence, absence, or quantification of particular nucleic acids or protein products are well known to those of skill in the art. Similarly, binding assays and reporter gene assays are similarly well known. Thus, for example, U.S. Pat. No. 5,559,410 discloses high throughput screening methods for proteins, U.S. Pat. No.

5,585,639 discloses high throughput screening methods for nucleic acid binding (i.e., in arrays), while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

D) In vivo Administration of ESX Modulators.

The ESX polypeptides, ESX polypeptide subsequences, anti-ESX antibodies, anti-ESX antibody-effector (e.g., enzyme, toxin, hormone, growth factor, drug, etc.) conjugates or fusion proteins, or other ESX modulators of this invention are useful for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the ESX polypeptides and related compounds described of, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art.

The pharmaceutical compositions of this invention are particularly useful for topical administration to cancers, in particular epithelial cancers, and their precursors (such as ductal carcinoma in situ, DCIS). In another embodiment, the compositions are useful for parenteral administration, such as intravenous administration or administration into a body cavity or lumen of an organ. The compositions for administration will commonly comprise a solution of the ESX polypeptide, antibody or antibody chimera/fusion dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of chimeric molecule in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art and are described in more detail in such publications as *Remington's Pharmaceutical Science,* 15th ed., Mack Publishing Company, Easton, Pa. (1980).

The compositions containing the present ESX polypeptides, antibodies or antibody chimera/fusions, or a cocktail thereof (i.e., with other proteins), can be administered for therapeutic treatments. To treat an epithelial cancer characterized by overexpression of ESX, one can administer an anti-ESX antibody or an abnormal ESX protein that is not biologically active. Such inactive ESX polypeptides can, for example, interfere with binding of native ESX polypeptide to its DNA binding site, or to RNA polymerase or other protein through which the ESX transcription factor activity is mediated.

In therapeutic applications, compositions are administered to a patient suffering from a disease (a., on epithelial cancer) in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the proteins of this invention to effectively treat the patient.

Among various uses of the ESX polypeptides, polypeptide subsequences, anti-ESX antibodies and anti-ESX-effector chimeras/fusions of the present invention are treatment a variety of disease conditions, including cancers such as cancers of the breast, head, neck, ovary, bladder, colon, and the like.

B) Cellular Transformation and Gene Therapy.

The present invention provides packageable human ESX nucleic acids (cDNAs) for the transformation of cells in vitro and in vivo. These packageable nucleic acids can be inserted into any of a number of well known vectors for the transfection and transformation of target cells and organisms as described below. The nucleic acids are transfected into cells, ex vivo or in vivo, through the interaction of the vector and the target cell. The ESX cDNA, under the control of a promoter, then expresses the ESX protein thereby mitigating the effects of absent ESX genes or partial inactivation of the ESX gene or abnormal expression of the ESX gene. For treatment of conditions characterized by excessive ESX expression, the ESX nucleic acids can be modified so as to interfere with ESX biological activity. For example, the ESX nucleic acids can be modified to encode an ESX polypeptide that is not biologically active. Alternatively, an ESX antisense nucleic acid can be administered, either directly or indirectly by expression of an antisense nucleic acid from an expression vector.

Such gene therapy procedures have been used to correct acquired and inherited genetic defects, cancer, and viral infection in a number of contexts. The ability to express artificial genes in humans facilitates the prevention and/or cure of many important human diseases, including many diseases which are not amenable to treatment by other therapies. As an example, in vivo expression of cholesterol-regulating genes, genes which selectively block the replication of HIV, and tumor-suppressing genes in human patients dramatically improves the treatment of heart disease, AIDS, and cancer, respectively. For a review of gene therapy procedures, see Anderson (1992) *Science* 256: 808–813; Nabel and Felgner (1993) *TIBTECH* 11: 211–217; Mitani and Caskey (1993) *TIBTECH* 11: 162–166; Mulligan (1993) *Science* 926–932; Dillon (1993) *TIBTECH* 11: 167–175; Miller (1992) *Nature* 357: 455–460; Van Brunt (1988) *Biotechnology* 6(10): 1149–1154; Vigne (1995) *Restorative Neurology and Neuroscience* 8: 35–36; Kremer and Perricaudet (1995) *British Medical Bulletin* 51(1) 31–44; Haddada et al. (1995) in *Current Topics in Microbiology and Immunology*, Doerfler and Böhm (eds) Springer-Verlag, Heidelberg Germany; and Yu et al, (1994) *Gene Therapy* 1: 13–26.

Delivery of the gene or genetic material into the cell is the first critical step in gene therapy treatment of disease. A large number of delivery methods are well known to those of skill in the art. Such methods include, for example liposome-based gene delivery (Debs and Zhu (1993) WO 93/24640; Mannino and Gould-Fogerite (1988) *BioTechniques* 6(7): 682–691; Rose U.S. Pat. No. 5,279,833; Brigham (1991) WO 91/06309; and Felgner et al. (1987) *Proc. Natl. Acad. Sci. USA* 84: 7413–7414), and replication-defective retroviral vectors harboring a therapeutic polynucleotide sequence as part of the retroviral genome (see, e.g., Miller et al. (1990) *Mol. Cell. Biol.* 10:4239 (1990); Kolberg (1992) *J. NIH Res.* 4:43, and Cornetta et al. (1991) *Hum. Gene Ther.* 2: 215). Widely used retroviral vectors include those based upon murine leukemia virus (MuLV), gibbon ape leukemia virus (GaLV), simian immunodeficiency virus (SIV), human immunodeficiency virus (HIV), and combinations thereof (see, e.g., Buchscher et al. (1992) *J. Virol.* 66(5) 2731–2739; Johann et al. (1992) *J. Virol.* 66 (5):1635–1640; Sommerfelt et al., (1990) *Virol.* 176: 58–59; Wilson et al. (1989) *J. Virol.* 63:2374–2378; Miller-et al. (1991) *J. Virol.* 65:2220–2224; Wong-Staal et al., PCT/US94/05700, Rosenburg and Fauci (1993) in *Fundamental Immunology, Third Edition* Paul (ed) Raven Press, Ltd., New York and the references therein, and Yu et al., (1994) *Gene Therapy supra*).

AAV-based vectors are also used to transduce cells with target nucleic acids, e.g., in the in vitro production of nucleic acids and peptides, and in in vivo and ex vivo gene therapy procedures (see, West et al. (1987) *Virology* 160: 38–47; Carter et al. (1989) U.S. Pat. No. 4,797,368; Carter et al. WO 93/24641 (1993); Kotin (1994) *Human Gene Therapy* 5: 793–801; Muzyczka (1994) *J. Clin. Invst.* 94: 1351 and Samulski (supra) for an overview of AAV vectors. Construction of recombinant AAV vectors are described in a number of publications, including Lebkowski, U.S. Pat. No. 5,173, 414; Tratschin et al. (1985) *Mol. Cell. Biol.* 5(11): 3251–3260; Tratschin, et al. (1984) *Mol. Cell. Biol.,* 4:2072–2081; Hermonat and Muzyczka (1984) *Proc. Natl. Acad. Sci. USA,* 81:6466–6470; McLaughlin et al. (1988) and Samulski et al. (1989) *J. Virol.,* 63: 3822–3828. Cell lines that can be transformed by rAAV include those described in Lebkowski et al. (1988) *Mol. Cell Biol.,* 8:3988–3996.

C) Ex Vivo Transformation of Cells.

Ex vivo cell transformation for diagnostics, research, or for gene therapy (e.g., via re-infusion of the transformed cells into the host organism) is well known to those of skill in the art. In a preferred embodiment, cells are isolated from the subject organism, transfected with the ESX gene or cDNA of this invention, and re-infused back into the subject organism (e.g., patient). Various cell types suitable for ex vivo transformation are well known to those of skill in the art. Particular preferred cells are progenitor or stem cells (see, e.g., Freshney et al., (1994) *Culture of Animal Cells, a Manual of Basic Technique*, third edition Wiley-Liss, New York) and the references cited therein for a discussion of how to isolate and culture cells from patients).

As indicated above, in a preferred embodiment, the packageable nucleic acid encodes an ESX polypeptide under the control of an activated or constitutive promoter. The transformed cell(s) express functional ESX polypeptide which mitigates the effects of deficient or abnormal ESX gene expression. Alternatively, as described above, the transformed cells can express nonfunctional ESX polypeptide that interferes with the biological activity of endogenous ESX polypeptide, thus mitigating the effects of abnormal overexpression of ESX polypeptide in, for example, cancer cells.

For some embodiments, stem cells are used in ex-vivo procedures for cell transformation and gene therapy. One advantage for some applications to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-g and TNF-a are known (see, Inaba et al. (1992) *J. Exp. Med.* 176, 1693–1702).

Stem cells are isolated for transduction and differentiation using known methods. For example, in mice, bone marrow cells are isolated by sacrificing the mouse and cutting the leg bones with a pair of scissors. Stem cells are isolated from bone marrow cells by panning the bone marrow cells with antibodies which bind unwanted cells, such as CD4$^+$ and CD8$^+$ (T cells), CD45$^+$ (panB cells), GR-1 (granulocytes), and Iad (differentiated antigen presenting cells). For an example of this protocol see, Inaba et al. (1992) *J. Exp. Med.* 176, 1693–1702.

In humans, bone marrow aspirations from iliac crests are performed e.g., under general anesthesia in the operating room. The bone marrow aspirations is approximately 1,000 ml in quantity and is collected from the posterior iliac bones and crests. If the total number of cells collected is less than about 2×10$^8$/kg, a second aspiration using the sternum and anterior iliac crests in addition to posterior crests is performed. During the operation, two units of irradiated packed red cells are administered to replace the volume of marrow taken by the aspiration. Human hematopoietic progenitor and stem cells are characterized by the presence of a CD34 surface membrane antigen. This antigen is used for purification, e.g., on affinity columns which bind CD34. After the bone marrow is harvested, the mononuclear cells are separated from the other components by means of ficol gradient centrifugation. This is performed by a semi-automated method using a cell separator (e.g., a Baxter Fenwal CS3000+ or Terumo machine). The light density cells, composed mostly of mononuclear cells are collected and the cells are incubated in plastic flasks at 37° C. for 1.5 hours. The adherent cells (monocytes, macrophages and B-Cells) are discarded. The non-adherent cells are then collected and incubated with a monoclonal anti-CD34 antibody (e.g., the murine antibody 9C5) at 4° C. for 30 minutes with gentle rotation. The final concentration for the anti-CD34 antibody is 10 μg/ml. After two washes, paramagnetic microspheres (Dyna Beads, supplied by Baxter Immunotherapy Group, Santa Ana, Calif.) coated with sheep antimouse IgG (Fc) antibody are added to the cell suspension at a ratio of 2 cells/bead. After a further incubation period of 30 minutes at 4° C., the rosetted cells with magnetic beads are collected with a magnet. Chymopapain (supplied by Baxter Immunotherapy Group, Santa Ana, Calif.) at a final concentration of 200 U/ml is added to release the beads from the CD34$^+$ cells. Alternatively, and preferably, an affinity column isolation procedure can be used which binds to CD34, or to antibodies bound to CD34 (see, the examples below). See, Ho et al. (1995) *Stem Cells* 13 (suppl. 3): 100–105. See also, Brenner (1993) *Journal of Hematotherapy* 2: 7–17. In another embodiment, hematopoetic stem cells are isolated from fetal cord blood. Yu et al. (1995) Proc. Natl. Acad. Sci. USA, 92: 699–703 describe a preferred method of transducing CD34$^{0+}$ cells from human fetal cord blood using retroviral vectors.

For some purposes, non-stem cells are preferred for ex vivo treatments using ESX nucleic acids. For example, where it is desirable to have the ESX product expressed transiently, mortal cells that do not differentiate are preferred carriers of ESX nucleic acids.

D) In Vivo Transformation.

Vectors (e.g., retroviruses, adenoviruses, liposomes, etc.) containing therapeutic nucleic acids can be administered directly to the organism for transduction of cells in vivo. Administration is by any of the routes normally used for introducing a molecule into ultimate contact with blood or tissue cells. The packaged nucleic acids are administered in any suitable manner, preferably with pharmaceutically acceptable carriers. Suitable methods of administering such packaged nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

The packaged nucleic acids, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the packaged nucleic acid with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of packaged nucleic acid can be presented in unit-dose or multi-dose sealed containers, such as ampoules and vials.

Injection solutions and suspensions can be prepared from sterile powders, granules, and tablets of the kind previously described. Cells transduced by the packaged nucleic acid as described above in the context of ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis ESX predilection or onset, the physician evaluates circulating plasma levels of the vector, vector toxicities, progression of the disease, and the production of anti-vector antibodies. In general, the dose equivalent of a naked nucleic acid from a vector is from about 1 mg to 100 mg for a typical 70 kilogram patient, and doses of vectors which include a retroviral particle are calculated to yield an equivalent amount of therapeutic nucleic acid.

For administration, inhibitors and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

In a preferred embodiment, prior to infusion, blood samples are obtained and saved for analysis. Between $1\times10^8$ and $1\times10^{12}$ transduced cells are infused intravenously over 60–200 minutes. Vital signs and oxygen saturation by pulse oximetry are closely monitored. Blood samples are obtained 5 minutes and 1 hour following infusion and saved for subsequent analysis. Leukopheresis, transduction and reinfusion can be repeated are repeated every 2 to 3 months. After the first treatment, infusions can be performed on a outpatient basis at the discretion of the clinician. If the reinfusion is given as an outpatient, the participant is monitored for at least 4, and preferably 8 hours following the therapy.

Transduced cells are prepared for reinfusion according to established methods. See, Abrahamsen et al. (1991) *J. Clin. Apheresis*, 6: 48–53; Carter et al. (1988) *J. Clin. Arpheresis*, 4:113–117; Aebersold et al. (1988) *J. Immunol. Meth.*, 112: 1–7; Muul et al. (1987) *J. Immunol. Methods*, 101: 171–181 and Carter et al. (1987) *Transfusion* 27: 362–365. After a period of about 2–4 weeks in culture, the cells should number between $1\times10^8$ and $1\times10^{12}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent.

EXAMPLES

The following examples are offered to illustrate, but not to limit the present invention.

Example 1

Cloning and Expression of a Human ESX Gene

This example describes the isolation of a complete human ESX cDNA sequence that encodes a putative protein of 371 amino acids. Briefly, a highly conserved eight amino acid motif within the carboxy (C)-terminal region of the ETS domain was identified and this motif was used to search a database of human epithelium expressed sequence tags (ESTs). The database (dbEST) contained >250,000 largely anonymous ESTs (Lennon et al. (1996) *Genomics* 33: 151–152. This search identified a partial cDNA sequence from fetal liver-spleen (GenBank locus T78501). Within this same database, were found two other unidentified but nearly identical partial sequences from normal mammary epithelium (GenBank locus R73021) and adult pancreas (GenBank locus T27397). Human placental polyA+ mRNA was used to generate a full-length cDNA sequence.

Experimental Procedures
Cloning of EST cDNA
The Basic Local Alignment Search Tool (BLAST) was used to search a database of expressed sequence tags (EST) using nucleotides derived from human Ets-2 that encode a highly conserved eight amino acid motif within the carboxy terminal region of the ETS domain (MNYEKLSR). The BLAST algorithm is described in Altschul et al. (1990) *J. Mol. Biol.* 215: 403. This search identified a partial cDNA sequence from fetal liver-spleen (GenBank locus T78501) as a putative new member of the Ets family that was named ESX. Made available by I.M.A.G.E. Consortium and commercially obtained (Research Genetics, Inc.), this 1.1 kb partial cDNA sequence derived from fetal liver-spleen contains a polyA tail, approximately 0.7 kb of 3' untranslated sequence and a 5' region encoding the C-terminal 126 amino acids of ESX. Re-sequencing of T78501 revealed several errors in its original GenBank sequence that would have disrupted the reading frame. A 5' RACE procedure (Frohman (1990) *RACE: Rapid amplification of cDNA ends*, p 28 in PCR Protocols: A guide to methods and applications, Innis, et al., Eds. Academic Press, San Diego, Calif.) was performed using the Marathon cDNA amplification kit (Clontech Laboratories, Inc.) using placental polyA mRNA to clone the remaining 5' portion of ESX cDNA, which was estimated to be approximately 0.8 kb. Automated DNA sequencing of three independent clones of the expected length yielded identical results and 5' cDNA termination sites within 30 bases of one another. Melding these sequences with the amended T78501 sequence produced the open reading frame as shown in SEQ ID NO:1. To identify ESX domain homologies, performed BLAST searches of the SWISS-PROT and PIR protein databases were performed.

ESX Polypeptide Production, DNA Binding Assay, and DNA Footprinting Assay

Using primers incorporating the initiating methionine or the termination codon of ESX and designed with NheI and HindIII sites, respectively, PCR amplification was performed on double stranded placental cDNA (Clontech) to produce a full-length ESX cDNA product which was subsequently cloned into the NheI and HindIII sites of a pRSETA His-tag expression plasmid (Invitrogen). Following sequence verification, an ESX expression clone in BL21 (DE3)pLysS cells was used to produce ESX protein following 8M urea bacterial extraction, purification on ProBond resin (Invitrogen), and dialysis against PBS containing 10% glycerol. SDS polyacrylamide gel analysis indicated a 42 kDa protein with >90% purity.

Electrophoretic mobility shift assay (EMSA) was performed as previously described (Scott et al. (1994) *J. Biol. Chem.* 269: 19848–19858), using approximately one ng of ESX protein per condition and 0.3 pmol of end-labeled TA5 probe (+cold competitor). TA5 is a duplexed 31-mer oligonucleotide from the HER2/neu promoter, extending from −50 bp to −20 bp relative to the major transcriptional start site, that includes an Ets response element.

DNase I footprinting was performed on a 125 bp BssHII/SmaI fragment from the HER2/neu promoter, labeled on the antisense strand at the SmaI site. Reactions contained ~10 ng of ESX protein with 1 unit of DNase-I acting for 1 min at room temperature. Reaction products containing ESX were electrophoresed on a 6% denaturing gel alongside a control reaction lane (minus ESX, lane C).

Trans-Activation of Ets-Responsive Gene Expression by ESX.

Cultured COS cells were transiently cotransfected by calcium phosphate precipitation as previously described (Scott et al. (1994) *J. Biol. Chem.* 269: 19848–19858) using pcDNA1/Amp (Invitrogen) to express full-length ESX protein and either the thymidine kinase minimal promoter-CAT vector (pBLCAT5, from American Type Culture Collection) enhanced with 3 tandem (head-to-tail) upstream copies of TA5 (p3TA5-BLCAT5) or a 700 bp AflII/NcoI fragment from the HER2/neu promoter (containing two other putative Ets response elements upstream of the TA5 sequence) inserted into pCAT-Basic (Promega) to give pHER2-CAT. Mutant reporter plasmids, p3TA5P-BLCAT5 and pHER2m-CAT, were similarly constructed with the former possessing a GGAA to GAGA mutation within each of the tandem repeats and the latter retaining the two upstream promoter response elements intact but possessing a GGAA to TTAA Ets response element mutation within the TA5 sequence. Transfections, using 0.5 mg of reporter and 5 mg of expression plasmid, were repeated at least three times with the mean values (+SD) of CAT reporter activity (arbitrary units) as shown.

Chromosomal Localization.

Metaphase chromosomal localization and interphase copy number of ESX were determined by FISH analysis with a genomic ESX P1 clone, using a previously described technique (Stokke et al. (1995) *Genomics* 26: 134–137).

Northern Hybridization.

Total cellular RNA was prepared by guanidinium isothiocyanate extraction (pH 5.5) as described previously (Scott et al., supra.) and blotted onto nylon membranes following electrophoresis through 1% formaldehyde agarose gels (~20 mg per lane). All blots were probed with a randomly primed 400 bp cDNA fragment from the C-terminal ESX coding region, and given final washes at 65° C. in 0.2×SSC. Short exposure of the autoradiograph in FIG. 9c (vs. FIG. 9b) was used to demonstrate HRG induction of ESX in the overexpressing SK-BR-3 cells.

Detection of ESX Expression by In Situ Hybridization

Figure 10A:
FIGS. 10a and 10b show ESX expression detected by in situ hybridization of normal and malignant breast tissue samples. Overexpression of ESX in a representative sample of HER2-positive ductal carcinoma in situ (DCIS) (FIG. 10a, 40× magnification) relative to lower level ESX expression in a representative sample of normal mammary ductal epithelium (FIG. 10b, 40× magnification).
Figure 10B:
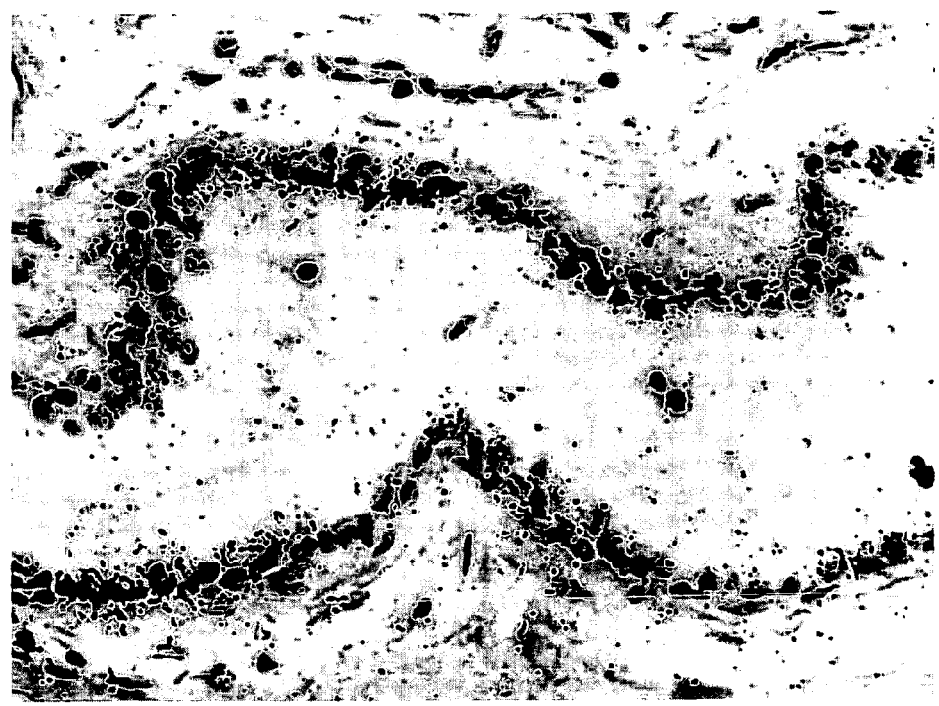

ESX sense and antisense riboprobes for in situ hybridization were generated by $^{35}$S-labeling and run-off transcription using T7 or T3 RNA polymerase, respectively, from pT7T3 (Pharmacia) containing a 700 bp fragment of 3' untranslated ESX cDNA. Using previously described techniques (Wilkinson (1992) In situ hybridization: a practical approach, IRL Press, Oxford), tissue hybridization and autoradiography were performed on thin sections of paraffin-embedded samples of normal mammary epithelium (n=3) and DCIS breast tumors (n=10). Samples were chosen according to their previously determined EHER2/neu overexpression and amplification status (Liu et al. (1992) Oncogene 7: 1027–1032) and for their RNA integrity and comparable levels of glyceraldehyde-3-phosphate dehydrogenase (GAPDH) expression, as determined by preliminary in situ hybridization with an antisense probe for GAPDH. FIGS. 10a and 10b show only the antisense riboprobe signals resulting from ESX transcripts in the underlying hematoxylin-counterstained epithelial cells. ESX sense riboprobe was used to control for non-specific hybridization and autoradiography background signal using adjacent sections from each sample. The density of this background signal (from sense riboprobe) was nearly identical for the representative samples shown in this figure, representing less than one-tenth the antisense riboprobe signal density over the epithelial cells shown in FIG. 10b and comparable to that over the acellular stromal component of each sample.

Preparation of Anti-ESX Antiserum.

A peptide fragment consisting of the sixteen carboxy-terminal amino acids of ESX was synthesized for use as an ESX antigen in rabbits. An amino-terminal cysteine was introduced to allow coupling of the peptide to a carrier protein (KLH). To obtain anti-ESX antibodies, total IgG from immunized rabbits was affinity purified on a column to which the ESX carboxy-terminal peptide fragment was bound.

Results and Discussion

Cloning of a Human ESX cDNA.

The nucleotide and deduced amino acid sequences of a human ESX cDNA are shown in FIG. 1. The cDNA includes an open reading frame that encodes a 371 amino acid ESX protein as shown in FIG. 2a. The C-terminal ETS DNA binding domain of ESX (aa 274–354) contains 27 of the 38 most highly conserved (consensus) residues found in the DNA-binding domain of all Ets family members (FIG. 2d). This domain in ESX has its greatest homology with the Drosophila E74/human Elf-1 subfamily (nearly 50% identity, 70% similarity), although ESX has no homology with E74/Elf-1 outside the Ets DNA binding domain. The most obvious structural differences distinguishing ESX from other Ets family members are the five non-conservative changes in its DNA-binding domain consensus residues, including three within the first helix (a1) that enhance basicity in a region likely to make critical contact with the minor groove phosphate backbone of bound DNA (Werner et al. (1995) Cell 83: 761–771; Kodandapani et al. (1996) Nature 380: 456–460). Therefore, ESX may be assigned to the E74/Elf-1 subfamily on the basis of its sequence homology within the ETS domain (Lautenberger et at (1992) Oncogene 7: 1713–1719; Laudet et al.(1993) Biochem. Biophys. Res. Commun. 190: 8–14; Degnan et al. (1993) Nucl. Acids Res. 21: 3479–3484; Wasylyk et al. (1993) Eur. J. Biochem. 211: 7–18; Janknecht and Nordheim (1993) Biochem. Biophys. Acta. 1155: 346–356). In contrast to its two other subfamily members, however, ESX possesses an amino (N)-terminal A-region or Pointed domain, a helix-loop-helix structure that has been conserved from Drosophila to humans and retained within subfamilies remote to E74/Elf-1 (Lautenberger et al., supra.; Wasylyk et al, supra.; Klambt (1993) Development 117: 163–176). The A-region in ESX (aa 64–103) is most similar to that found in Ets-1 (aa 69–106) with 65% similarity and 40% identity, including 7 of 9 consensus A-region residues (FIG. 2b).

Additional features within ESX highlight the known plasticity of Ets proteins in regions outside of their ETS domain, reflecting >500 million years of evolutionary recombination and exon shuffling (Lautenberger et al., supra.; Laudet et al., supra.; Degnan et al., supra.; Wasylyk et al., supra.). ESX has one of the shortest C-terminal tails (16 aa) of all Ets family members. While this terminal sequence has no significant homology to any known eukaryotic gene product, it is over 50% identical and 85% similar to a highly conserved element within the Ross River (aa 194–207) and Semliki Forest (aa 197–210) virus-encoded nsP1 protein, which is required for membrane-bound initiation of RNA synthesis, replication and the subsequent pathogenicity of these New World RNA alphaviruses (Strauss and Strauss (1994) Microbiological Rev. 58: 491–562). Contained within the N-terminal flanking region of the ESX DNA-binding domain is a serine-rich track of 51 residues (aa 188–238) that is 35% identical to the conserved polyserine transactivating domain of the lymphocyte-restricted HMG-box protein, SOX4 (aa 370–420) (Vande Wetering et al. (1993) EMBO J. 12: 3847–3854). Polyserine domains are known to act as strong transactivators, presumably, as in the case of p65NF-kB (aa 530–560), by forming amphipathic helical structures in which the serines are clustered opposite a hydrophobic face (Seipel et al. (1992) EMBO J. 11: 4961–4968; Schmitz and Baeuerle (1991) EMBO J. 10: 3805–3817), as shown in a helical wheel model of the serine box in ESX (FIG. 2c).

ESX Binding to and Transactivation of HER2/neu Ets Response Element.

Figure 8A:
FIGS. 8a through 8e show the results of DNA binding and transactivation by recombinant ESX gene product, as well as chromosomal localization and copy number of the ESX gene.

Earlier studies have demonstrated that the HER2/neu oncogene, which is activated by overexpression in >40% of DCIS early breast tumors (Liu et al., supra.), contains a highly conserved Ets responsive element in its proximal promoter (Scott et al., supra.). Therefore, an oligonucleotide (TA5) containing the Ets response element from HER2/neu was used to assess DNA-binding and transactivation by ESX. Bacterially expressed full-length ESX demonstrates high-affinity, sequence-specific binding to TA5 by electrophoretic mobility shift assay (EMSA), as shown in FIG. 8a. Unlike EMSA results for other Ets proteins known to contain flanking regions that restrict DNA-binding (Jonsen et al. (1996) Mol. Cell. Biol. 16: 2065–2073), full-length ESX binds DNA with comparable affinity to that of truncated ESX (aa 271–371), consisting primarily of the ESX DNA-binding domain. As seen with other Ets factors, DNA probes with mutations in the GGAA Ets core of TA5 fail to compete against TA5 for ESX binding, while those with mutations flanking the GGAA core are relatively effective at competing for ESX binding.

Figure 8B:
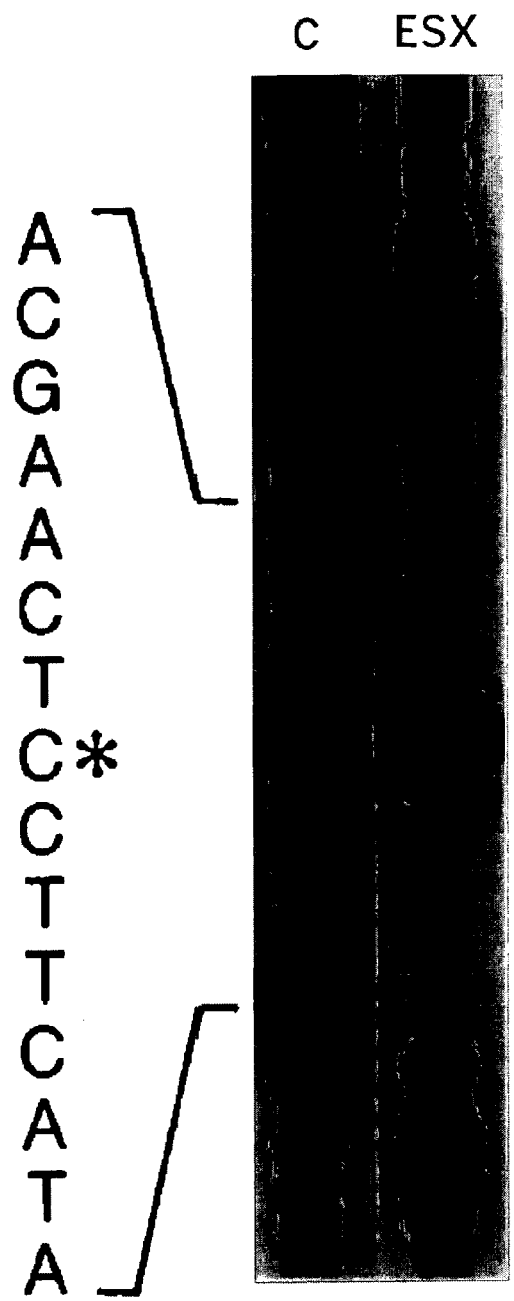

To confirm that ESX binds DNA in an Ets-like manner, ESX footprinting was performed on a larger HER2/neu promoter fragment overlapping the TA5 sequence and its GGAA core response element. Characteristic of DNA-bound Ets proteins, ESX produces a DNase-I hypersensitive site embedded within a footprint on the antisense strand of the core response element (FIG. 8b).

Figure 8C:
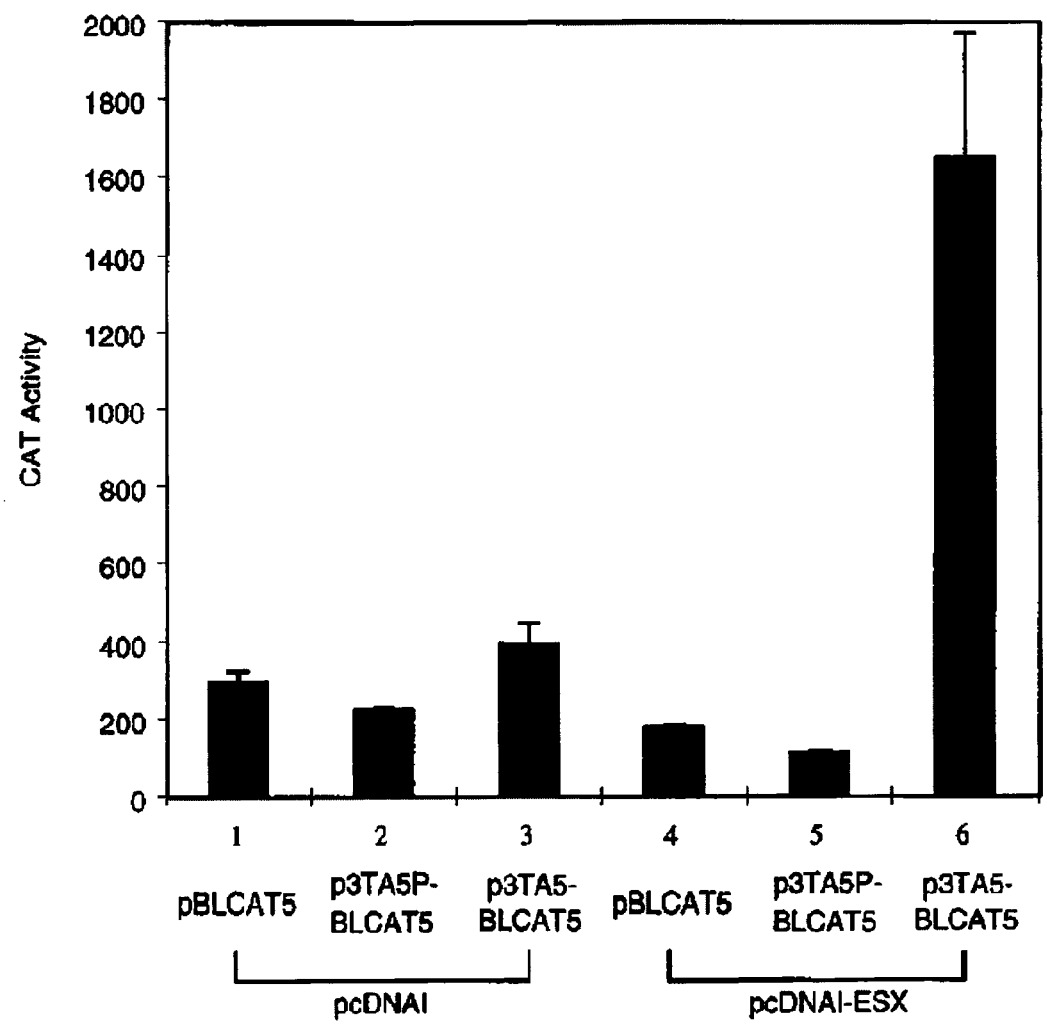

The transactivating potential of ESX was then determined by cotransfecting COS cells with an ESX expression plasmid and either of two different Ets-responsive reporter genes: a minimal promoter construct enhanced by 3 tandem head-to-tail copies of TA5 from the HER2/neu promoter, or ~0.7 kb of the wild-type HER2/neu promoter driving the chloramphenicol acetyl transferase (CAT) reporter gene. Exogenously introduced ESX significantly increases CAT expression from both constructs, but only when the core Ets response element is intact and not mutated, confirming the Ets-specific transactivating potential of ESX (FIG. 8c).

Chromosomal Localization.

To obtain further insight into the evolutionary mechanisms of Ets dispersion during the metazoan radiation of this multigene family, we mapped the chromosomal location of the human ESX gene and found that the gene is located next an unrelated subfamily member. About 10 of the known human Ets genes have been chromosomally mapped and half of these occur as a tandem linkage of dissimilar subfamily members at two general loci (21q22 for Ets2, Erg, and GABPa; 11q23 for Ets1 and Fli1), supporting a proposed model in which duplication of an ancestral Ets was followed by duplication and transposition of the Ets pair to another chromosome (Lautenberger et al., supra.; Laudet et al., supra.; Degnan et al., supra.; Wasylyk et al., supra.).

Figure 8D:
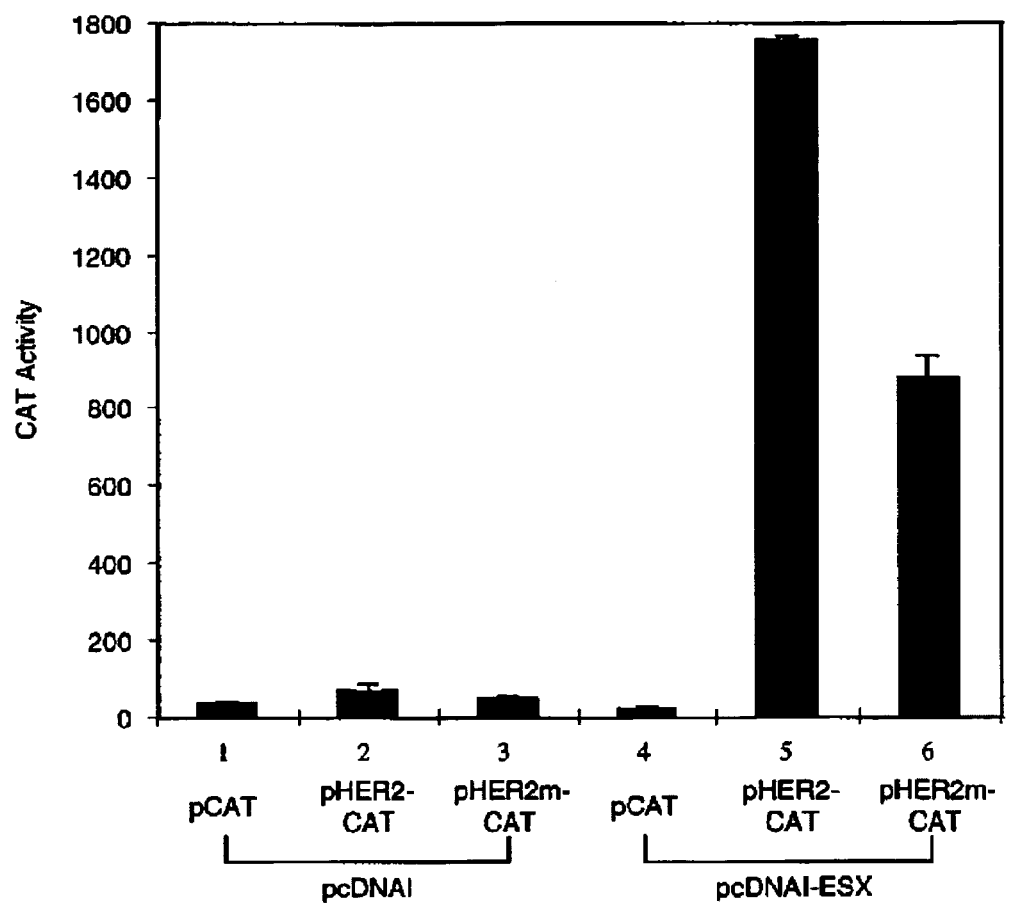
Figure 8E:
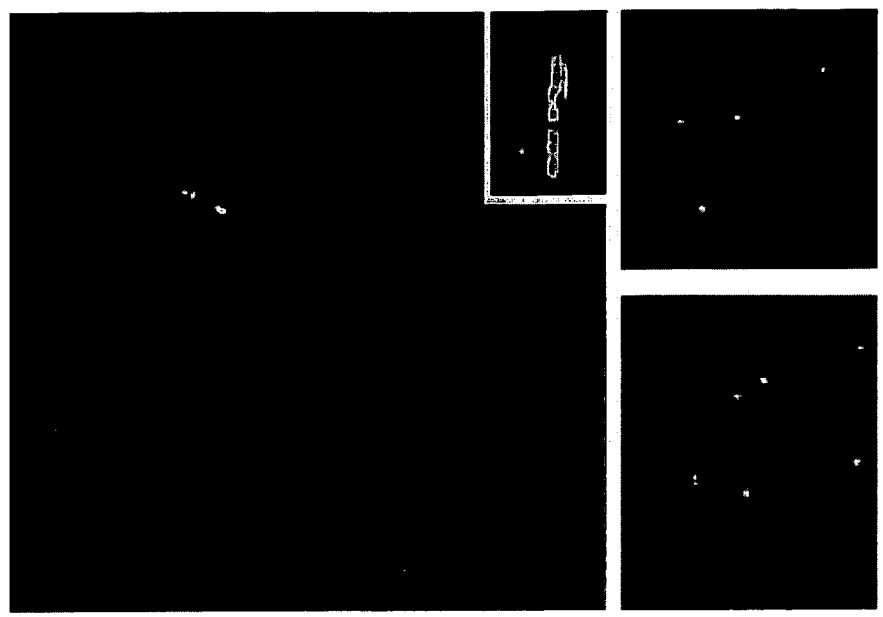

An ESX clone isolated from an arrayed P1 library was used to map ESX to chromosome 1q32 by fluorescence in situ hybridization (FISH) (FIG. 8d). Since SAP1 (also known as ELK4, a member of the SAP/Elk/Net subfamily) was recently mapped to 1q32 (Shipley et al. (1994) *Genomics* 23: 710–711; Giovane et al. (1995) *Genomics* 29: 769–772), ESX and SAP1 now represent the third known set of tandemly linked human Ets genes. While the chromosomal location of Elf-I (subfamily homolog of ESX) is not presently known, it is tempting to speculate that it will be linked to another SAP/Elk/Net subfamily member, in accordance with the evolutionary model for the generation of the Ets-1/Fli-1 and Ets-2/Erg loci.

Southern blotting suggested the presence of excess ESX gene copies in several breast cancer cell lines known for their amplification of HER2/neu (e.g. SK-BR-3, BT-474). Therefore, FISH analysis was also performed on these cells. As shown in FIG. 8d, ESX amplification in these cell lines results predominantly from an increase in chromosome 1q copy number (aneusomy). While gene amplification is not thought to be a common mechanism by which Ets proto-oncogenes become activated (Wasylyk et al., supra.; Janknecht and Norheim, supra.), multiple copies of DNA sequences mapping across the 1q32 locus can be observed in about 50% of early breast tumors (Isola et al. (1995) *Am. J. Pathol.* 147: 905–911). Apart from two other more centromeric proto-oncogenes on this chromosome arm, SKI at 1q22–24 and TRK at 1q23–24 (Chaganti et al. (1986) *Cytogenet. Cell Genet.* 43: 181–186; Morris et al. (1991) *Oncogene* 6: 1093–1095, ESX and SAP1 represent likely oncogene candidates accounting for this 1q amplification in human breast tumors.

Expression of ESX

Figure 9A:
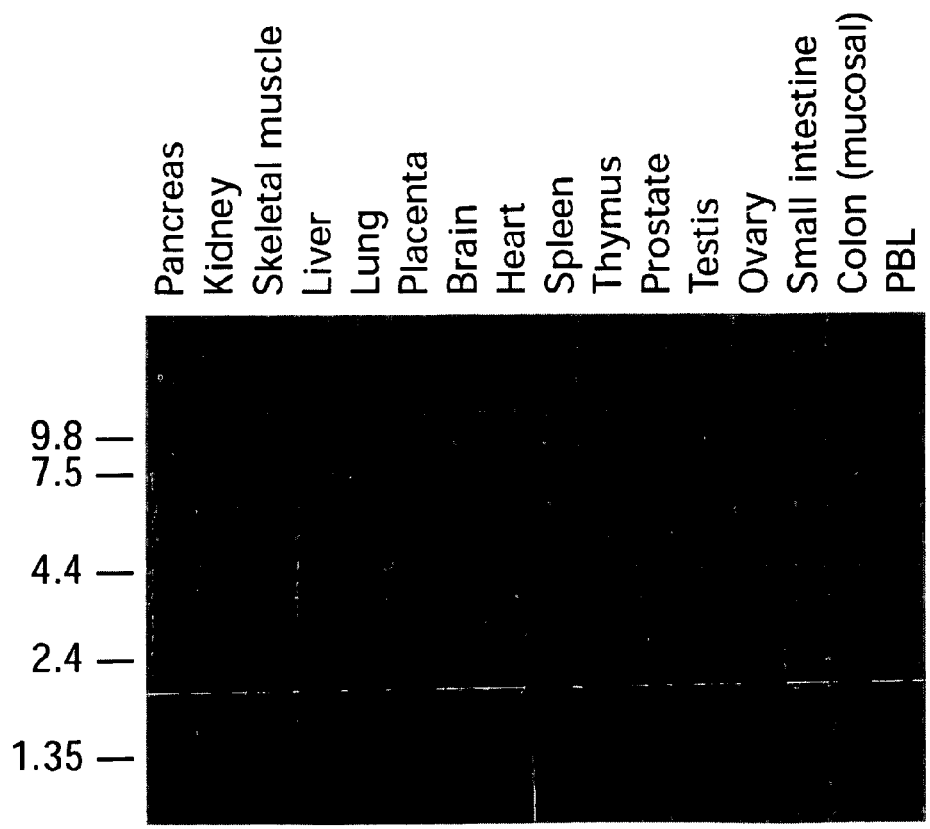
FIGS. 9a, 9b, and 9c show Northern blot detection of ESX transcripts in normal and malignant human epithelial cells, and heregulin induction of ESX expression in breast carcinoma cells.

Many human Ets exhibit a tissue-restricted pattern of gene expression, with some family members showing greater tissue specificity than others (Wasylyk et al, supra.; Janknecht and Norheim, supra.). Northern blots of normal human tissue (FIG. 9a) demonstrate that ESX mRNA expression is restricted to tissues of epithelial origin, with little if any expression detectable in testes, ovary, brain, skeletal muscle, or lympho-hematopoietic tissues (spleen, thymus, white blood cells). PEA3, by comparison, the only other epithelium-restricted Ets, is expressed in a subset (5 of 9) of the ESX-positive tissues (data not shown); expression of both in normal heart leaves open to question the endo-, myo-, or peri-cardial component of this tissue that is the source of ESX and PEA3 transcripts.

Figure 9B:
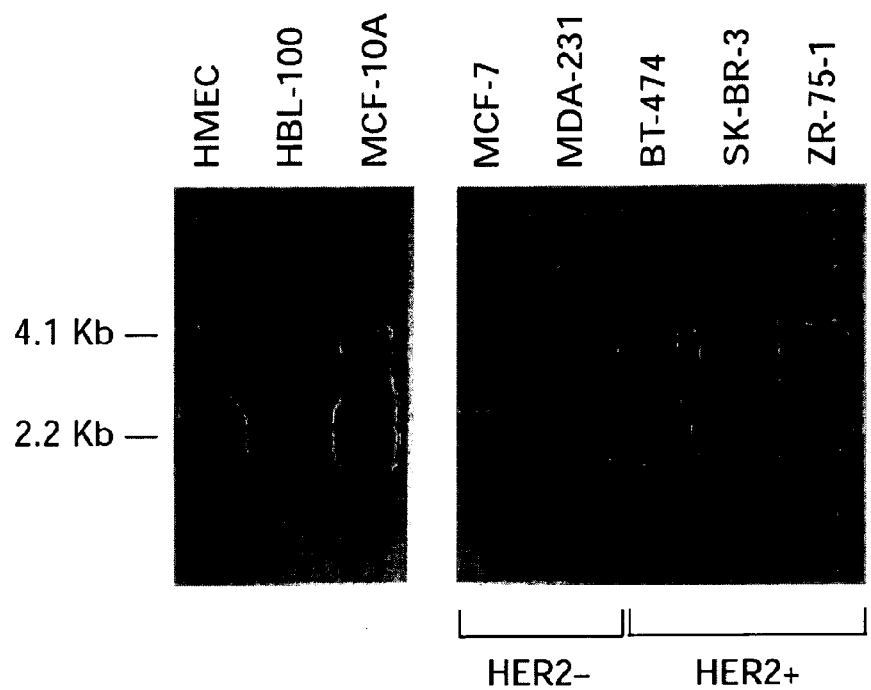
Figure 9C:
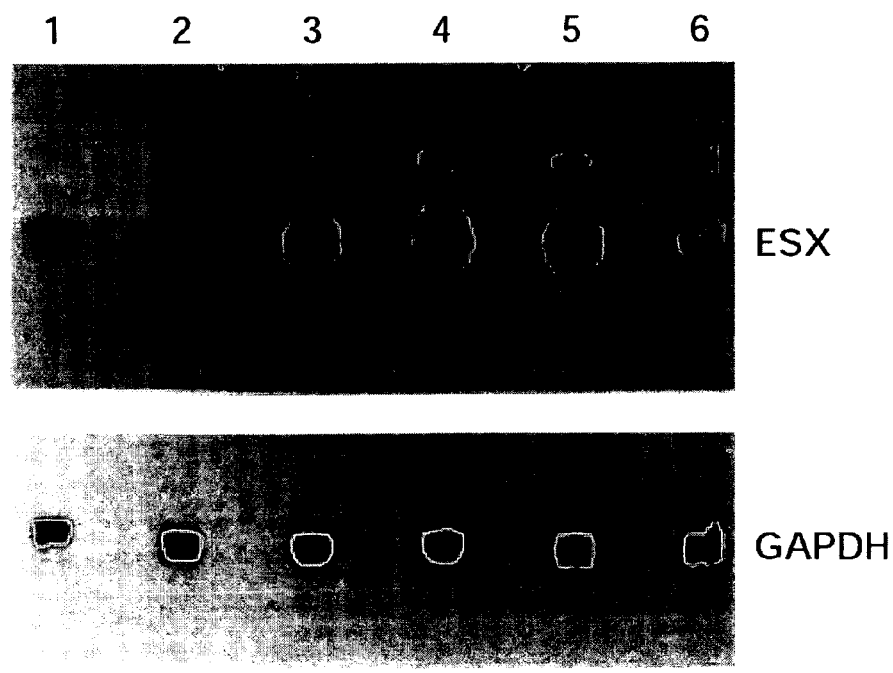

When a panel of human breast cancer cell lines was compared for ESX expression with normal human mammary epithelial cells (HMEC), ESX mRNA was increased in the HER2/neu-positive tumor lines and not increased in the HER2/neu-negative lines (FIG. 9b). Two immortalized but non-transformed mammary cell lines (HBL100, MCF10A) expressed ESX mRNA at levels similar to or below that of HMEC. To explore the possible relationship between ESX overexpression and HER2/neu activation, ESX mRNA was measured in cultured SK-BR-3 cells after treatment with the ligand heregulin-b11–244 (HRG), known to initiate mitogenic signaling in these cells by activation of HER2/neu receptor tyrosine kinase in association with ErbB3 (Holmes et al. (1992) *Science* 256: 1205–1210; Li et al. (1996) *Oncogene* 12: 2473–2477). As shown in FIG. 9c, ESX mRNA increased within 15 min of HRG treatment, achieving peak levels between 60 and 120 min. These results indicate that ESX induction is an immediate early gene response to HER2/neu activation, supporting a signaling link between ESX and HER2/neu gene function.

Since HER2/neu activation occurs early during human breast tumorigenesis and with development of DCIS, evidence of early ESX overexpression was screened for by in situ hybridization in DCIS tumor samples previously characterized as HER2/neu-positive with regard to amplification and overexpression relative to that of normal breast epithelium (Liu et al., supra.). FIGS. 10a and 10b demonstrates that ESX expression was restricted to normal and malignant mammary ductal epithelium with no ESX expression detectable in breast stroma, including its reticulo-endothelial cell and inflammatory/lymphocytic cell components. Consistent with ESX overexpression observed in HER2/neu amplified breast cancer lines, ESX transcript levels in HER2/neu-positive DCIS (FIG. 10a) were markedly increased relative to that of normal breast epithelium (FIG. 10b). These tissue hybridization studies indicate that overexpression of ESX, as with HER2/neu, may occur early during development of human breast tumors.

Since ESX can transactivate the HER2/neu promoter, one potential mechanistic link may be explored by interfering with transcriptional regulation at the Ets response element on this promoter (Noonberg et al. (1994) *Gene* 149: 123–126). Also, preliminary studies suggest that activated HER2/neu increases Ets-mediated gene expression via Ras signaling and that this can lead to feedback upregulation of Ets transcription (Galang et al. (1996) *J. Biol. Chem.* 271: 7992–7998; O'Hagan et al. (1996) *Amer. Assoc. Cancer Res.* 37: 3575. Thus, there is compelling rationale to establish the prevalence and mechanistic role of ESX overexpression in breast tumors as well as other human malignancies of epithelial origin.

Anti-ESX Antibodies.

In a Western blot analysis, anti-ESX polyclonal antibodies prepared as described above specifically recognized purified recombinant ESX protein (~42 kD), as well as a similar sized protein in whole cell extracts. The intensity of the ESX band in samples prepared from whole cell extracts was correlated with cellular ESX mRNA levels.

The anti-ESX antibodies also function to immunoprecipitate a single ~42 kD ESX protein band from 35S metabolically labeled cells.

Example 2

Cloning and Analysis of Murine ESX

A λFIX2 genomic library from strain 129 mouse DNA was screened using a 5' cDNA probe from hESX to isolate a clone from which a 7,751 bp fragment was subcloned into Bluescript and sequenced. A fully encoding mESX cDNA clone was derived from total RNA of 129 mouse ES cells by reverse transcription PCR (RT-PCR) using specific primers extending 5' and 3' from the putative ATG-start and TAA-stop codons, respectively of the genomic sequence. A Bluescript subclone containing this 1,116 bp mESX cDNA was similarly sequenced. All sequencing was performed on an ABI Prism Automated DNA sequencer (model 377) using 3'-dye labeled ddNTP terminators. The full length mouse ESX genomic sequence is provided in SEQ ID NO: 11.

Figure 7:
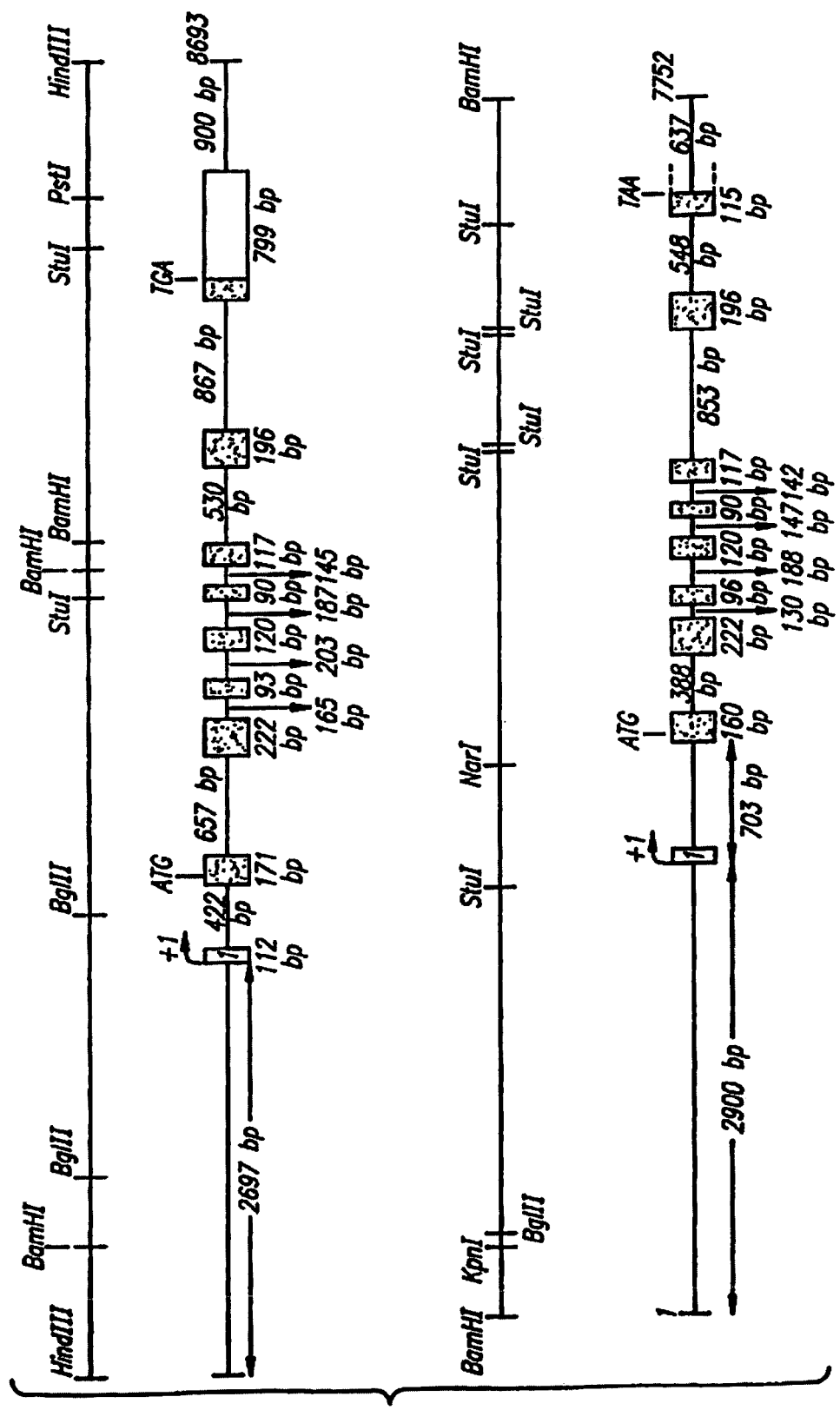
FIG. 7 illustrates the mouse ESX (mESX) and human ESX (hESX) genomic DNA structure.

Alignment of genomic and cDNA mESX sequences as well as comparison of mESX vs hESX homologous sequences were used to determine exon and intron boundaries (see, FIG. 7). Conserved murine and human promoter elements as well as putative amino acid domain homologies were identified from PIR-protein, SWISS-PROT, and PROSITE databases by GCG computer search (Genetics Computer Group, Wisconsin Package 3.0, Madison, Wis.).

A 7.8 kb mESX genomic clone was isolated that contains ~2.9 kb of promoter upstream of ~4.9 kb of DNA incorporating at least 9 exons. These specify a full-length transcript of ~2 kb, with exons 2–9 encoding the 371 amino acid mESX protein (see FIG. 3).

The following putative structural and/or functional domains within the 42 kDA ESX protein were conserved between mouse and human (FIG. 4):

An Exon 3 encoded POINTED/A-region found in a small subset of all Ets;

An amphilic helix and serine rich box encoded by exons 5 and 6;

A nucleoplasmin-type nuclear targeting sequence encoded by exon 7; and

Figure 6:
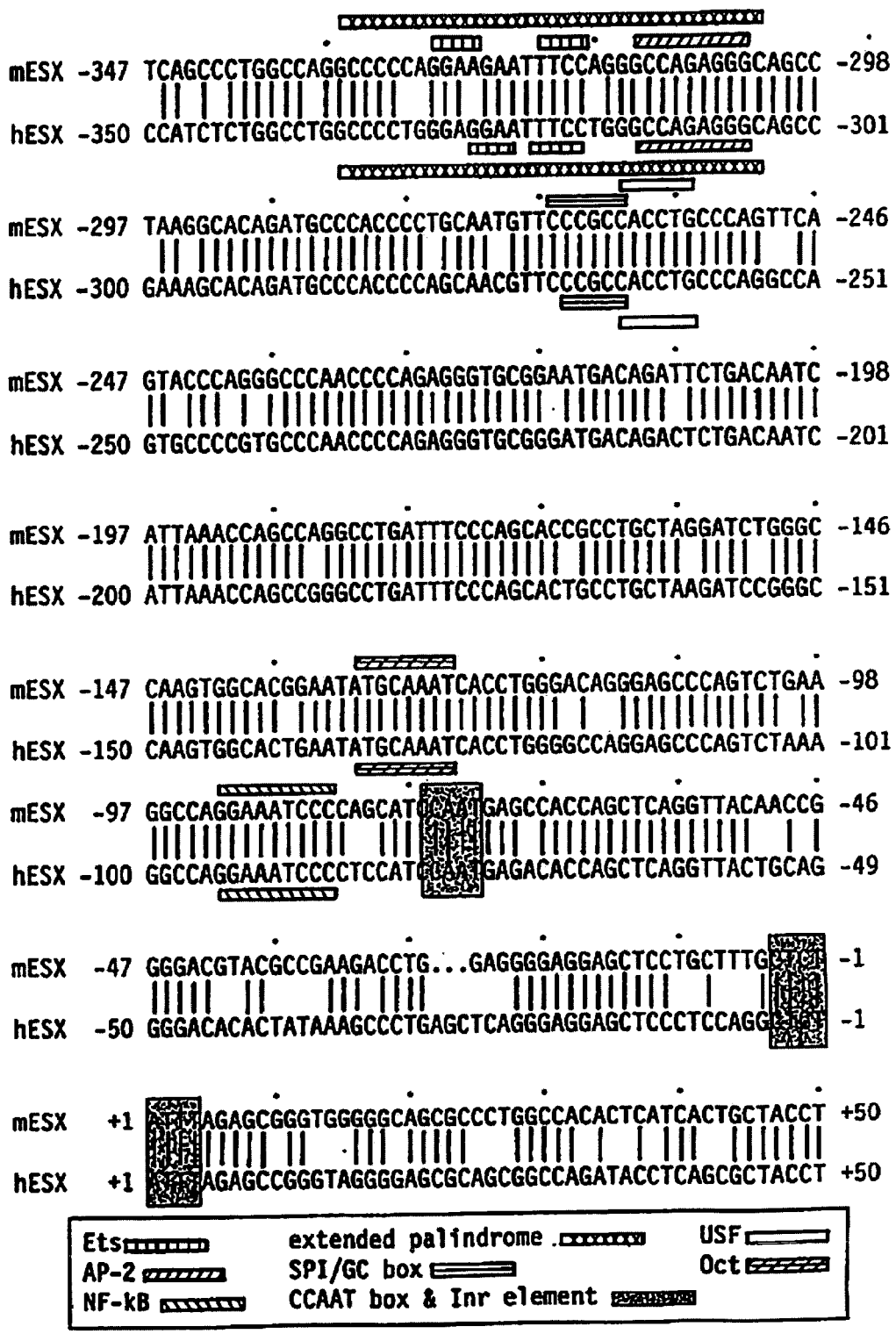
FIG. 6 shows the conserved elements in the mouse ESX (mESX) (SEQ ID NO:30) and human ESX (hESX) (SEQ ID NO:2) proximal promoter.

A helix-turn-helix Ets DNA-binding domain encoded by exons 8 and 9. A comparison of the human ESX and mouse ESX genomic DNA structure is shown in FIG. 6.

The proximal promoter region of mESX (350 bp upstream of transcriptional start site) was 83% homologous to the hESX promoter (FIG. 5). Conserved putative response elements within this region include Ets, AP-2, SP1, USF, Oct, and NF-κB binding sites. A conserved CCAAT box lies ~80 bp upstream of the pyrimidine-rich Inr element which specifies ESX transcript initiation. Unlike hESX, mESX lacks a TATA box.

The comparison of mESX and hESX genomic and cDNA sequences supports a modular model of ESX primary structure in which putative protein domains, first suggested by homology with other proteins, are now shown to be highly conserved and derived from individual exons or exon pairs.

Example 3

Embryo and Mammary Epithelia Cell Expression of ESX

Whole mount analysis of mammary gland morphology was performed as described by Smith (1996) *Breast Cancer Res. Treat.,* 39: 21–31. Endogenous mESX transcripts were detected by Northern blotting using a 5' specific mESX cDNA probe.

Mouse embryos exhibited progressive induction of mESX transcription after 7 days of age, with 17 day levels approximately 10-fold higher than those of 11 day old embryos. ESX mRNA, undetectable in virgin mouse mammary glands, was induced during pregnancy in association with progressing ductal morpohogenesis, branching and lobuloalveolar differentiation. ESX then declined to undetectable levels during lactation, but increased dramatically with 3 days of weaning when milk secretion stops, alveolar epithelium involutes by apoptosis, and glandular remodeling occurs leaving a more mature ductal epithelium system ready for subsequent pregnancy. These data suggest that ESX has a primary role in directing ductal epithelial proliferation and migration in preparation for lobuloalveolar differentiation.

Example 4

Transgenic hESX Model

MMTV-hESX transgenic mice were produced by implanting foster mothers with fertilized eggs microinjected with a full-length hESX expression construct, driven by the MMTV LTR and containing the polyA signaling and splicing sequence from SV40). (The MMTV promoter is well described (Huang et al. (1981) *Cell,* 27: 245–255). In addition, the use of MMTV-LTR for targeted expression of transgenes to the mammary gland of mice and other animals is described in detail in Webster and Muller, (1994) *Sem. Cancer Biol.,* 5: 69–76). hESX transgene expression was detected using a probe specific for the SV40 polyA sequence and confirmed by nested RT-PCR analysis using 5' primers specific for hESX and 3' primers specific for the SV40 polyA sequence.

Founder ($F_0$) lines created as described in Example 3, were tested for transgene presence. Fourteen of fortyone animals carried the transgene. The Founder animals were then mated and 155 day pregnant $F_1$ females were then tested for mammary gland expression of hESX mRNA. Total RNA was extracted from the mammary glands of 15 day pregnant MMTV-hESX transgenic $F_1$ mice. A northern blot of 10 μg of the RNA was probed for sequences specific to the SV40 polyA-containing hESX transcript.

Mammary gland morphology in an MMTV-hESX expressing transgenic mouse appeared abnormal, showing retardation of lobuloalveolar development during pregnancy (15 day, first pregnancy). This morphologic abnormality suggests that failure to turn of ESX in progenitor epithelial cells and alveolar buds leads to continued ductal growth with interrupted mammary gland maturation.

Example 5

ESX is a Transcriptional Activator

To prove that ESX upregulates genes (vs. transcriptionally repressing them), many different hESX-Gal4 fusion constructs were produced in which the DNA-binding domain (DBD) of the yeast Gal4 was chimerically expressed with various portions of human ESX (see, FIG. 11) (for a general description of the method see, e.g., White and Parker (1993) *Analysis of cloned Factors, In Transcription Factors: a practical approach*; D. S. Latchman, ed.; IRL Press at Oxford Univ. Press, Oxford). These fusion constructs were then co-transfected into human breast cancer cells along with a Gal4 binding luciferase reporting expression construct in order to find either an ESX transactivating or repressing domain. A similar Gal4-VP16 construct was used as positive control since the VP16 transactivating domain from Herpes Simplex virus is acknowledged to be one of the strongest of all known transactivators.

ESX transactivated as strongly as VP16 (+++++) (see, FIG. 11) and the minimal ESX domain necessary for this activity is encoded by exon 4 (aa 129–159), an acidic domain containing a central lysine residue (K-145). Subsequent mutations of this domain established that the central K-145 is essential and provides nearly 1000-fold transactivation potency (relative to a neutral residue placed there).

A database revealed that the exon 4-encoded domain is homologous to an essential core domain of all known Topoisomerase I molecules (Stewart et al. (1996) *J. Biol. Chem.* 271:7602–7608; Pommier (1996) *Sem. Oncology* 23: 3–10). Since human Topo-I is a critical intracellular target for the newest and most exciting family of camptothecin-like anticancer agents (like Topotecan, CPT-11, 9AC, etc.; see reviews), this information not only provides important clues as to the molecular transactivation mechanism of ESX, but it indicates that this particular ESX domain may be used to search for or screen (from libraries of chemicals or natural products) for even newer and more effective and selective anticancer agents.

Existing Topo-I agents target a very different, C-terminal conserved domain in the Topo-I enzyme; as yet, there is no specific function assigned to the highly conserved Topo-I Core domain which is homologous to the ESX transactivation domain.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. An isolated nucleic acid comprising a nucleic acid that encodes a polypeptide consisting of the amino acid sequence of SEQ ID NO:16.

2. The nucleic acid of claim 1, wherein said nucleic acid comprises a vector.

* * * * *

SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
      (A) LENGTH: 1116 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..1116
      (D) OTHER INFORMATION: /product= "human ESX"
         /note= "epithelial-restricted with serine box (ESX)"

(xi) SEQUENCE DESCRIPTION: SEQ ID NO:1:

```
ATG GCT GCA ACC TGT GAG ATT AGC AAC ATT TTT AGC AAC TAC TTC AGT      48
Met Ala Ala Thr Cys Glu Ile Ser Asn Ile Phe Ser Asn Tyr Phe Ser
1               5                  10                  15

GCG ATG TAC AGC TCG GAG GAC TCC ACC CTG GCC TCT GTT CCC CCT GCT      96
Ala Met Tyr Ser Ser Glu Asp Ser Thr Leu Ala Ser Val Pro Pro Ala
                20                  25                  30

GCC ACC TTT GGG GCC GAT GAC TTG GTA CTG ACC CTG AGC AAC CCC CAG     144
Ala Thr Phe Gly Ala Asp Asp Leu Val Leu Thr Leu Ser Asn Pro Gln
            35                  40                  45

ATG TCA TTG GAG GGT ACA GAG AAG GCC AGC TGG TTG GGG GAA CAG CCC     192
Met Ser Leu Glu Gly Thr Glu Lys Ala Ser Trp Leu Gly Glu Gln Pro
        50                  55                  60

CAG TTC TGG TCG AAG ACG CAG GTT CTG GAC TGG ATC AGC TAC CAA GTG     240
Gln Phe Trp Ser Lys Thr Gln Val Leu Asp Trp Ile Ser Tyr Gln Val
65                  70                  75                  80

GAG AAG AAC AAG TAC GAC GCA AGC GCC ATT GAC TTC TCA CGA TGT GAC     288
Glu Lys Asn Lys Tyr Asp Ala Ser Ala Ile Asp Phe Ser Arg Cys Asp
```

-continued

```
                85                      90                      95
ATG GAT GGC GCC ACC CTC TGC AAT TGT GCC CTT GAG GAG CTG CGT CTG        336
Met Asp Gly Ala Thr Leu Cys Asn Cys Ala Leu Glu Glu Leu Arg Leu
            100                     105                     110

GTC TTT GGG CCT CTG GGG GAC CAA CTC CAT GCC CAG CTG CGA GAC CTC        384
Val Phe Gly Pro Leu Gly Asp Gln Leu His Ala Gln Leu Arg Asp Leu
                115                     120                     125

ACT TCC AGC TCT TCT GAT GAG CTC AGT TGG ATC ATT GAG CTG CTG GAG        432
Thr Ser Ser Ser Ser Asp Glu Leu Ser Trp Ile Ile Glu Leu Leu Glu
    130                     135                     140

AAG GAT GGC ATG GCC TTC CAG GAG GCC CTA GAC CCA GGG CCC TTT GAC        480
Lys Asp Gly Met Ala Phe Gln Glu Ala Leu Asp Pro Gly Pro Phe Asp
145                     150                     155                 160

CAG GGC AGC CCC TTT GCC CAG GAG CTG CTG GAC GAC GGT CAG CAA GCC        528
Gln Gly Ser Pro Phe Ala Gln Glu Leu Leu Asp Asp Gly Gln Gln Ala
                    165                     170                     175

AGC CCC TAC CAC CCC GGC AGC TGT GGC GCA GGA GCC CCC TCC CCT GGC        576
Ser Pro Tyr His Pro Gly Ser Cys Gly Ala Gly Ala Pro Ser Pro Gly
                180                     185                     190

AGC TCT GAC GTC TCC ACC GCA GGG ACT GGT GCT TCT CGG AGC TCC CAC        624
Ser Ser Asp Val Ser Thr Ala Gly Thr Gly Ala Ser Arg Ser Ser His
                195                     200                     205

TCC TCA GAC TCC GGT GGA AGT GAC GTG GAC CTG GAT CCC ACT GAT GGC        672
Ser Ser Asp Ser Gly Gly Ser Asp Val Asp Leu Asp Pro Thr Asp Gly
    210                     215                     220

AAG CTC TTC CCC AGC GAT GGT TTT CGT GAC TGC AAG AAG GGG GAT CCC        720
Lys Leu Phe Pro Ser Asp Gly Phe Arg Asp Cys Lys Lys Gly Asp Pro
225                     230                     235                 240

AAG CAC GGG AAG CGG AAA CGA GGC CGG CCC CGA AAG CTG AGC AAA GAG        768
Lys His Gly Lys Arg Lys Arg Gly Arg Pro Arg Lys Leu Ser Lys Glu
                    245                     250                     255

TAC TGG GAC TGT CTC GAG GGC AAG AAG AGC AAG CAC GCG CCC AGA GGC        816
Tyr Trp Asp Cys Leu Glu Gly Lys Lys Ser Lys His Ala Pro Arg Gly
                260                     265                     270

ACC CAC CTG TGG GAG TTC ATC CGG GAC ATC CTC ATC CAC CCG GAG CTC        864
Thr His Leu Trp Glu Phe Ile Arg Asp Ile Leu Ile His Pro Glu Leu
                275                     280                     285

AAC GAG GGC CTC ATG AAG TGG GAG AAT CGG CAT GAA GGC GTC TTC AAG        912
Asn Glu Gly Leu Met Lys Trp Glu Asn Arg His Glu Gly Val Phe Lys
290                     295                     300

TTC CTG CGC TCC GAG GCT GTG GCC CAA CTA TGG GGC CAA AAG AAA AAG        960
Phe Leu Arg Ser Glu Ala Val Ala Gln Leu Trp Gly Gln Lys Lys Lys
305                     310                     315                 320

AAC AGC AAC ATG ACC TAC GAG AAG CTG AGC CGG GCC ATG AGG TAC TAC       1008
Asn Ser Asn Met Thr Tyr Glu Lys Leu Ser Arg Ala Met Arg Tyr Tyr
                    325                     330                     335

TAC AAA CGG GAG ATC CTG GAA CGG GTG GAT GGC CGG CGA CTC GTC TAC       1056
Tyr Lys Arg Glu Ile Leu Glu Arg Val Asp Gly Arg Arg Leu Val Tyr
                340                     345                     350

AAG TTT GGC AAA AAC TCA AGC GGC TGG AAG GAG GAA GAG GTT CTC CAG       1104
Lys Phe Gly Lys Asn Ser Ser Gly Trp Lys Glu Glu Glu Val Leu Gln
                355                     360                     365

AGT CGG AAC TGA                                                       1116
Ser Arg Asn
    370
```

(2) INFORMATION FOR SEQ ID NO:2:

(i) SEQUENCE CHARACTERISTICS:
        (A) LENGTH: 371 amino acids (B) TYPE: amino acid
        (D) TOPOLOGY: linear (ii) MOLECULE TYPE: protein (xi) SEQUENCE DESCRIPTION: SEQ ID NO:2:

Met Ala Ala Thr Cys Glu Ile Ser Asn Ile Phe Ser Asn Tyr Phe Ser
 1               5                  10                  15

Ala Met Tyr Ser Ser Glu Asp Ser Thr Leu Ala Ser Val Pro Pro Ala
            20                  25                  30

Ala Thr Phe Gly Ala Asp Asp Leu Val Leu Thr Leu Ser Asn Pro Gln
        35                  40                  45

Met Ser Leu Glu Gly Thr Glu Lys Ala Ser Trp Leu Gly Glu Gln Pro
    50                  55                  60

Gln Phe Trp Ser Lys Thr Gln Val Leu Asp Trp Ile Ser Tyr Gln Val
65                  70                  75                  80

Glu Lys Asn Lys Tyr Asp Ala Ser Ala Ile Asp Phe Ser Arg Cys Asp
                85                  90                  95

Met Asp Gly Ala Thr Leu Cys Asn Cys Ala Leu Glu Glu Leu Arg Leu
            100                 105                 110

Val Phe Gly Pro Leu Gly Asp Gln Leu His Ala Gln Leu Arg Asp Leu
        115                 120                 125

Thr Ser Ser Ser Asp Glu Leu Ser Trp Ile Ile Glu Leu Leu Glu
    130                 135                 140

Lys Asp Gly Met Ala Phe Gln Glu Ala Leu Asp Pro Gly Pro Phe Asp
145                 150                 155                 160

Gln Gly Ser Pro Phe Ala Gln Glu Leu Leu Asp Asp Gly Gln Gln Ala
                165                 170                 175

Ser Pro Tyr His Pro Gly Ser Cys Gly Ala Gly Ala Pro Ser Pro Gly
            180                 185                 190

Ser Ser Asp Val Ser Thr Ala Gly Thr Gly Ala Ser Arg Ser Ser His
        195                 200                 205

Ser Ser Asp Ser Gly Gly Ser Asp Val Asp Leu Asp Pro Thr Asp Gly
    210                 215                 220

Lys Leu Phe Pro Ser Asp Gly Phe Arg Asp Cys Lys Lys Gly Asp Pro
225                 230                 235                 240

Lys His Gly Lys Arg Lys Arg Gly Arg Pro Arg Lys Leu Ser Lys Glu
                245                 250                 255

Tyr Trp Asp Cys Leu Glu Gly Lys Lys Ser Lys His Ala Pro Arg Gly
            260                 265                 270

Thr His Leu Trp Glu Phe Ile Arg Asp Ile Leu Ile His Pro Glu Leu
        275                 280                 285

Asn Glu Gly Leu Met Lys Trp Glu Asn Arg His Glu Gly Val Phe Lys
    290                 295                 300

Phe Leu Arg Ser Glu Ala Val Ala Gln Leu Trp Gly Gln Lys Lys Lys
305                 310                 315                 320

Asn Ser Asn Met Thr Tyr Glu Lys Leu Ser Arg Ala Met Arg Tyr Tyr
                325                 330                 335

Tyr Lys Arg Glu Ile Leu Glu Arg Val Asp Gly Arg Arg Leu Val Tyr
            340                 345                 350

Lys Phe Gly Lys Asn Ser Ser Gly Trp Lys Glu Glu Val Leu Gln
        355                 360                 365

Ser Arg Asn
    370

(2) INFORMATION FOR SEQ ID NO:3:

(i) SEQUENCE CHARACTERISTICS:
        (A) LENGTH: 1907 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 96..1211
        (D) OTHER INFORMATION: /product= "human ESX"
            /note= "epithelial-restricted with serine box (ESX)"

(xi) SEQUENCE DESCRIPTION: SEQ ID NO:3:

```
CGGCCAGATA CCTCAGCGCT ACCTGGCGGA ACTGGATTTC TCTCCCGCCT GCCGGCCTGC     60

CTGCCACAGC CGGACTCCGC CACTCCGGTA GCCTCATGGC TGCAACCTGT GAGATTAGCA    120

ACATTTTTAG CAACTACTTC AGTGCGATGT ACAGCTCGGA GGACTCCACC CTGGCCTCTG    180

TTCCCCCTGC TGCCACCTTT GGGGCCGATG ACTTGGTACT GACCCTGAGC AACCCCCAGA    240

TGTCATTGGA GGGTACAGAG AAGGCCAGCT GGTTGGGGGA ACAGCCCCAG TTCTGGTCGA    300

AGACGCAGGT TCTGGACTGG ATCAGCTACC AAGTGGAGAA GAACAAGTAC GACGCAAGCG    360

CCATTGACTT CTCACGATGT GACATGGATG GCGCCACCCT CTGCAATTGT GCCCTTGAGG    420

AGCTGCGTCT GGTCTTTGGG CCTCTGGGGG ACCAACTCCA TGCCCAGCTG CGAGACCTCA    480

CTTCCAGCTC TTCTGATGAG CTCAGTTGGA TCATTGAGCT GCTGGAGAAG GATGGCATGG    540

CCTTCCAGGA GGCCCTAGAC CCAGGGCCCT TGACCAGGG CAGCCCCTTT GCCCAGGAGC    600

TGCTGGACGA CGGTCAGCAA GCCAGCCCCT ACCACCCCGG CAGCTGTGGC GCAGGAGCCC    660

CCTCCCCTGG CAGCTCTGAC GTCTCCACCG CAGGGACTGG TGCTTCTCGG AGCTCCCACT    720

CCTCAGACTC CGGTGGAAGT GACGTGGACC TGGATCCCAC TGATGGCAAG CTCTTCCCCA    780

GCGATGGTTT TCGTGACTGC AAGAAGGGGG ATCCCAAGCA CGGGAAGCGG AAACGAGGCC    840

GGCCCCGAAA GCTGAGCAAA GAGTACTGGG ACTGTCTCGA GGGCAAGAAG AGCAAGCACG    900

CGCCCAGAGG CACCCACCTG TGGGAGTTCA TCCGGGACAT CCTCATCCAC CCGGAGCTCA    960

ACGAGGGCCT CATGAAGTGG GAGAATCGGC ATGAAGGCGT CTTCAAGTTC CTGCGCTCCG   1020

AGGCTGTGGC CCAACTATGG GGCCAAAAGA AAAGAACAG CAACATGACC TACGAGAAGC   1080

TGAGCCGGGC CATGAGGTAC TACTACAAAC GGGAGATCCT GGAACGGGTG GATGCCGGC   1140

GACTCGTCTA CAAGTTTGGC AAAAACTCAA GCGGCTGGAA GGAGGAAGAG GTTCTCCAGA   1200

GTCGGAACTG AGGGTTGGAA CTATACCCGG GACCAAACTC ACGGACCACT CGAGGCCTGC   1260

AAACCTTCCT GGGAGGACAG GCAGGCCAGA TGGCCCCTCC ACTGGGGAAT GCTCCCAGCT   1320

GTGCTGTGGA GAGAAGCTGA TGTTTTGGTG TATTGTCAGC CATCGTCCTT GGACTCGGAG   1380

ACTATGGCCT CGCCTCCCCA CCCTCCTCTT GGAATTACAA GCCCTGGGGT TTGAAGCTGA   1440

CTTTATAGCT GCAAGTGTAT CTCCTTTTAT CTGGTGCCTC CTCAAACCCA GTCTCAGACA   1500

CTTAAATGCA GACAACACCT TCTTCCTGCA GACACTTGGA CTGAGCCAAG GAGGCTTGGG   1560

AGGCCCTAGG GAGCACCGTG ATGGAGAGGA CAGAGCAGGG GCTCCAGCAC TTCTTTCTGG   1620

ACTGGCGTTC ACCTCCCTGC TCAGTGCTTG GGCTCCACGG GCAGGGGTCA GAGCACTCCC   1680

TAATTTATGT GCTATATAAA TATGTCAGAT GTACATAGAG ATCTATTTTT TCTAAAACAT   1740

TCCCCTCCCC ACTCCTCTCC CACAGAGTGC TGGACTGTTC CAGGCCCTCC AGTGGGCTGA   1800
```

```
TGCTGGGACC CTTAGGATGG GGCTCCCAGC TCCTTTCTCC TGTGAATGGA GGCAGAGACC    1860

TCCAATAAAG TGCCTTCTGG GCTTTTTCTA AAAAAAAAAA AAAAAAA                 1907

(2) INFORMATION FOR SEQ ID NO:4:

(i) SEQUENCE CHARACTERISTICS:
        (A) LENGTH: 189 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..189
        (D) OTHER INFORMATION: /note= "first variable region
            (nucleotides 1-189 of SEQ ID NO:1)"

(xi) SEQUENCE DESCRIPTION: SEQ ID NO:4:

ATGGCTGCAA CCTGTGAGAT TAGCAACATT TTTAGCAACT ACTTCAGTGC GATGTACAGC    60

TCGGAGGACT CCACCCTGGC CTCTGTTCCC CCTGCTGCCA CCTTTGGGGC CGATGACTTG    120

GTACTGACCC TGAGCAACCC CCAGATGTCA TTGGAGGGTA CAGAGAAGGC CAGCTGGTTG    180

GGGGAACAG                                                            189

(2) INFORMATION FOR SEQ ID NO:5:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..120
        (D) OTHER INFORMATION: /note= "pointed region (nucleotides
            190-309 of SEQ ID NO:1)"

(xi) SEQUENCE DESCRIPTION: SEQ ID NO:5:

CCCCAGTTCT GGTCGAAGAC GCAGGTTCTG GACTGGATCA GCTACCAAGT GGAGAAGAAC    60

AAGTACGACG CAAGCGCCAT TGACTTCTCA CGATGTGACA TGGATGGCGC CACCCTCTGC    120

(2) INFORMATION FOR SEQ ID NO:6:

(i) SEQUENCE CHARACTERISTICS:
        (A) LENGTH: 252 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..252
        (D) OTHER INFORMATION: /note= "second variable region
            (nucleotides 310-561 of SEQ ID NO:1)"

(xi) SEQUENCE DESCRIPTION: SEQ ID NO:6:

AATTGTGCCC TTGAGGAGCT GCGTCTGGTC TTTGGGCCTC TGGGGACCA ACTCCATGCC     60

CAGCTGCGAG ACCTCACTTC CAGCTCTTCT GATGAGCTCA GTTGGATCAT TGAGCTGCTG    120

GAGAAGGATG GCATGGCCTT CCAGGAGGCC CTAGACCCAG GGCCCTTTGA CCAGGGCAGC    180
```

CCCTTTGCCC AGGAGCTGCT GGACGACGGT CAGCAAGCCA GCCCCTACCA CCCCGGCAGC    240

TGTGGCGCAG GA                                                       252

(2) INFORMATION FOR SEQ ID NO:7:

(i) SEQUENCE CHARACTERISTICS:
        (A) LENGTH: 84 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..84
        (D) OTHER INFORMATION: /note= "second variable region
            (amino acids 104-187 of SEQ ID NO:2)"

(xi) SEQUENCE DESCRIPTION: SEQ ID NO:7:

Asn Cys Ala Leu Glu Glu Leu Arg Leu Val Phe Gly Pro Leu Gly Asp
1               5                   10                  15

Gln Leu His Ala Gln Leu Arg Asp Leu Thr Ser Ser Ser Ser Asp Glu
            20                  25                  30

Leu Ser Trp Ile Ile Glu Leu Leu Glu Lys Asp Gly Met Ala Phe Gln
        35                  40                  45

Glu Ala Leu Asp Pro Gly Pro Phe Asp Gln Gly Ser Pro Phe Ala Gln
    50                  55                  60

Glu Leu Leu Asp Asp Gly Gln Gln Ala Ser Pro Tyr His Pro Gly Ser
65                  70                  75                  80

Cys Gly Ala Gly (2) INFORMATION FOR SEQ ID NO:8:

(i) SEQUENCE CHARACTERISTICS:
        (A) LENGTH: 153 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..153
        (D) OTHER INFORMATION: /note= "serine-rich region
            (nucleotides 562-714 of SEQ ID NO:1)"

(xi) SEQUENCE DESCRIPTION: SEQ ID NO:8:

GCCCCCTCCC CTGGCAGCTC TGACGTCTCC ACCGCAGGGA CTGGTGCTTC TCGGAGCTCC    60

CACTCCTCAG ACTCCGGTGG AAGTGACGTG GACCTGGATC CCACTGATGG CAAGCTCTTC   120

CCCAGCGATG GTTTTCGTGA CTGCAAGAAG GGG                                153

(2) INFORMATION FOR SEQ ID NO:9:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..105

(D) OTHER INFORMATION: /note= "third variable region
                    (nucleotides 715-819 of SEQ ID NO:1)"

(xi) SEQUENCE DESCRIPTION: SEQ ID NO:9:

GATCCCAAGC ACGGGAAGCG GAAACGAGGC CGGCCCCGAA AGCTGAGCAA AGAGTACTGG      60

GACTGTCTCG AGGGCAAGAA GAGCAAGCAC GCGCCCAGAG GCACC                     105

(2) INFORMATION FOR SEQ ID NO:10:

(i) SEQUENCE CHARACTERISTICS:
            (A) LENGTH: 243 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..243
            (D) OTHER INFORMATION: /note= "Ets DNA binding domain
                    (nucleotides 820-1062 of SEQ ID NO:1)"

(xi) SEQUENCE DESCRIPTION: SEQ ID NO:10:

CACCTGTGGG AGTTCATCCG GGACATCCTC ATCCACCCGG AGCTCAACGA GGGCCTCATG      60

AAGTGGGAGA ATCGGCATGA AGGCGTCTTC AAGTTCCTGC GCTCCGAGGC TGTGGCCCAA     120

CTATGGGGCC AAAAGAAAAA GAACAGCAAC ATGACCTACG AGAAGCTGAG CCGGGCCATG     180

AGGTACTACT ACAAACGGGA GATCCTGGAA CGGGTGGATG GCCGGCGACT CGTCTACAAG     240

TTT                                                                  243

(2) INFORMATION FOR SEQ ID NO:11:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..51
            (D) OTHER INFORMATION: /note= "fourth variable region
                    (nucleotides 1063-1113 of SEQ ID NO:1)"

(xi) SEQUENCE DESCRIPTION: SEQ ID NO:11:

GGCAAAAACT CAAGCGGCTG GAAGGAGGAA GAGGTTCTCC AGAGTCGGAA C               51

(2) INFORMATION FOR SEQ ID NO:12:

(i) SEQUENCE CHARACTERISTICS:
            (A) LENGTH: 16 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..16
            (D) OTHER INFORMATION: /note= "C-terminal 16 amino acids
                    (amino acids 356-371 or SEQ ID NO:2)"

(xi) SEQUENCE DESCRIPTION: SEQ ID NO:12:

Lys Asn Ser Ser Gly Trp Lys Glu Glu Glu Val Leu Gln Ser Arg Asn (2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..21
        (D) OTHER INFORMATION: /note= "5' ESX-DBD primer"

(xi) SEQUENCE DESCRIPTION: SEQ ID NO:13:

```
CCGGGACATC CTCATCCACC C                                        21
```

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..21
        (D) OTHER INFORMATION: /note= "3' ESX-DBD primer"

(xi) SEQUENCE DESCRIPTION: SEQ ID NO:14:

```
GTACCTCATG GCCCGGCTCA G                                        21
```

(2) INFORMATION FOR SEQ ID NO:15:

(i) SEQUENCE CHARACTERISTICS:
        (A) LENGTH: 7752 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(3604..3763, 4152..4373, 4504..4599, 4788
            ..4907, 5055..5144, 5287..5403, 6257..6452, 7001
            ..7112)
        (D) OTHER INFORMATION: /product= "mouse ESX"
            /note= "mouse epithelial-restricted with serine box
            (ESX)"

(xi) SEQUENCE DESCRIPTION: SEQ ID NO:15:

```
GGATCCTTCC AAGGCACTGA CCTCACCCAA TTCTTTCTCA CTTTTCTCCT CCATTTAACT      60

GTGGACGGAA TCAATACTCA GGGGGATGCG CTAGCTCTAA GATTTCTGCA GCTTTGCCTC     120

TCCTGAGCGG AAGCCCCGTG AAGGCAAGGG AGCTAGCTGA TGGACTCTTT GTGGTCTTCT     180

TCCTCTTTGC TCTGGAGACC CAACCAGGTG TTCTTAGGGG AAGGAGCACG TGAGTAGCCA     240

AGAGGCTAAA AGCTGGTTCT CCCACATTCC AGGGTAAGTG ACTGGGTAGA GGGTGTGTCT     300

GCCTCAGGCT GCTTGGAGGA GGTCCCCTGA AGGGCCATGA GAAAATCCTA CCCAGAGCCC     360

TTGGTTTTCC AGCAGCCCTC CACCTAGAGG AAAGGAGCCT GTCGTTCTGA AGATGAAGAG     420

TGGAGCCTAT GGGGGTGGGC AGATTGTGTC CTGGGACAAT GGGGTACCTA AAGAGAAAG      480
```

```
GAATCTCCTT TCGTTTGAGG TCTACCTGGG GGTCGTGTGT CTGTAAATGG GGTGGAGAGA    540

GGAGAAGACA CAGATCTTAT AACGTAGATG CAGGAAATGC TGACAGTTCA GTGTAGAGAA    600

CTTACTCAAT TCATATAGCC TCCAAAGCTA TCTCCTCAGG CAACGCAAAA CAAACCAGTT    660

GGAGCCGCAA GACATCTAAT GGCTTATCGA GTCCCACACC CTCGATTCTT TGCTAATTTT    720

ATGGTTTTGC TTTTGAGACA ATCTACTGTA GCCTAAGATA GCCCCAAACT CAAATGTAGC    780

TGAGGCTGAC TGACCCTGAG CTCTGGAATT CCAGACACAT GCATATCTTT TGCTAGGCAA    840

TAATCGCTCT ACCAGCTGTA CTCCCACATT CCAGGGTAAG TGACTGGAAT TCTCACTTAC    900

TATATCCCTT TAAAAATTCC CTGAGTGGGA TGGTTGTAGC CAGAGGGAAA AGGCACCAAC    960

AACTGCTTGT CACTTTCCAA ATTTGGTAGC CTGAACAAAC CACTTATCAA GACAACAACT   1020

ATATATCATT TCTTTTCTTC TCTCTCTCTC TCTCTCTCTC TCTCTCTCTC TCTCTCTCTC   1080

TCTCTCTCTC TCTCTCTTTN GAAAGAGTCT CACTACTATG TAGCCCTTGA TAACCTAGAA   1140

CTCACTATGT AGTCCAGGCT TGGCCTTCAG CTCGCAGAGG TCCACTTGCC TTGGGAGTTG   1200

AGAGATTAAA GGGATGCATC TCCACATGTG TCCAACAGTG CTTTTTAAAA ATATTTTTAA   1260

AACCATGCTT ACAGCCAGGC ATAGTGGGCG TGCCTTTAAT CCCAGTACTG GGGAGGCAGA   1320

GGTAGGTAGA GTTCTGAGTT GGAGGCTAGC CACATAGTAA GTCCCAGGAT AGCTAGAACT   1380

ATGTAAAGAC CATGTCTCAA AAAAGATGCA CACACACATA TACACACACA CGTTTGTATG   1440

TGTTTGTTTA GTGTGTATGT GTGTGTACAC TTGCACATAA AGGTCAGAGT ACCACATTAC   1500

AGGAGTCAGT TTTCTCCTTT TATCATGTAT GGATGGAACA CGGGTCCATC CATAGCATCC   1560

TTAGCAGCAG GTATCCTTAT CCACTGAGCT ATCTCAGCAG CCCCACATTG CTTATTGGAT   1620

GTTTTTGGAT GAGGATAGTT ATATTAAAAA GGTTTCTGGT GTTGGTCTGG GTAGTTACCC   1680

TTTAACCCAT CTCTAGAGCC TGTCTCTTGA GTTTGAGGCC AGCCTGGTAT ATGTAGCTAG   1740

ACAAAGTTTC AAAAATGAAC AGAATCCTGG GACTAGAACC CATTTGTAGA ATGCTTGCAT   1800

AAGAAGCTCT GGGTTCAACT TCCTGCATCT CCAGAGGGAT TTTGTTCTGT AGTTTTAGTT   1860

TTTCAAGACA GAGTTTCTCT GTGTAGCCCT GGCTGTCCTG GAACTCACTC TGTAGACAAG   1920

GCTGGCCTCG AACTCAGAAA TCCTTCTACC TCTACTTCAG GAGTGCTGGG ATTAAAGATG   1980

TGCGCTGCCC TCCTCCACCC CAATTTGTTT TTGTTTTTTA AGGGCCCCGG TAAACAGTAA   2040

ATTAACATGT GCATCCTGTT TGTCTTTGTA ATGACTCAAA TGTTGGGCTT CTGACCACTA   2100

GAGGGCAGCA GGCAGATACT AATGGACTGG GCGGAGAGAA GGGTAATCAG GAGCAGACCA   2160

GACTCGCGGA TAAACCAAAC AGCACCGCCA GCCGACCCTA GGCGAGGAGA GCGCCACAGG   2220

CACCAAGGGA AGACTTGAAG TAGTGTCTGA TCTCTACCGC TTCAGCAACC ATCGCGTTTG   2280

GGTGGGCTCC AGACAGGCAA AGTGCCAGCA AATGGTCCCT GTAGCTGACT AAACAGACTA   2340

TCAGACCCAA ACCACCACTG GACCGTGAAT GTTGCCCAGT GTGTTGCCTA GCCGCTTTCA   2400

GAATCCCAGC TTCTGGGTGT TGTGGAGGAA ACCCCTTAGC CTCGGTAACT TTCACCAGGC   2460

CCTTCTTGTC TCTAGACATC TAGACAGTTG GAAGCATCAG TCTTGACCCA GCCACCGGTT   2520

CAGATTCTTT GCCTTGCTTT TTCTTCCCCA GTTCAGCCCT GGCCAGGCCC CCAGGAAGAA   2580

TTTCCAGGGC CAGAGGGCAG CCTAAGGCAC AGATGCCCAC CCCTGCAATG TTCCCGCCAC   2640

ATGCCCAGTT CAGTACCCAG GGCCCAACCC CAGAGGGTGC GGAATGACAG ATTCTGACAA   2700

TCATTAAACC AGCCAGGCCT GATTTCCCAG CACCGCCCGT TAGGATATGG GCCAAGTGGC   2760

ACGGAATATG CAAATCACAT GGGACAGGGA GCCCAGTCTG AAGGCCAGGA AATCCCCAGC   2820
```

-continued

| | |
|---|---|
| ATCCAATGAG CCACCAGCTC AGGTTACAAC CGGGGACGTA CGCCGAAGAC CTGGAGGGGA | 2880 |
| GGAGCTCCTG CTTTGCTCTA TTTAGAGCGG GTGGGGGCAG CGCCCTGGCC ACACTCATCA | 2940 |
| CTGCTACCTG CGGAGCCTTC GACCGCTTAG ATTTTTTCCC TTCCTGTGGC CTCAGAAGCC | 3000 |
| TGCTCACCCG CCTGCCACAC CGAACCCTGA CACACCTCGG TACGGTCACA TTCCCTAACT | 3060 |
| CTGGCTCCAG GAACCGTCCA GTGGATTTAC AGTTCTGAAC TTAATCACTC AGGCTTGGAG | 3120 |
| GTTCCTAGCT GGAGTGTTGG GGCTACTGTG GGTGTATTCT GGGACTGGTC AGAGACCAGA | 3180 |
| TCGGTGTCTT GGAGGGACAG GGTGGCTTCT TTGGTTCAGG AGCCCACGTG ATTTGTGGAG | 3240 |
| AGACCCCAGA AGAATTTGTA TCATGCTCCC ACCCGCTTTG AGATTATTTT TATTTTTCGG | 3300 |
| AGCCGAATTT CCCAGTTTGG CGCCAGCTGG CCTGACCCTT CTAGGCTCAA GAGAGCATCC | 3360 |
| AACCTCAGCT TCCCCAAGTA GCTGGCTCTT GGTGGTGATG GTGGTGGTGG TGGTGGTGGT | 3420 |
| GGTGGTGGTG GTGTGTGTGT TTGTGTGTGT GTGGTGGTGG GGGGGTGTT GAAGAGAGAA | 3480 |
| TGTCTACAGC AACACTGAAC TTCCTGCCTC TCGGCTGTTG CTGCCCAGGC TTTGCCAGAC | 3540 |
| AGAAATGGAA GTGTATCCTG ACCTGTACCC TCCCCACCTT GTCTCCTCTT CCCAGGGGCC | 3600 |
| CTC ATG GCT GCC ACC TGT GAG ATC AGC AAC GTT TTT AGT AAC TAC TTC<br>    Met Ala Ala Thr Cys Glu Ile Ser Asn Val Phe Ser Asn Tyr Phe<br>     1             5              10            15 | 3648 |
| AAC GCC ATG TAC AGC TCA GAA GAC CCC ACC CTG GCT CCT GCT CCT CCG<br>Asn Ala Met Tyr Ser Ser Glu Asp Pro Thr Leu Ala Pro Ala Pro Pro<br>          20                25               30 | 3696 |
| ACT ACC TTT GGC ACT GAA GAC TTG GTG TTG ACC CTG AAC AAC CAA CAG<br>Thr Thr Phe Gly Thr Glu Asp Leu Val Leu Thr Leu Asn Asn Gln Gln<br>         35               40              45 | 3744 |
| ATG ACA CTG GAA GGT CCA G GTGAGTGCTG TGTAAAATCT TTTCAGACAG<br>Met Thr Leu Glu Gly Pro<br>        50 | 3793 |
| GACACCAATG ATCTGAGAGG CTCTTAGATG ATAAATGGAC AGGGAGGAAG GGTATCCTGG | 3853 |
| AGTTAGTGGC TGGGGAGGAT TTATTCATTC ATATGTTTGT GTAGTACTGG GGAAAGAACC | 3913 |
| CAAACAAGAC CTTATTTATG CTAGACTGTG TTCCTAGTCC CGAGAAGACT GTACTGGCTG | 3973 |
| AGGTGGTGGG AATATAAGAA CTGTGGTGAC AGATTAAGGG AGGATGAACT TGAGAACTAG | 4033 |
| CCATGTTGTG ATTGTGGATA TGTATCTGTC CCTCTCCGCC CCTCCTCGGG TTGTGTAGGA | 4093 |
| CCTCAGACAA GATCCCAAAG GGACAGGACT GATCCTCTGG CTGTACTCCA CCTTGCAG AG<br>                                                                                            Glu | 4153 |
| AAG GCA AGC TGG ACT AGC GAG CGG CCC CAG TTC TGG TCG AAG ACC CAG<br>Lys Ala Ser Trp Thr Ser Glu Arg Pro Gln Phe Trp Ser Lys Thr Gln<br> 55                 60                  65                  70 | 4201 |
| GTT CTG GAG TGG ATC AGC TAC CAA GTG GAG AAG AAC AAG TAT GAC GCC<br>Val Leu Glu Trp Ile Ser Tyr Gln Val Glu Lys Asn Lys Tyr Asp Ala<br>               75                  80                  85 | 4249 |
| AGC TCC ATC GAC TTC TCC CGC TGC AAC ATG GAC GGA GCC ACC CTC TGC<br>Ser Ser Ile Asp Phe Ser Arg Cys Asn Met Asp Gly Ala Thr Leu Cys<br>               90                  95               100 | 4297 |
| AGC TGT GCG CTG GAG GAG CTG CGG CTA GTC TTT GGA CCT CTG GGA GAC<br>Ser Cys Ala Leu Glu Glu Leu Arg Leu Val Phe Gly Pro Leu Gly Asp<br>         105               110              115 | 4345 |
| CAG CTC CAT GCC CAG CTT CGG GAC CTC A GTAAGTCTAG GCTGGGAGCC<br>Gln Leu His Ala Gln Leu Arg Asp Leu<br>     120               125 | 4393 |
| ACAGGGCCTA AAGAGTGAGC GAGGTGGCTG GACTTGGGC AGGAGGGTGC AGCCATCGAG | 4453 |
| CCCCTGCCGG AACCATGGTC GGTGACGCTC TCCCTCCCTG CCTCCGCCAG  CC TCC<br>                                                                          Thr Ser | 4508 |

| | |
|---|---|
| AAC TCT TCT GAT GAA CTC AGC TGG ATC ATC GAG CTG CTG GAG AAG GAT<br>Asn Ser Ser Asp Glu Leu Ser Trp Ile Ile Glu Leu Leu Glu Lys Asp<br>130                 135              140                 145 | 4556 |
| GGC ATG TCC TTC CAA GAG AGC CTA GGC GAC TTG GGC CCC TTT G<br>Gly Met Ser Phe Gln Glu Ser Leu Gly Asp Leu Gly Pro Phe<br>         150                     155 | 4599 |
| GTGAGAACCC ATTTTCTCCC TTTTTCCTCC CTAGCTTGTC TTGTCCCATC TGTAACTCCT | 4659 |
| CCAGAGTGCT ACAGATATTC TCTCCCAACT TGAAAATAAG TCCATAGTCA TTTCTGTGGT | 4719 |
| CCCTGGAGGG TCGTGCCTGT CCTTGCTGGT ATCCTGGGCC TCTCTAAGCT CTTAACTTCT | 4779 |
| TTTCTCAG AT CAG GGA AGT CCT TTT GCC CAG GAA CTC CTG GAT GAT GGC<br>        Asp Gln Gly Ser Pro Phe Ala Gln Glu Leu Leu Asp Asp Gly<br>          160                 165              170 | 4828 |
| CGC CAG GCC AGT CCC TAC TAC TGC AGT ACC TAT GGC CCT GGA GCG CCC<br>Arg Gln Ala Ser Pro Tyr Tyr Cys Ser Thr Tyr Gly Pro Gly Ala Pro<br>    175                 180              185 | 4876 |
| TCC CCC GGC AGC TCT GAT GTC TCC ACT GCA A GTAAGTCCTG CCCTTGCCAC<br>Ser Pro Gly Ser Ser Asp Val Ser Thr Ala<br>190                 195 | 4927 |
| AGCCTGCCTT CTCCAAGTGC CCTAGAGTGC ATCGAGTTCT TACAATACTC ATTCAGTATC | 4987 |
| TGAAGTCTGG GTACGCAGTG ACTGGGTAGG CTGGCCCTGG CATTCAAGTG GTATTCTTCA | 5047 |
| CCCCTAG GG ACC GCT ACT CCC CAG AGT TCC CAT GCC TCT GAC TCC GGT<br>       Arg Thr Ala Thr Pro Gln Ser Ser His Ala Ser Asp Ser Gly<br>           200                 205              210 | 5095 |
| GGA AGT GAT GTG GAC CTG GAC CTC ACC GAG AGC AAG GTC TTC CCT AGA G<br>Gly Ser Asp Val Asp Leu Asp Leu Thr Glu Ser Lys Val Phe Pro Arg<br>   215                 220              225 | 5144 |
| GTGAGTTGAG GGCTGTTCTT GGGGGTCCTG TCCATGGGGT CTAGCCACTC CCCTCTGCCC | 5204 |
| TATGGCTGCA GTTTCTGTAC CAAGGCTCCC TGTTGACACC CTGCCCTTAC CTTCTCTTGA | 5264 |
| CCTTCCAACC CCCTTCCCAT AG AT GAC TTT ACT GAC TAT AAG AAG GGG GAA<br>                       Asp Asp Phe Thr Asp Tyr Lys Lys Gly Glu<br>                           230                 235 | 5315 |
| CCC AAG CAC GGG AAG AGG AAA CGG GGG CGT CCC AGA AAG CTG AGC AAG<br>Pro Lys His Gly Lys Arg Lys Arg Gly Arg Pro Arg Lys Leu Ser Lys<br>240                 245              250                 255 | 5363 |
| GAA TAC TGG GAC TGT CTG GAG GGC AAG AAG AGC AAG CAC G<br>Glu Tyr Trp Asp Cys Leu Glu Gly Lys Lys Ser Lys His<br>         260                 265 | 5403 |
| GTAAGCTCTA AGGGCTGCCA GGCCTGTGGG CGGAGGGATA CTATTCCTTC AGCTTCCACT | 5463 |
| GGCCTCTCAC AGCCGCTGGA ACTCATTGCA TTGACGGGGC TCCATGGCAT TTGTTACTGC | 5523 |
| CTCTTTACAG AGGCCTGCTT GGACTTAGAG AAGAAGGGAA CTGAGGTCCT AGGAGAGGCC | 5583 |
| ATGGAGAGAG TCCAGCCTTC CCACATTCTT CCTCTTTAAC TATCCCTGTA CTTGGCCCCT | 5643 |
| GTCTTGCCTG ATGGAACTTT CCGATGGGGA GGAGGCAGCT GGTGGGTGCT CAGAGCCAGG | 5703 |
| CAGGCTGGGG TGGCTGCGAC TCCAGGCACA GCCTGCTGAA AGAGCCTCGG GCCTTGTGTG | 5763 |
| CTCCAGCTGC TCTGAACCAC CTGGAGGTCA CCCCAAAGGT CTTGCCTGCC GCCTCTTCCA | 5823 |
| TACACACAGA CCTGCACGTA TGCACTCCTG GCCTGCTTTC CTTCTTGTCC CGAGGGGACT | 5883 |
| GTTAATTCCG GGAAGCTGTT TCTTGGTCCC TCAGGCTATA GCAGCTCTC TGACCCCATG | 5943 |
| TGTGCCAAGT TCTCACCACC ACTGGTCCCC ACTGAACCAT GAGCCCCCTC ACAAAGAAGC | 6003 |
| GTGTCTCTGT CGCTGTCCAT CTTAACCAGT TGTTTGATCC TTAACTGGTG AGAGAATCGA | 6063 |
| GCGCTCTGTG CAGTCGGCCT AGCGCATTGC ATTTTGGGGC AGGAAAGGAA GCAGCCACTA | 6123 |

```
TAGCAATCAC TAAGAGGACA TTTCATATAC TCCCATATGC CTTGGCTCTT AGCCTCGTTG    6183

GGATAGGAGA GGCCAGGTCG CCTAGAGGAG AGGGGCACCC CAGACTGATA ACTGAGGAAA    6243

TCTTCCCTTG TAG  CC CCC AGA GGT ACT CAC CTG TGG GAG TTT ATC CGA       6291
               Ala Pro Arg Gly Thr His Leu Trp Glu Phe Ile Arg
                270             275                 280

GAC ATC CTA ATC CAC CCC GAG CTC AAC GAA GGC CTC ATG AAG TGG GAG      6339
Asp Ile Leu Ile His Pro Glu Leu Asn Glu Gly Leu Met Lys Trp Glu
            285                 290                 295

AAC CGG CAC GAG GGT GTG TTC AAG TTT CTT CGC TCA GAG GCC GTG GCC      6387
Asn Arg His Glu Gly Val Phe Lys Phe Leu Arg Ser Glu Ala Val Ala
                300                 305                 310

CAA CTC TGG GGC CAG AAG AAG AAG AAC AGC AAC ATG ACC TAT GAG AAG      6435
Gln Leu Trp Gly Gln Lys Lys Lys Asn Ser Asn Met Thr Tyr Glu Lys
            315                 320                 325

CTG AGC CGA GCC ATG AG  GTGAGTGTGA GCGTCAGGGA CCTCTGCTTG             6482
Leu Ser Arg Ala Met Arg
            330

GGCTCTACTG GCTTCCGCTA GGTTTCACGA GACAGGCCTG AGGCCCGTAT GGAGAGGACA    6542

AGGACAGTGT TGTGGCCCTG TGTAGTTGGT TACGTGCAGC ATGAAGAAAG CGCTGGGCAG    6602

AGATCGTGAG CACACTTAGC TTTAGCTAAC ATTTCTGTGT TTCCTGCAGA CTTGTTCTAA    6662

GAAAGACACT TGAGAGAGAG AAAGAATAGA AATTGACAGC TCAGCTCCCT TGTCTCTGGG    6722

CCACAAAGGT GAACTAGCTC AGCATTGCTA AAGTCCCCTC TCCCTCAGTT CACGGGCCTT    6782

TATGAAAAGC CCCAGGACAT AGCCAGAAGG CACAGAGAAG TAAATGTAGA AGCAGGTGCT    6842

CTGGCCATAA TTACAGATCA CCGCGGCCAC AACAGGTGAG GAGAGGGAAC ACTCAGGCAG    6902

AGAGGGCCAG CTCAGCACAC TGGGGCTGGG AACCAATGCG AACCTCAGTC CATAGCATGC    6962

CTCTTGCCTA CACCTCTGAC CACCTCCTTC CCACGCAG G TAT TAC TAC AAA CGG     7016
                                          Tyr Tyr Tyr Lys Arg
                                                  335

GAG ATC CTG GAA CGG GTG GAT GGC CGA CGG CTC GTC TAC AAG TTT GGC      7064
Glu Ile Leu Glu Arg Val Asp Gly Arg Arg Leu Val Tyr Lys Phe Gly
340                 345                 350                 355

AAG AAC TCT AGT GGC TGG AAG GAA GAA GAG GTT GGA GAG AGT CGG AAT      7112
Lys Asn Ser Ser Gly Trp Lys Glu Glu Glu Val Gly Glu Ser Arg Asn
                360                 365                 370

TAAGGATCGG GGCTGGACCC AGGACCTGAC TCAGGCATGA ACTCCAGAAC TGAAGCCTTC    7172

CTGGAAGGAC AGGCAGGCCT GACGGCCCCC TTAACATGGA TGTGTTCCCT GTGTTGCTGT    7232

AGAGAGGAAG AACCTGTTGG GCGTGCCCTC TGCAGTCTCC TCAAGTGCAG CCTTTGGCCT    7292

CTCTCCTCGC CCTCTTGGAA TTACAAGCCC CGGGTTTGAA CCAACTTGTT CGATAACTCT    7352

TCCAGCTGTG ATTCCAGTTC CCTCCCGTCC CAACATGGAC TGCAAATGAG ACCCACCTGC    7412

AGATGCCTGG CCTCAGCCAA GGAGGCTGGG GAGACTGTGG CAGGAGACTG CAGGGACGGA    7472

GGGGACAGGG TTGTGTCCTC GGTACTTCCT GGACTGCCTT CCACCTCTTT GCTCAGTACT    7532

CAGGCTCCAC AGACGGGGGT CGGATCATCC CTAATTTATG TGCTATAAAT ATTCCAGGTG    7592

TATATAGAGA GCTATTTTTT CTAAAGCATT TCCCCTCCCT GCTCTTCTCC ACTGAGTGCT    7652

GGTGGCCAGA CTGATTTTTT TTTTAGCCCC CCTAACTGGA CCAGCGAGAA GTAGGGTGAT    7712

TCCAGGACCC CCTCTTCCCC CAGAGGGGTC TCCTGGATCC                          7752
```

(2) INFORMATION FOR SEQ ID NO:16:

(i) SEQUENCE CHARACTERISTICS:
        (A) LENGTH: 371 amino acids (B) TYPE: amino acid
(D) TOPOLOGY: linear (ii) MOLECULE TYPE: protein (xi) SEQUENCE DESCRIPTION: SEQ ID NO:16:

```
Met Ala Ala Thr Cys Glu Ile Ser Asn Val Phe Ser Asn Tyr Phe Asn
 1               5                  10                  15

Ala Met Tyr Ser Ser Glu Asp Pro Thr Leu Ala Pro Ala Pro Pro Thr
            20                  25                  30

Thr Phe Gly Thr Glu Asp Leu Val Leu Thr Leu Asn Asn Gln Gln Met
        35                  40                  45

Thr Leu Glu Gly Pro Glu Lys Ala Ser Trp Thr Ser Glu Arg Pro Gln
 50                  55                  60

Phe Trp Ser Lys Thr Gln Val Leu Glu Trp Ile Ser Tyr Gln Val Glu
 65                  70                  75                  80

Lys Asn Lys Tyr Asp Ala Ser Ser Ile Asp Phe Ser Arg Cys Asn Met
                85                  90                  95

Asp Gly Ala Thr Leu Cys Ser Cys Ala Leu Glu Glu Leu Arg Leu Val
            100                 105                 110

Phe Gly Pro Leu Gly Asp Gln Leu His Ala Gln Leu Arg Asp Leu Thr
        115                 120                 125

Ser Asn Ser Ser Asp Glu Leu Ser Trp Ile Ile Glu Leu Leu Glu Lys
130                 135                 140

Asp Gly Met Ser Phe Gln Glu Ser Leu Gly Asp Leu Gly Pro Phe Asp
145                 150                 155                 160

Gln Gly Ser Pro Phe Ala Gln Glu Leu Leu Asp Asp Gly Arg Gln Ala
                165                 170                 175

Ser Pro Tyr Tyr Cys Ser Thr Tyr Gly Pro Gly Ala Pro Ser Pro Gly
            180                 185                 190

Ser Ser Asp Val Ser Thr Ala Arg Thr Ala Thr Pro Gln Ser Ser His
        195                 200                 205

Ala Ser Asp Ser Gly Gly Ser Asp Val Asp Leu Asp Leu Thr Glu Ser
210                 215                 220

Lys Val Phe Pro Arg Asp Asp Phe Thr Asp Tyr Lys Lys Gly Glu Pro
225                 230                 235                 240

Lys His Gly Lys Arg Lys Arg Gly Arg Pro Arg Lys Leu Ser Lys Glu
                245                 250                 255

Tyr Trp Asp Cys Leu Glu Gly Lys Lys Ser Lys His Ala Pro Arg Gly
            260                 265                 270

Thr His Leu Trp Glu Phe Ile Arg Asp Ile Leu Ile His Pro Glu Leu
        275                 280                 285

Asn Glu Gly Leu Met Lys Trp Glu Asn Arg His Glu Gly Val Phe Lys
290                 295                 300

Phe Leu Arg Ser Glu Ala Val Ala Gln Leu Trp Gly Gln Lys Lys Lys
305                 310                 315                 320

Asn Ser Asn Met Thr Tyr Glu Lys Leu Ser Arg Ala Met Arg Tyr Tyr
                325                 330                 335

Tyr Lys Arg Glu Ile Leu Glu Arg Val Asp Gly Arg Arg Leu Val Tyr
            340                 345                 350

Lys Phe Gly Lys Asn Ser Ser Gly Trp Lys Glu Glu Val Gly Glu
        355                 360                 365

Ser Arg Asn
370
```

(2) INFORMATION FOR SEQ ID NO:17:

(i) SEQUENCE CHARACTERISTICS:
        (A) LENGTH: 40 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..40
        (D) OTHER INFORMATION: /note= "human ESX A-region/Pointed
            domain (amino acids 64-103 of SEQ ID NO:2)"

(xi) SEQUENCE DESCRIPTION: SEQ ID NO:17:

```
Pro Gln Phe Trp Ser Lys Thr Gln Val Leu Asp Trp Ile Ser Tyr Gln
1               5                  10                 15

Val Glu Lys Asn Lys Tyr Asp Ala Ser Ala Ile Asp Phe Ser Arg Cys
            20                  25                 30

Asp Met Asp Gly Ala Thr Leu Cys
        35                  40
```

(2) INFORMATION FOR SEQ ID NO:18:

(i) SEQUENCE CHARACTERISTICS:
        (A) LENGTH: 38 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..38
        (D) OTHER INFORMATION: /note= "human ETS-1
            A-region/Pointed domain (amino acids 69-106)"

(xi) SEQUENCE DESCRIPTION: SEQ ID NO:18:

```
Pro Arg Gln Trp Thr Glu Thr His Val Arg Asp Trp Val Met Trp Ala
1               5                  10                 15

Val Asn Glu Phe Ser Leu Lys Gly Val Asp Phe Gln Lys Phe Cys Met
            20                  25                 30

Asn Gly Ala Ala Leu Cys
        35
```

(2) INFORMATION FOR SEQ ID NO:19:

(i) SEQUENCE CHARACTERISTICS:
        (A) LENGTH: 51 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..51
        (D) OTHER INFORMATION: /note= "human ESX serine-rich box
            (amino acids 188-238 of SEQ ID NO:2)"

(xi) SEQUENCE DESCRIPTION: SEQ ID NO:19:

```
Ala Pro Ser Pro Gly Ser Ser Asp Val Ser Thr Ala Gly Thr Gly Ala
1               5                  10                 15

Ser Arg Ser Ser His Ser Ser Asp Ser Gly Gly Ser Asp Val Asp Leu
```

```
                    20                  25                  30
Asp Pro Thr Asp Gly Lys Leu Phe Pro Ser Asp Gly Phe Arg Asp Cys
        35                  40                  45
Lys Lys Gly
    50
```

(2) INFORMATION FOR SEQ ID NO:20:

(i) SEQUENCE CHARACTERISTICS:
        (A) LENGTH: 51 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..51
        (D) OTHER INFORMATION: /note= "SOX4 serine box (amino
            acids 370-420)"

(xi) SEQUENCE DESCRIPTION: SEQ ID NO:20:

```
Ala Pro Ser Ser Ala Pro Ser His Ala Ser Ser Ser Ala Ser Ser His
1               5                  10                  15
Ser Ser Ser Ser Ser Ser Ser Gly Ser Ser Ser Ser Asp Asp Glu Phe
            20                  25                  30
Glu Asp Asp Leu Leu Asp Leu Asn Pro Ser Ser Asn Phe Glu Ser Met
        35                  40                  45
Ser Leu Gly
    50
```

(2) INFORMATION FOR SEQ ID NO:21:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..16
        (D) OTHER INFORMATION: /note= "portion of human ESX serine
            box showing clustering of serine residues opposite a
            hydrophobic face in a helical wheel model"

(xi) SEQUENCE DESCRIPTION: SEQ ID NO:21:

```
Ser Pro Gly Ser Ser Asp Val Ser Thr Ala Gly Thr Gly Ala Ser Arg
1               5                  10                  15
```

(2) INFORMATION FOR SEQ ID NO:22:

(i) SEQUENCE CHARACTERISTICS:
        (A) LENGTH: 81 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..81
        (D) OTHER INFORMATION: /note= "human ESX Ets DNA binding
            domain (amino acids 274-354 of SEQ ID NO:2)"

(xi) SEQUENCE DESCRIPTION: SEQ ID NO:22:

His Leu Trp Glu Phe Ile Arg Asp Ile Leu Ile His Pro Glu Leu Asn
1               5                   10                  15

Glu Gly Leu Met Lys Trp Glu Asn Arg His Glu Gly Val Phe Lys Phe
                20                  25                  30

Leu Arg Ser Glu Ala Val Ala Gln Leu Trp Gly Gln Lys Lys Lys Asn
            35                  40                  45

Ser Asn Met Thr Tyr Glu Lys Leu Ser Arg Ala Met Arg Tyr Tyr Tyr
        50                  55                  60

Lys Arg Glu Ile Leu Glu Arg Val Asp Gly Arg Arg Leu Val Tyr Lys
65                  70                  75                  80

Phe (2) INFORMATION FOR SEQ ID NO:23:

(i) SEQUENCE CHARACTERISTICS:
        (A) LENGTH: 81 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..81
        (D) OTHER INFORMATION: /note= "Elf-1 Ets DNA binding
            domain (amino acids 209-289)"

(xi) SEQUENCE DESCRIPTION: SEQ ID NO:23:

Tyr Leu Trp Glu Phe Leu Leu Ala Leu Leu Gln Asp Lys Ala Thr Cys
1               5                   10                  15

Pro Lys Tyr Ile Lys Trp Thr Gln Arg Glu Lys Gly Ile Phe Lys Leu
                20                  25                  30

Val Asp Ser Lys Ala Val Ser Arg Leu Trp Gly Lys His Lys Asn Lys
            35                  40                  45

Pro Asp Met Asn Tyr Glu Thr Met Gly Arg Ala Leu Arg Tyr Tyr Tyr
        50                  55                  60

Gln Arg Gly Ile Leu Ala Lys Val Glu Gly Gln Arg Leu Val Tyr Gln
65                  70                  75                  80

Phe (2) INFORMATION FOR SEQ ID NO:24:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:24:

Leu Trp Gln Phe Leu Leu
1               5

(2) INFORMATION FOR SEQ ID NO:25:

(i) SEQUENCE CHARACTERISTICS:
        (A) LENGTH: 4 amino acids
        (B) TYPE: amino acid
        (C) STRANDEDNESS:
        (D) TOPOLOGY: linear

```
    (ii) MOLECULE TYPE: peptide (xi) SEQUENCE DESCRIPTION: SEQ ID NO:25:

Lys Leu Ser Arg
1

(2) INFORMATION FOR SEQ ID NO:26:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:26:

Leu Arg Tyr Tyr Tyr
1               5

(2) INFORMATION FOR SEQ ID NO:27:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:27:

Leu Trp Glu Phe
1

(2) INFORMATION FOR SEQ ID NO:28:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:28:

Arg Tyr Tyr Tyr
1

(2) INFORMATION FOR SEQ ID NO:29:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:29:

Arg Leu Val Tyr
1

(2) INFORMATION FOR SEQ ID NO:30:

(i) SEQUENCE CHARACTERISTICS:
        (A) LENGTH: 397 base pairs
        (B) TYPE: nucleic acid
        (C) STRANDEDNESS: single
```

(D) TOPOLOGY: linear (ii) MOLECULE TYPE: DNA (genomic)

(xi) SEQUENCE DESCRIPTION: SEQ ID NO:30:

TCAGCCCTGG CCAGGCCCCC AGGAAGAATT TCCAGGGCCA GAGGGCAGCC TAAGGCACAG      60

ATGCCCACCC CTGCAATGTT CCCGCCACAT GCCCAGTTCA GTACCCAGGG CCCAACCCCA     120

GAGGGTGCGG AATGACAGAT TCTGACAATC ATTAAACCAG CCAGGCCTGA TTTCCCAGCA     180

CCGCCCGTTA GGATATGGGC CAAGTGGCAC GGAATATGCA AATCACATGG GACAGGGAGC     240

CCAGTCTGAA GGCCAGGAAA TCCCCAGCAT CCAATGAGCC ACCAGCTCAG GTTACAACCG     300

GGGACGTACG CCGAAGACCT GGAGGGGAGG AGCTCCTGCT TTGCTCTATT TAGAGCGGGT     360

GGGGGCAGCG CCCTGGCCAC ACTCATCACT GCTACCT                              397

(2) INFORMATION FOR SEQ ID NO:31:

(i) SEQUENCE CHARACTERISTICS:
        (A) LENGTH: 400 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

CCATCTCTGG CCTGGCCCCT GGGAGGAATT TCCTGGGCCA GAGGGCAGCC GAAAGCACAG      60

ATGCCCACCC CAGCAACGTT CCCGCCACCT GCCCAGGCCA GTGCCCCGTG CCCAACCCCA     120

GAGGGTGCGG GATGACAGAC TCTGACAATC ATTAAACCAG CCGGGCCTGA TTTCCCAGCA     180

CTGCCTGCTA AGATCCGGGC CAAGTGGCAC TGAATATGCA AATCACATGG GGCCAGGAGC     240

CCAGTCTAAA GGCCAGGAAA TCCCCTCCAT CCAATGAGAC ACCAGCTCAG GTTACTGCAG     300

GGGACACACT ATAAAGCCCT GAGCTCAGGG AGGAGCTCCC TCCAGGCTCT ATTTAGAGCC     360

GGGTAGGGGA GCGCAGCGGC CAGATACCTC AGCGCTACCT                           400

(2) INFORMATION FOR SEQ ID NO:32:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..31
        (D) OTHER INFORMATION: /note= "TA5 oligonucleotide
            containing Ets responsive element from HER2/neu promoter"

(xi) SEQUENCE DESCRIPTION: SEQ ID NO:32:

GGAGGAGGGC TGCTTGAGGA AGTATAAGAA T                                     31

(2) INFORMATION FOR SEQ ID NO:33:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA -continued

```
    (ix) FEATURE:
         (A) NAME/KEY: -
         (B) LOCATION: 1..31
         (D) OTHER INFORMATION: /note= "m1 mutant TA5 sequence"

(xi) SEQUENCE DESCRIPTION: SEQ ID NO:33:

GGAGGAGGTA TGCTTGAGGA AGTATAAGAA T                               31

(2) INFORMATION FOR SEQ ID NO:34:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
         (A) NAME/KEY: -
         (B) LOCATION: 1..31
         (D) OTHER INFORMATION: /note= "m2 mutant TA5 sequence"

(xi) SEQUENCE DESCRIPTION: SEQ ID NO:34:

GGAGGAGGGC TGCTTGCGGA AGTATAAGAA T                               31

(2) INFORMATION FOR SEQ ID NO:35:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
         (A) NAME/KEY: -
         (B) LOCATION: 1..31
         (D) OTHER INFORMATION: /note= "m3 mutant TA5 sequence"

(xi) SEQUENCE DESCRIPTION: SEQ ID NO:35:

GGAGGAGGGC TGCTTGAGAG AGTATAAGAA T                               31

(2) INFORMATION FOR SEQ ID NO:36:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
         (A) NAME/KEY: -
         (B) LOCATION: 1..31
         (D) OTHER INFORMATION: /note= "m4 mutant TA5 sequence"

(xi) SEQUENCE DESCRIPTION: SEQ ID NO:36:

GGAGGAGGGC TGCTTGACCA AGTATAAGAA T                               31

(2) INFORMATION FOR SEQ ID NO:37:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA
```

```
    (ix) FEATURE:
        (A) NAME/KEY: -
        (B) LOCATION: 1..31
        (D) OTHER INFORMATION: /note= "m5 mutant TA5 sequence"

(xi) SEQUENCE DESCRIPTION: SEQ ID NO:37:

GGAGGAGGGC TGCTTGAGGA AGCATAAGAA T                                              31

(2) INFORMATION FOR SEQ ID NO:38:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

ATACTTCCTC AAGCA                                                                15
```